US007203683B2

(12) United States Patent
Mixon et al.

(10) Patent No.: US 7,203,683 B2
(45) Date of Patent: Apr. 10, 2007

(54) **METHOD AND A SYSTEM FOR AUTOMATING THE EXECUTION OF *AMORE* OVER A HETEROGENOUS NETWORK OF COMPUTERS**

(75) Inventors: Mark B. Mixon, Poulsbo, WA (US); Michael Feese, Seattle, WA (US); Lance Stewart, Bainbridge Island, WA (US); Sridhar Prasad, LaJolla, CA (US)

(73) Assignee: Emerald BioStructures, Inc., Bainbridge Island, WA (US)

( * ) Notice: Subject to any disclaimer, the term of this patent is extended or adjusted under 35 U.S.C. 154(b) by 435 days.

(21) Appl. No.: 10/269,401

(22) Filed: Oct. 11, 2002

(65) Prior Publication Data

US 2004/0215398 A1 Oct. 28, 2004

Related U.S. Application Data

(60) Provisional application No. 60/328,601, filed on Oct. 11, 2001.

(51) Int. Cl.
*G06F 17/30* (2006.01)

(52) U.S. Cl. ...................... 707/10; 707/104.1

(58) Field of Classification Search ............... 707/102, 707/3, 4, 100, 101, 103 R, 104.1, 10; 435/7.21; 457/7.1
See application file for complete search history.

(56) References Cited

U.S. PATENT DOCUMENTS

| 5,375,207 A | 12/1994 | Blakely et al. ............ 395/200 |
| 5,600,833 A | 2/1997 | Senn et al. ................ 395/601 |
| 5,859,972 A | 1/1999 | Subramaniam et al. 395/200.33 |
| 6,240,374 B1 | 5/2001 | Cramer et al. ............... 703/11 |
| 2002/0177167 A1* | 11/2002 | Levinson et al. ........... 435/7.1 |
| 2003/0032069 A1* | 2/2003 | Muraca ..................... 435/7.21 |
| 2003/0180803 A1* | 9/2003 | Chan et al. ................. 435/7.1 |

* cited by examiner

*Primary Examiner*—Frantz Coby
(74) *Attorney, Agent, or Firm*—Christensen O'Connor Johnson Kindness $^{PLLC}$

(57) ABSTRACT

This invention encompasses an apparatus for creating a database containing the results of distributed molecular replacement searches, which comprise data input system for inputting the results of distributed molecular replacement searches and related information and a database generator coupled to said data input system for receiving the results of distributed molecular replacement searches and related information and creating a database for storing the results of distributed molecular replacement searches and related information. The invention includes method of managing the invention of distributed molecular replacement searches.

5 Claims, 68 Drawing Sheets

METHOD AND A SYSTEM FOR
AUTOMATING THE EXECUTION OF
*AMORE* OVER A HETEROGENOUS
NETWORK OF COMPUTERS

This application claims priority to U.S. Provisional application Ser. No. 60/328,601 filed on Oct. 11, 2001 which is incorporated herein by reference.

FIELD OF THE INVENTION

The invention facilitates molecular structure comparison using the method of molecular replacement. The invention encompasses a method for automating, analyzing and storing database searches for molecules with structural similarity.

BACKGROUND OF THE INVENTION

The new initiative for high throughput structural determination promises to revolutionize all stages of the drug discovery process by providing many new high-resolution structures of novel protein folds and complexes between proteins and small molecule drugs. This new knowledge will allow drug development teams to acquire a much better understanding of structure activity relationships. But, before the vision of high throughput protein crystallography can be realized, many time-consuming steps in the process must be overcome. The invention described herein seeks to address two of the bottlenecks in high throughput crystallography: the determination of new protein structures and the identification of new leads for drug compounds. Although the hurdles occur at different stages of the process, both may be addressed by extending pair-wise comparisons of molecules to the scale of large databases.

One of the guiding principles of drug discovery is that similarly shaped molecules are more likely to share biological properties than dissimilar molecules. Thus, a number of algorithms have been developed for making shape-based comparisons of molecules in the field of small molecule drug discovery [1–8]. These approaches rely on strict superpositioning of coordinates, matching and aligning of chemical descriptors, or making topological comparisons of molecules. In general, these methods were designed to find molecules that are similar in activity and so are limited to compounds that vary at a few chemical groups. Thus these methods will group compounds with very similar structure but will not identify molecules where only a small subset of the structure is shared between two compounds. A method that does have the capability to identify subsets of structures but was developed specifically for comparing proteins, is DALI [9]. Briefly, DALI generates a matrix of all interatomic C$\alpha$ vectors for each polypeptide chain in the comparison. Both matrices are reduced to essential contact patterns of structural elements in the polypeptide, and then the patterns are aligned, compared, and scored according the degree of similarity. The scores from multiple alignments are ultimately ranked in the output according to the similarity score. The technique is quite powerful when applied to proteins with known structures; however, there is no means to extend the software to other types of molecules or to include protein atom types other than C$\alpha$ in the comparison. A more flexible pair-wise comparison of molecules that can be extended to many types of structures must be an integral component of the drug discovery process and any improvement in methodology will speed the way to new drug leads.

Beyond small molecule drug discovery, another arena in which pair-wise comparison of structures is important is in the determination of new protein structures through x-ray crystallographic methods. Two common approaches to solving structures are available to the crystallographer: one is multiple isomorphous replacement (MIR), and the other is molecular replacement (MR). MR can be thought of as a type of pair-wise comparison between molecules, but with the special condition that for one of the molecules the structure has not been modeled. MR consists of positioning and orienting the structure of a known molecule in the crystal environment of a protein for which x-ray data is available. Fourier-based Patterson methods are used to generate grids containing peaks that represent interatomic distances for the x-ray data and the structure of the known model. The grids are rotated and translated with respect to one another until the correlation is maximized. MR is used exclusively when crystallographic data is collected from a protein with strong structural homology to another protein. In most cases where MR is applied, the known structure comprises 25% or more of the mass of the unknown protein. Furthermore, as long as there is high structural homology, molecular replacement has succeeded with sequence homology as low as 33% as in the case for protein kinases [10]. In general, this means that MR has only been useful in the context of a protein that has been very well characterized (for which the function is known or guessed). Using MR to help solve structures of the enormous numbers of proteins with unknown function identified in the human genome project would at first seem unfeasible.

Without functional information the search space for candidate models becomes much larger and the barriers to applying MR much greater. In the past, when confronted with a large search space, a crystallographer would abandon MR in favor of other, more time-consuming approaches such as MIR. But the availability of powerful computers and the growing number of protein structures deposited with the Protein Data Bank (PDB) could potentially make molecular replacement much more viable technique. Currently, there are over 14,000 structures in the PDB, and that number is increasing exponentially [11]. As more folds are deposited the likelihood of a match between a model in the PDB and the subject protein increase accordingly. With the invention available to mine protein structural databases systematically and automatically, it should be possible to use molecular replacement for the ab initio determination of any protein structure. Current methods for automating molecular replacement searches, however, are too primitive.

Most current molecular replacement algorithms are modifications of the original rotation function [12] and translation function formulated by Crowther and Blow [13]. The existing embodiments currently do not permit automated database searches; however, two programs appear to be promising candidates for modifications to allow them to do database searches: EPMR [14] and AMoRe [15].

EPMR employs evolutionary search algorithms on a variation of the brute force six-dimensional search for rotation and translation solutions. The algorithm randomly samples six-dimensional space to find a set of starting solutions with high correlation coefficients. Those that satisfy criteria set by the program are subjected to iterative rounds of searches in which the starting orientation of the models have been shifted randomly by small increments. The process is repeated until the solutions are optimized, and then the program calls for a round of local rigid body refinement. The authors claim better signal-to-noise ratios in the solutions and a higher tolerance of errors and incompleteness in the search models than AMoRe.

However, EPMR is a time-consuming algorithm, and so AMoRe is still preferred by many because of its speed and ability to test many solutions simultaneously. AMoRe is based on a fast rotation function using spherical harmonics and Bessel function expansions. The modifications to the rotation search permit more accurate calculation of the rotation matrices and provide better resolution of the rotation peaks.

Even though the execution time for AMoRe is must faster than EPMR, AMoRe has two limitations that make it cumbersome to use for high volume comparisons. In the normal mode of operation, AMoRe must be run in an iterative manner. A crystallographer intervenes at the end of each cycle to analyze and parse out needed parameters from the log files generated by AMoRe and feeds them into the next round of computation. Thus, AMoRe lacks automation. Furthermore, AMoRe requires support programs to manage input data. AMoRe is part of the CCP4 program suite, and uses defined input formats in order to make it compatible with other programs in the suite. As such is the case, AMoRe requires that input data be passed through the programs f2mtz and pdbset. All the programs, including AMoRe, are designed to run under a single processor and cannot be recompiled easily to take advantage of multiple CPUs. Both of these conditions prevent a user from taking advantage of the computing power normally available to distributable applications.

The lack of automation and limited computing power available to AMoRe make an exhaustive search of the complete protein data bank impractical. Assuming a dedicated crystallographer could edit, write, and parse the files necessary to complete a molecular replacement search every 10 minutes, then a crystallographer working around the clock would take more than 100 days to complete the task. Aside from the Herculean effort on the part of the crystallographer, keeping track of the output generated from the effort would also require a database. Currently, there are no programs available that satisfy the requirement for conducting high throughput pair-wise shape-based comparisons of protein molecules or small molecules.

SUMMARY OF THE INVENTION

The invention is aimed at providing a system for conducting high throughput searches for molecular replacement solutions of crystallographic data sets. The invention includes a graphical user interface (GUI), an execution manager, a CCP4 manager, and a referential database to hold search models, track command file parameters, and store molecular replacement solutions. The software also includes tools to recruit and organize hosts on a local area network into a computing cluster. The GUI, MySQL database, and PVM message-passing interface is compatible with the three major platforms (Windows NT, Unix/Linux, and Macintosh (OSX)). The software does not include programs of the CCP4 suite. Only Linux/Unix and Windows NT support the CCP4 programs.

Graphical User Interface

The graphical interface allows the user to launch a number of database managers to execute a round of automated molecular replacement. The main database managers included in the invention are a user manger, a project manager, a host manager, a model manager, a reflection manager, and a run manager.

User Manger

The user manager captures and maintains information regarding the accounts of users. The user manger GUI lists user names, and in a separate text window, the projects associated with a particular user. Preferably, the manager includes a GUI that may be spawned from the main user manager to enter new user information. The new user GUI may be used to enter into the database information such as username and password. The main user manger also allows a user to spawn a project manager window.

Project Manager

The project manger captures and maintains information regarding user projects. The project manager GUI lists projects stored in the database for any given user and, in a separate text window, the runs associated with a particular project. Preferably, the manager includes a GUI that may be spawned from the main project manger to enter new project information. The new project GUI may be used to enter into the database information such as the project name and any comments associated with the project. The main project manager also allows the user to spawn a run manager window.

Host Manager

The host manager captures and maintains information regarding computer hosts on a local area network. Preferably, the manager includes a GUI allowing the user to enter information such as hostname and IP address. The identities of computers added through the host manager are used dynamically to generate a molecular replacement computing cluster. A window that lists hosts currently in the cluster and their status is also available in the host manager window.

Model Manager

The model manager captures and maintains information regarding a macromolecule or small molecule. The dialog window allows users to load coordinates from a protein or small molecule model file into the database.

Reflection Manager

The reflection manager captures and maintains information regarding reflection data sets. The dialog window allows the user to load a reflection data set from the hard disk into the database. Preferably, the manager includes text fields for unit cell dimensions and space group of the reflection data set, which is stored along with the H,K,L,F, and Sigma of each reflection in the data set.

Run Manager

The run manager captures and maintains information regarding a molecular replacement run. The run manager consists of two tab widgets. One the input tab widget captures and maintains data necessary to begin molecular replacement search on a cluster of computers. The output tab widget allows the user to interface with the database where solutions from molecular replacement runs are stored.

RunManager: Input Tab

Preferably, the input tab of the dialog window allows users to enter parameters that will be used to define a molecular replacement search. The dialog is composed of four sections that allow the user to interact with the database: a run status monitor, a reflection queue manager, a model queue manager, and command file manager. The run manager allows the user to select between a fully automated molecular replacement (multiple model mode) and a single pair-wise search (single model mode). In multiple model mode, the program sets the parameters of command files required for execution at run time. In single model mode, the user must set the parameters of each command file prior to execution. The reflection queue manager and the model queue manager allows the user to select input data sets and search models to be used in the molecular replacement search. The search parameter section of the run manager allows the user to choose how each model in the model queue will be treated during the search. The user has the ability to select whether to use the whole model or whether to divide the model into smaller fragments. Each model can be divided into chains, domains, or 50-residue polypeptide fragments. Additionally the user may choose how to rank the solutions identified in the rotation function. The rotation function output from AMoRe provides a correlation coefficient for amplitudes (CCF), an R-factor, a correlation coefficient for intensities (CCI), and a correlation coefficient for peaks in the Patterson map (CCP). The application allows the user to chose between CCF and CCP, as philosophies differ on which value is best to use when ranking the strength of the solution. Finally, the run status monitor provides the user with real time updates of the run status.

Run Manager: Output Tab

The output tab of the run manager allows the user to view a real-time composite of all the solutions of a molecular replacement search. In order to evaluate the quality of any given solution, each solution is identified in the view with the search model and statistics calculated for the solution. The solution consists of Euler angles (alpha, beta, and gamma) and unit cell translations on the principle axes. The correlation coefficient ratio, signal-to-noise, correlation coefficient of amplitudes, R-factor, and an inclusive and exclusive Kurtosis factor are listed with a solution. A statistics cutoff control panel allows the user to set the high and low cutoff levels for all the statistics in the list view.

The contents of the list view may be written to the disc in an ASCII format file. Each solution may be applied to the coordinates of the starting search model and written to the hard disc in a Brookhaven format file. At the user's option, the corresponding calculated CCP4 map, coordinate file, or sequence for a particular combination of search model and solutions may be written to the hard disc. These files, in combination with the statistics, are used to evaluate the validity of molecular replacement solutions.

Execution Manager

The execution manager maintains a list of slave hosts, coordinates execution of the CCP4 manager on the slave hosts, and provides error checking for the computer cluster. The execution manager communicates with CCP4 managers through PVM client libraries. Parameters selected in the run manager are passed through the PVM interface to slave hosts. These parameters determine how models in the database are processed, how rotation solutions are sorted, and instructions on how to fragment search models in the molecular replacement search.

CCP4 Manager

Once the CCP4 manager receives the information passed on by the execution manager, the appropriate model data and reflection data sets are downloaded to the hard disk. Both the reflection file and the search model file are converted to a format suitable for input into AMoRe using executables f2mtz and pdbset in the CCP4 suite. The execution manager automatically writes out the appropriately configured command files to the hard disk. The CCP4 manager executes each command file and the output is captured in log files on the hard disk. Next, the log files are parsed using filters coded into the CCP4 manager. The log files are filtered for parameters that determine how the next step in the command file queue is to be executed. The input and output parameters are captured in the CCP4 manager and uploaded to the database for future reference. Of particular interest are the solutions obtained from the rotation function in AMoRe. Together, the hundred top peaks in the Patterson function determine whether a particular search model has a molecular replacement solution for the data set in question. The solutions are analyzed to give a signal-to-noise ratio, a kurtosis factor and a linear correlation coefficient. The statistical descriptors along with the Euler angles and unit cell translations are stored in the database so that solutions for the particular model may be compared with all other solutions through the output tab in the run manager.

The invention represents an advance in the way molecular replacement searches are conducted. It allows the user to bypass all of the labor-intensive steps required in the manual implementation of the molecular replacement program AMoRe. The invention provides a system for dynamically creating a cluster of computers and, in turn, provides the means to distribute AMoRe on different host machines. The increased computing resources that can be harnessed and applied to a molecular replacement solution make it possible to undertake high throughput molecular replacement searches of entire databases. Moreover, the invention removes from the user's consideration the attendant problems of filtering, analyzing and recording output. All these tasks are automated in the system, reducing drastically the time and effort required to carryout a database search. A direct benefit of the invention is the ability to find potential starting models for refinement quickly and without precise knowledge of protein function. At the same time, a molecular replacement solution obtained from the invention for a protein with unknown function, will allow users to quickly narrow the possible range of functions and provide greater focus to the assay design process.

Shows the main manager GUI according to the present invention

FIG. 2

Shows a functional flow diagram for the main manager according to the present invention.

FIG. 3

Shows the user manager GUI according to the present invention

FIG. 4

Shows the functional flow diagram for the user manager according to the present invention.

FIG. 5

Shows the new user manager GUI according to the present invention.

Figure 6:
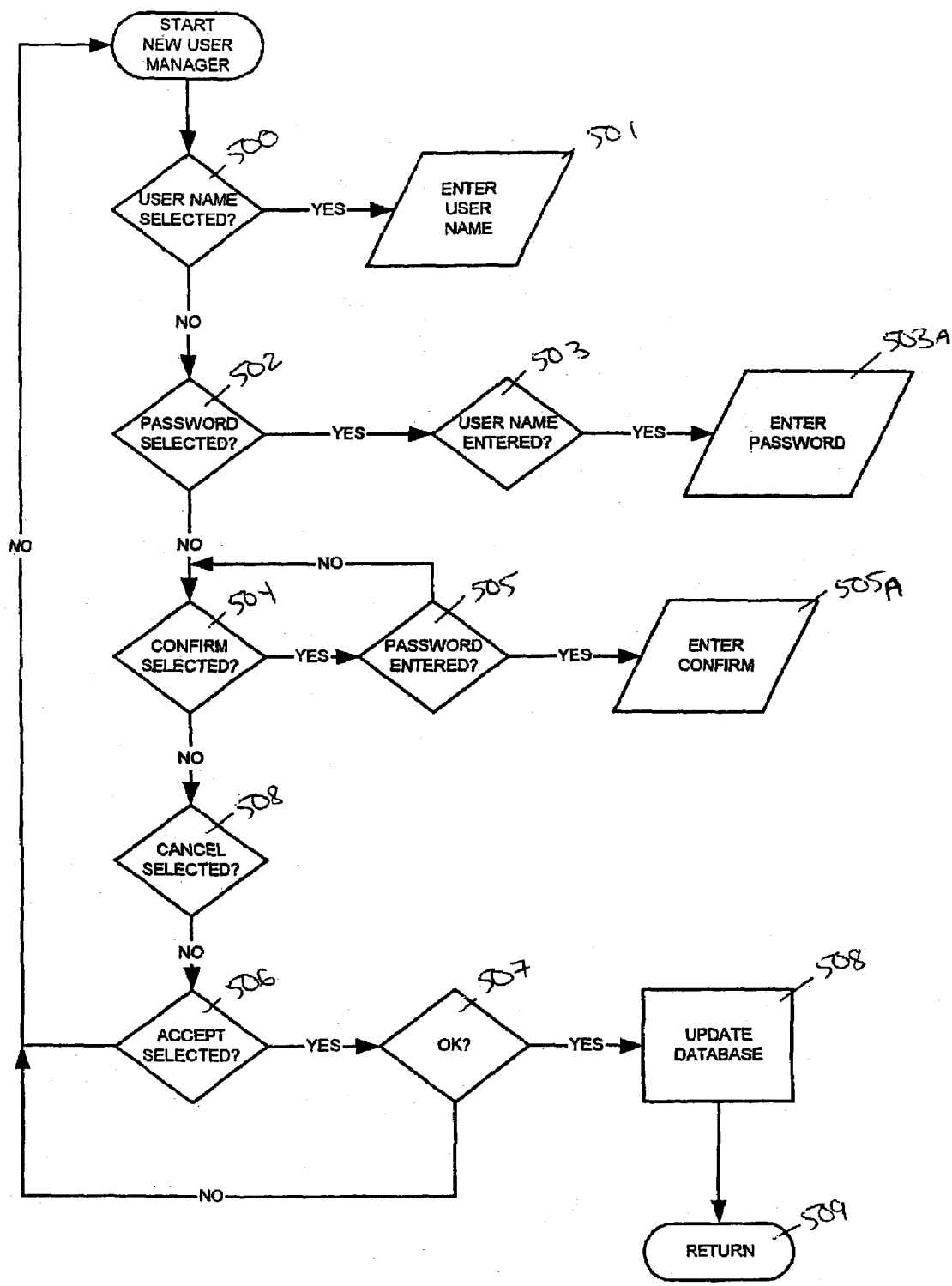

FIG. 6 present invention.

FIG. 7

Shows the project manager GUI according to the present invention.

FIG. 8

Shows the functional flow diagram for the project manager according to the present invention.

FIG. 9

Shows the new project manager GUI according to the present invention.

FIG. 10

Shows the functional flow diagram for the new project manager according to the present invention.

FIG. 11

Shows the host manager GUI according to the present invention.

FIG. 12

Shows the functional flow diagram for the host manager according to the present invention.

FIG. 13

Shows the model manager GUI according to the present invention.

FIG. 14

Shows the functional flow diagram for the model manager according to the present invention

FIG. 15

Shows the data manager GUI according to the present invention.

FIG. 16

Shows the functional flow diagram for the data manager according to the present invention.

FIG. 17

Shows the run manager input tab GUI according to the present invention.

FIG. 18–21

Shows the functional flow diagram for the run manager input tab according to the present invention.

FIG. 22

Shows the run manager output tab GUI according to the present invention.

FIG. 23–25

Shows the functional flow diagram for the run manager output tab according to the present invention.

FIG. 26

Shows the data set selection manager GUI according to the present invention.

FIG. 27

Shows the functional flow diagram for the data set selection manager according to the present invention.

FIG. 28

Shows the command file manager GUI according to the present invention

FIG. 29

Shows the functional flow diagram for the command file manager according to the present invention.

FIG. 30

Shows the new command file manager GUI according to the present invention

FIG. 31

Shows the functional flow diagram for the new command file manager according to the present invention.

FIG. 32

Shows the sortfun widget in the context of the new command file manager GUI according to the present invention.

FIG. 33

Shows the functional flow diagram for the sortfun widget according to the present invention.

FIG. 34

Shows the tabfun widget in the context of the new command file manager GUI according to the present invention

FIG. 35–36

Shows the functional flow diagram for the tabfun widget according to the present invention.

FIG. 37

Shows the rotfun widget in the context of the new command file manager GUI according to the present invention.

FIG. 38–39

Shows the functional flow diagram for the rotfun widget according to the present invention.

FIG. 40

Shows the trafun widget in the context of the new command file manager GUI according to the present invention.

FIG. 41

Shows the functional flow diagram of the trafun widget according to the present invention.

FIG. 42

Shows the fitfun widget in the context of the new command file manager GUI according to the present invention.

FIG. 43

Shows the functional flow diagram of the fitfun widget according to the present invention.

FIG. 44

Shows the model queue selection manager GUI according to the present invention.

FIG. 45

Shows the functional flow diagram of the model queue selection manager according to the present invention.

FIG. 46

Shows the new search model queue manager GUI according to the present invention.

FIG. 47

Shows the functional flow diagram of the search model queue manager according to the present invention.

FIG. 48

Shows the locations of the execution manager and the CCP4 manager in the layout of the computing cluster. The execution manager communicates over a LAN with the CCP4 manager. The CCP4 manager interfaces with the CCP4 program suite. The execution manager interfaces with the user on the master host via managers located in the main GUI.

FIG. 49–52

Shows the functional flow diagram of the execution manger according to the present invention.

FIG. 53–61

Shows the functional flow diagram of the CCP4 manager according to the present invention.

FIG. 62–68

Show database tables according to one embodiment of the present invention.

DETAILED DESCRIPTION OF THE PREFERRED EMBODIMENT

Main Manager

Figure 1:
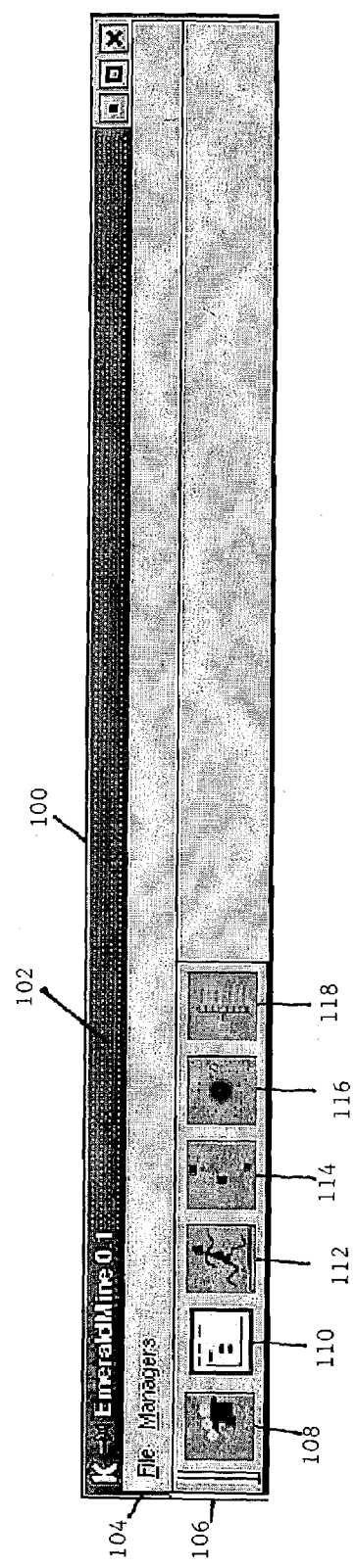
FIG. 1

FIG. 1 shows the top portion of the application window when the invention is first launched. The application window includes the main manager 100 which consists of a title bar 202, a menu bar 204, and unique pictographical buttons 206 representing each of the database managers. Included in the menu bar are a series of menu identifiers: File and Managers. Moving the cursor over a pictographical button displays the title of the unique button as well as the steps necessary for key acceleration. Clicking the appropriate button opens a database manager. The database managers include a user manager 108, a project manager 110, a run manager 112, a model manager 114, a reflection manager 116, and a host manager 118.

Figure 2:
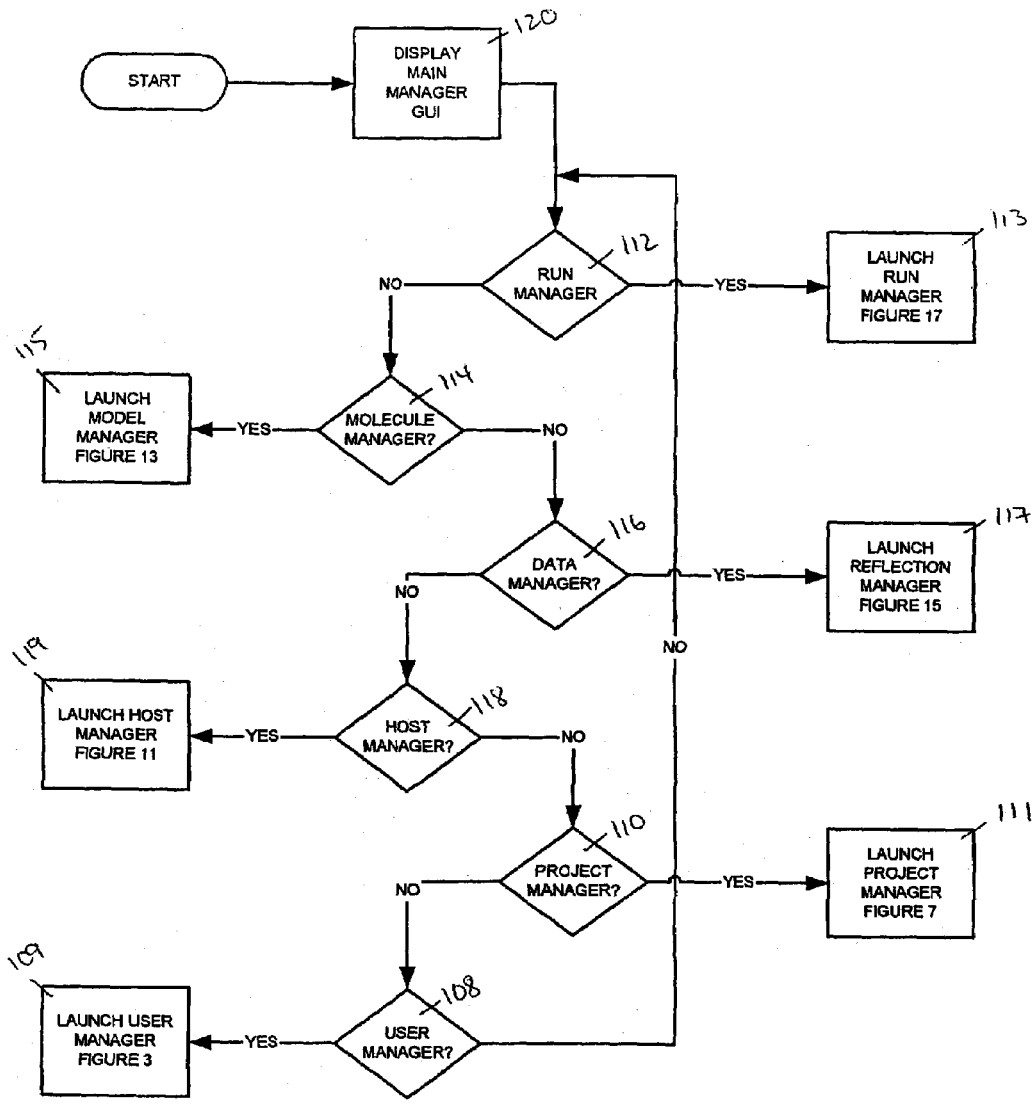

FIG. 2 diagrams the functional flow of the main manager. Selecting a button causes the corresponding database manager to be activated.

User Manager

Figure 3:
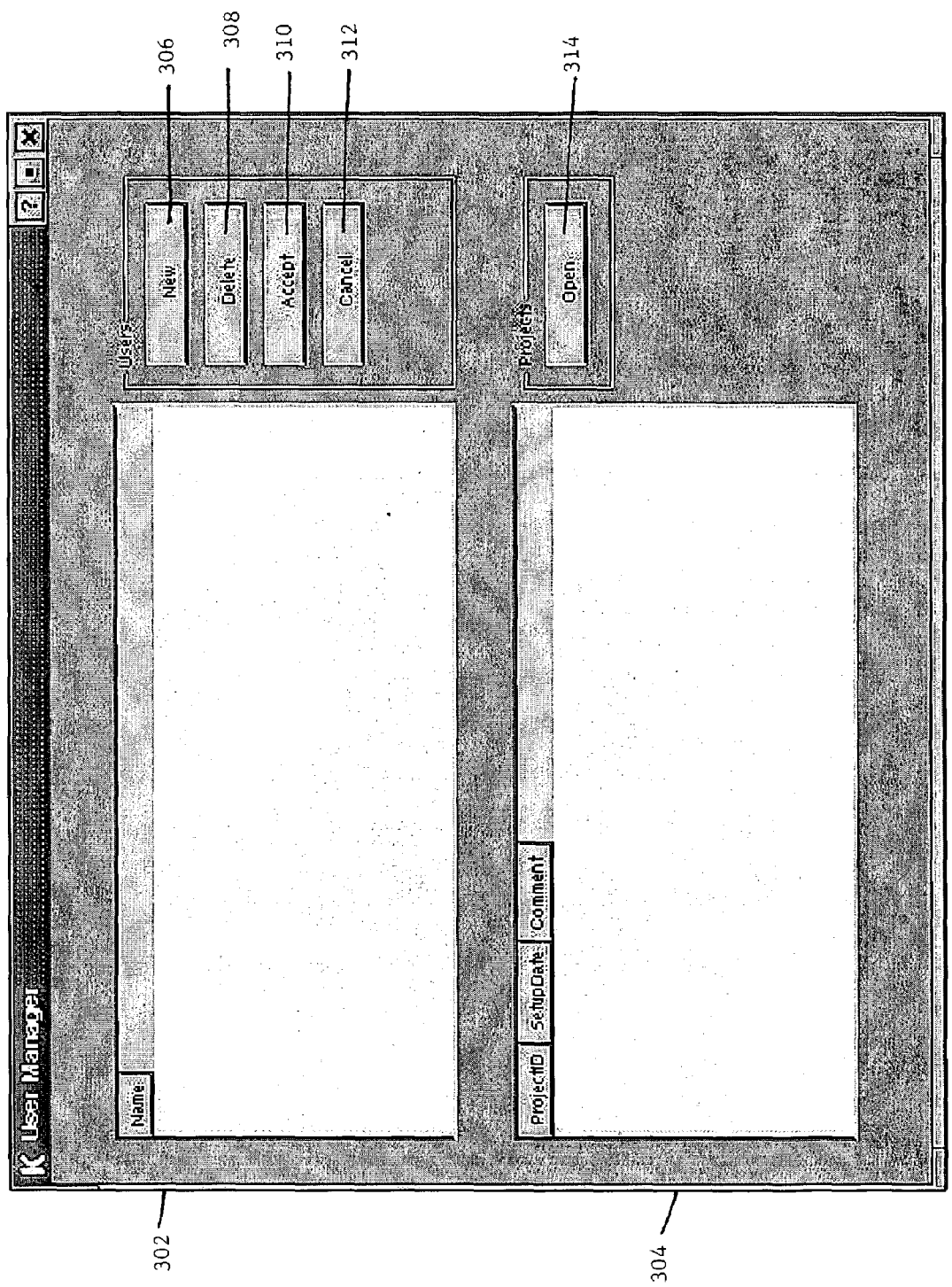
Figure 4:
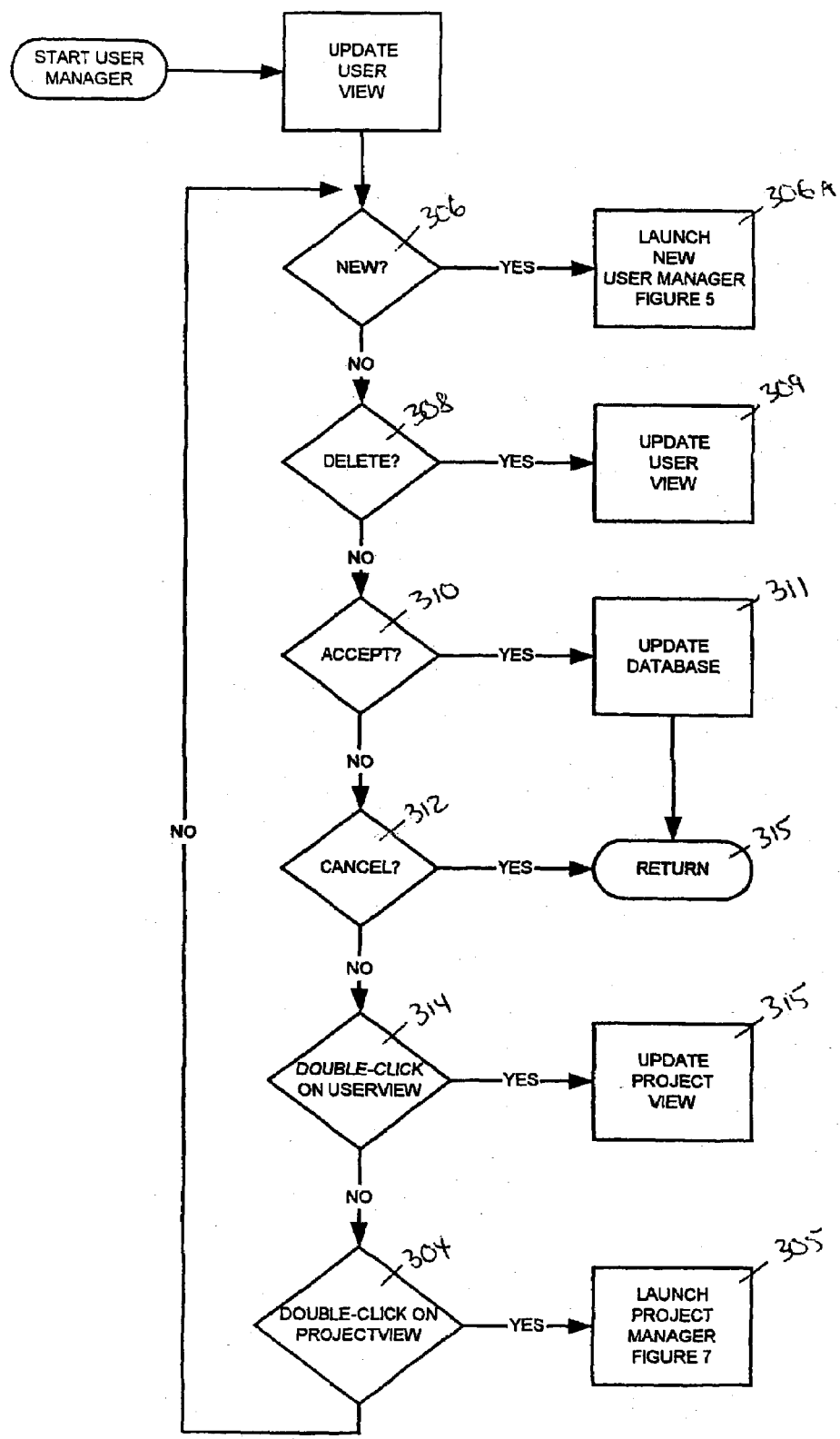
Figure 5:
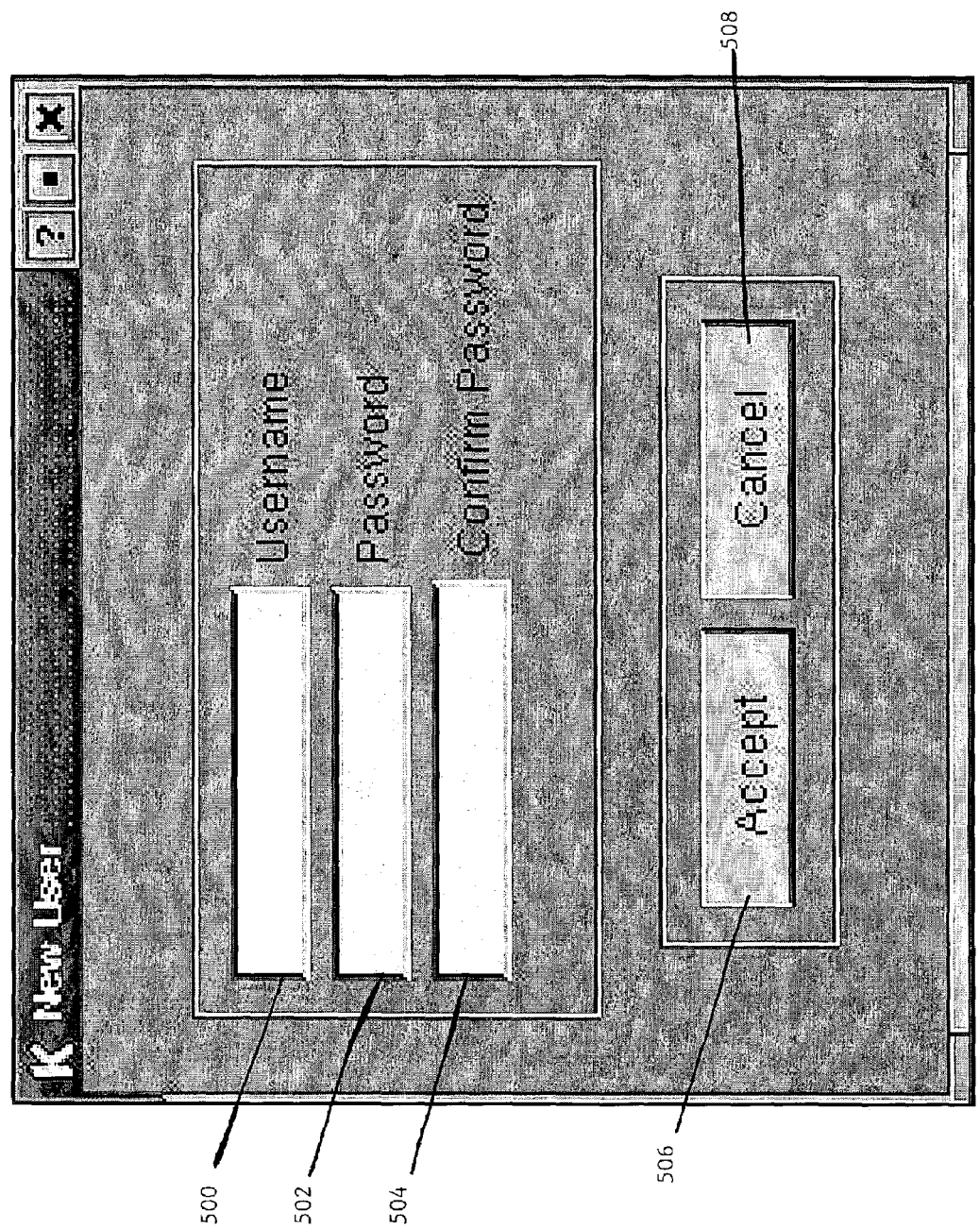

FIG. 3 shows the layout for the user manager. The manager includes a user list view 302 and a list view of projects 304 associated with a particular user. User information includes name and comment fields. Details of the project, including project ID, setup date and comment are displayed in the project view. Changes to the users may be implemented by selecting from the buttons. The buttons contain labels to provide useful information regarding their function. User choices include new 306, delete 308, accept 310, and cancel 312 buttons. Also included in the window is an open button 314 for the project list view. FIG. 4 shows the functional flow diagram of possible interactions with the user manager. When the window is first called, a list of users with access to the database is generated and presented in the user list view. Projects associated with a particular user can be displayed in the project list view by moving the cursor over a user entry and double clicking on the entry. This will cause the information in the project list view to refresh with the relevant information. This action is represented by steps 314 and 315 in FIG. 4. Additional users may be added to the contents of the user table by actuating the new button; a new user dialog window is launched, the GUI for which is shown in FIG. 5. This step is represented by step 306 in FIG. 4.

New User Manager

FIG. 5 shows the layout of the new user manager dialog. The manager contains text fields to enter the username 500 and password 502. The confirm password text field 504 is used to verify that the user has entered the password correctly. This action is represented by steps 500–505 of FIG. 6. The accept button 506 and the cancel button 508 are used by the user to finalize or abort the data entered. This action is represented by steps 506–509 of FIG. 6. The functional flow diagram in FIG. 6 shows that actuating either the accept or the cancel button cause the manager to exit and control is returned to the User Manager.

Project Manager

Figure 7:
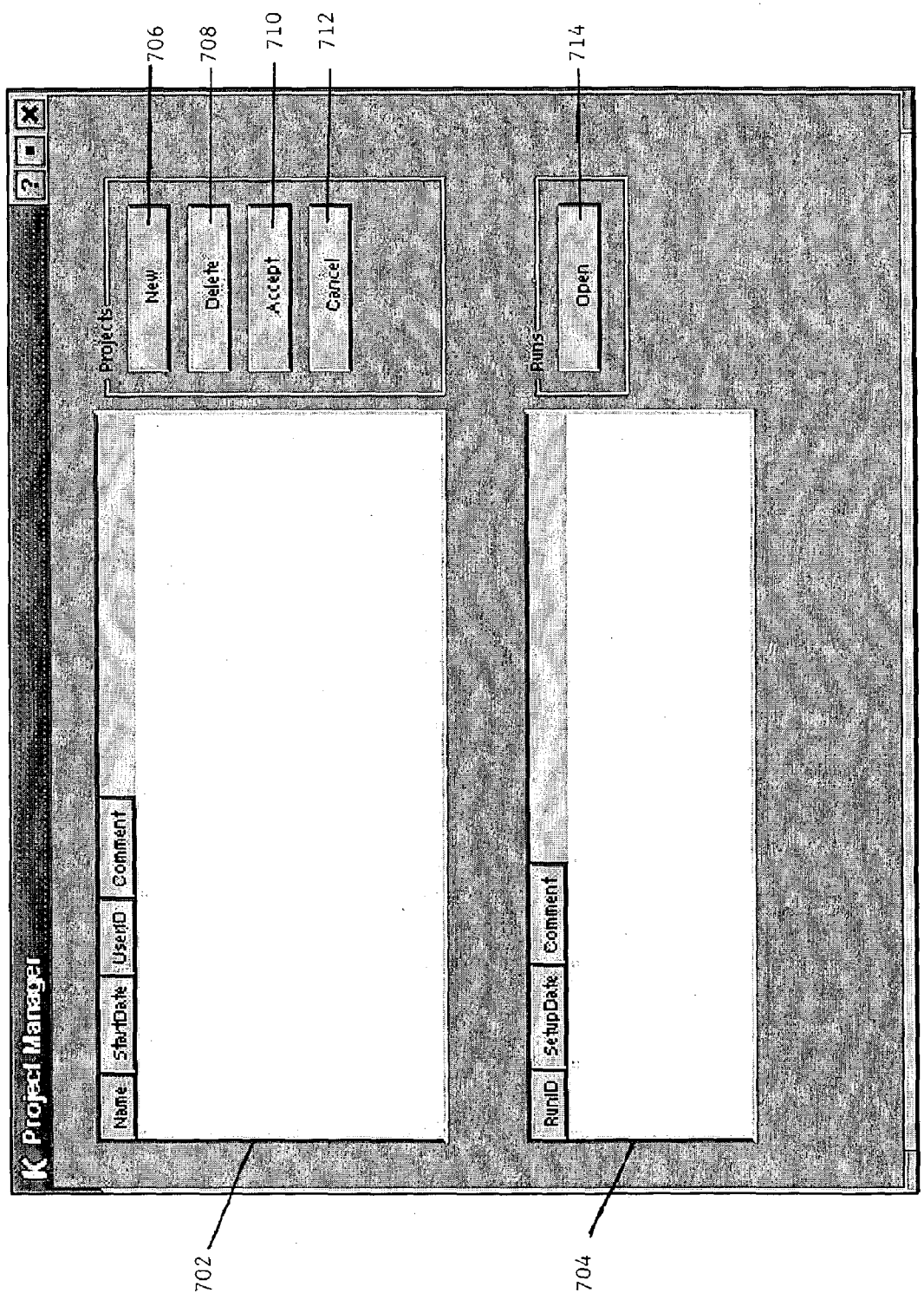
Figure 8:
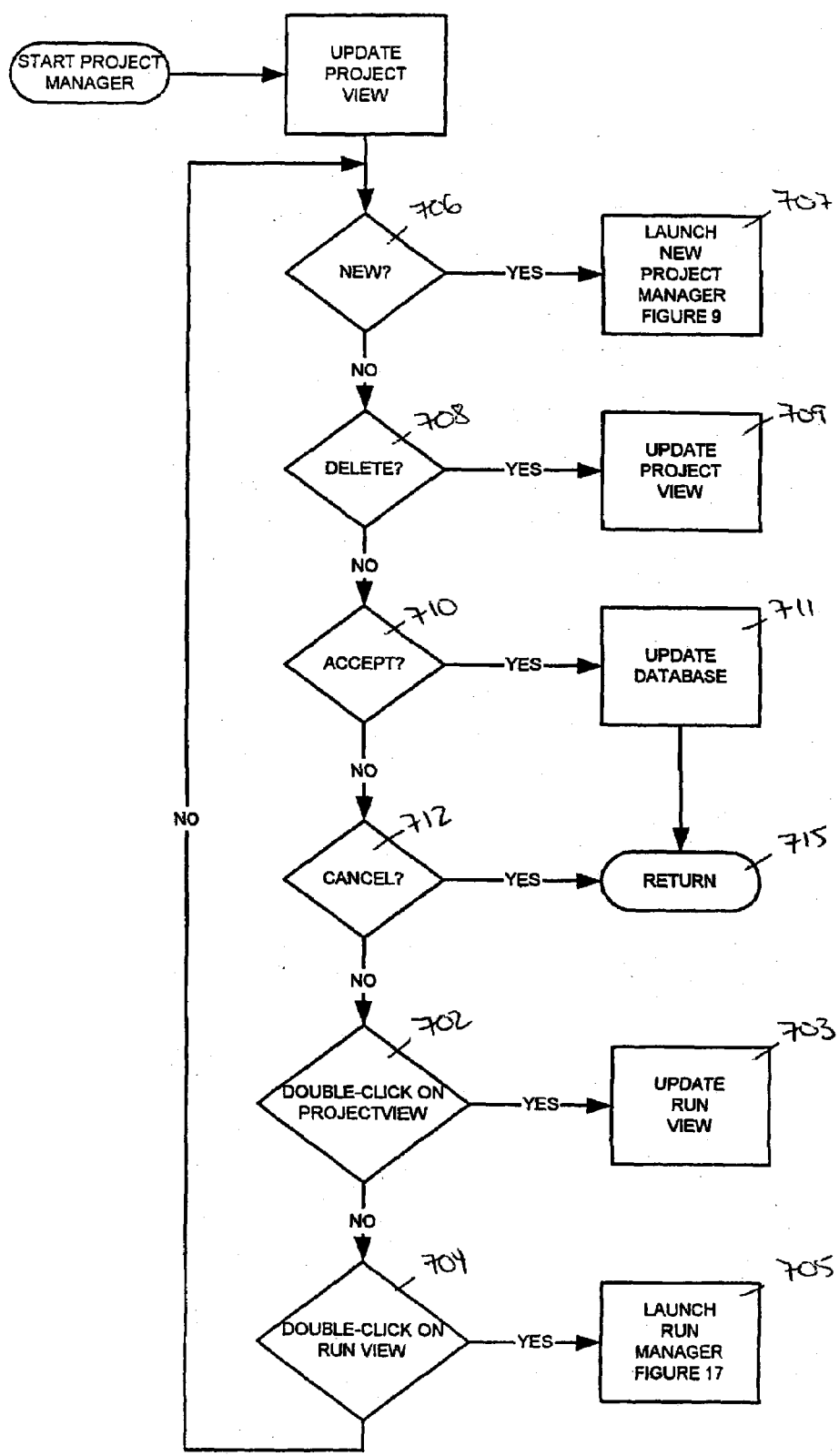
Figure 9:
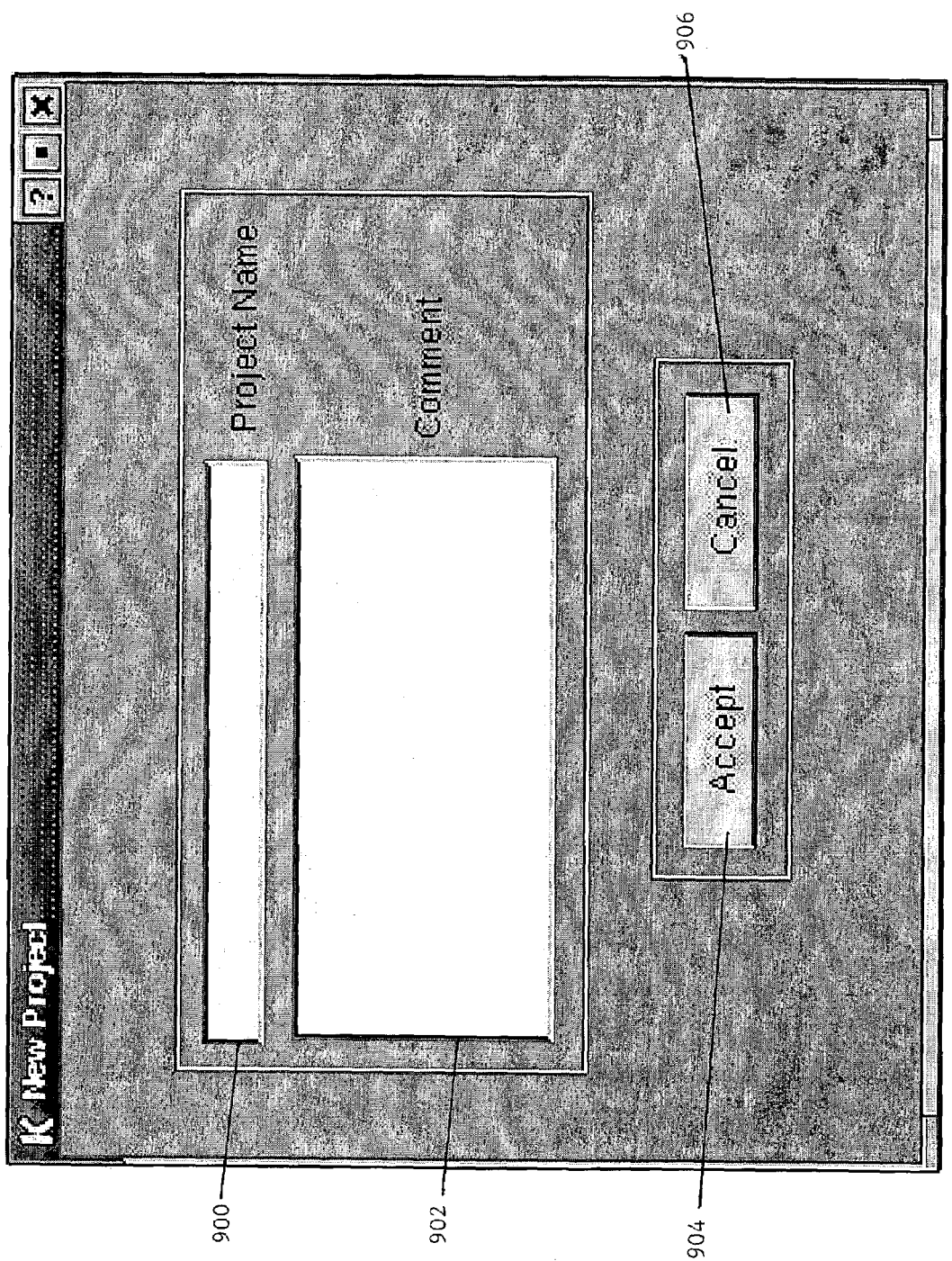

FIG. 7 shows the layout of the project manager. The manager includes a project list view 702 and a list view of runs 704 associated with a particular project. Project information includes name, start date, user, and comment fields. Details of the runs associated with a project, including run ID, setup date and comment are displayed in the run view. Changes to the projects may be implemented by selecting from the buttons. The buttons contain labels to provide useful information regarding their function. User choices include new 706, delete 708, accept 710, and cancel 712 buttons. Also included in the window is an open button 714 for the run list view. FIG. 4 shows the functional flow diagram of possible interactions with the user manager. When the window is first called, a list of projects is presented in the project list view. Runs associated with a particular project can be displayed in the run list view by moving the cursor over a project entry and double clicking on the entry. This will cause the information in the run list view to refresh with the relevant information. Additional projects may be added to the contents of the project table by actuating the new button; a new project dialog window is launched, the GUI for which is shown in FIG. 9.

New Project Manager

Figure 10:
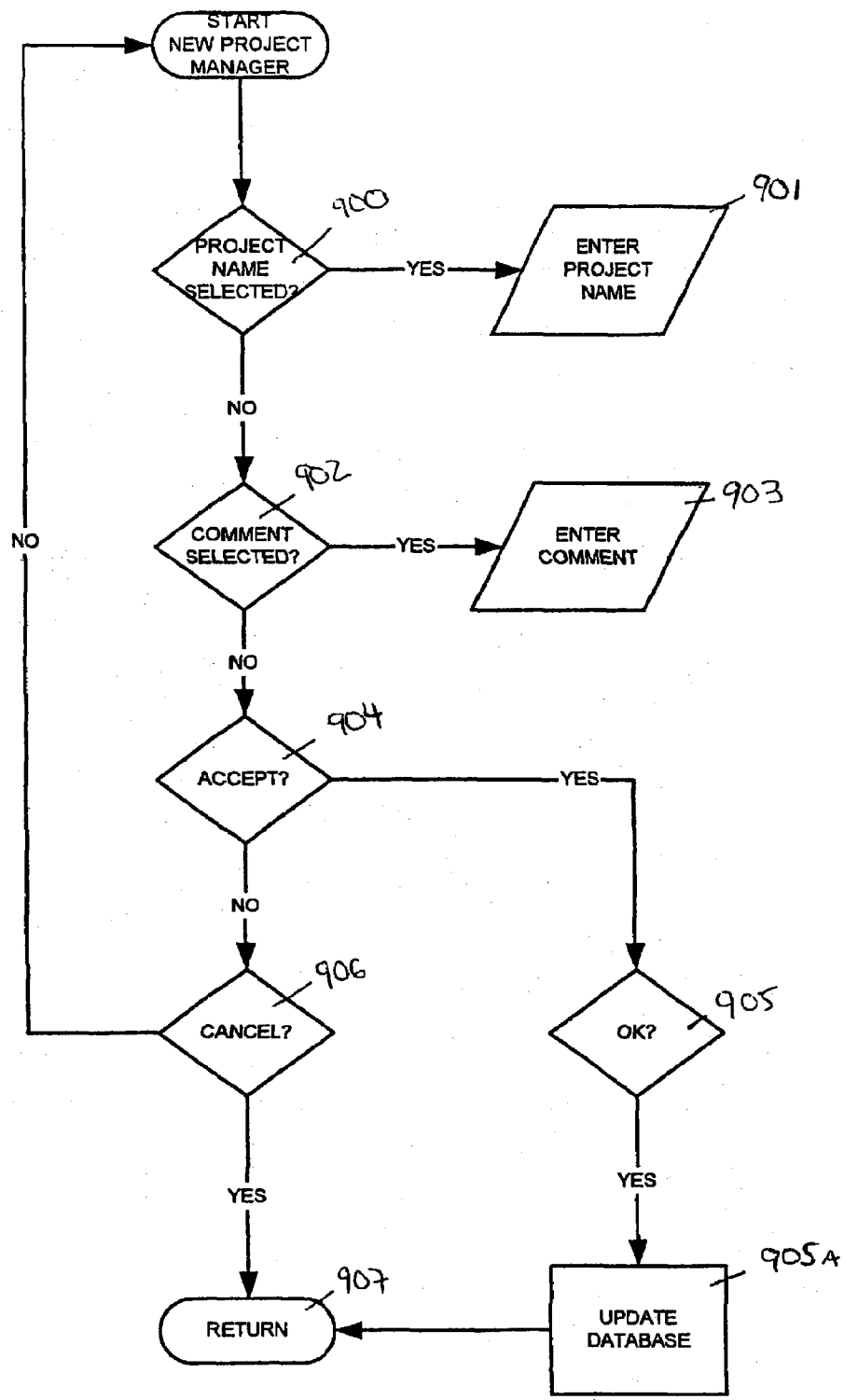

When the New project button is pressed from the project manager (FIG. 7), a dialog window is opened and a new project may be defined by the user. The new project manager includes a text box to enter a project name 900 and a multi-line text field 902 to enter any comments the user might want to associate with the project. An accept button 904 and a cancel button 906 allow the user to finalize or cancel the data entered in the new project manager. The actions precipitated by manipulating the buttons of the new project manager are represented by the functional flow diagram in FIG. 10.

Host Manager

Figure 11:
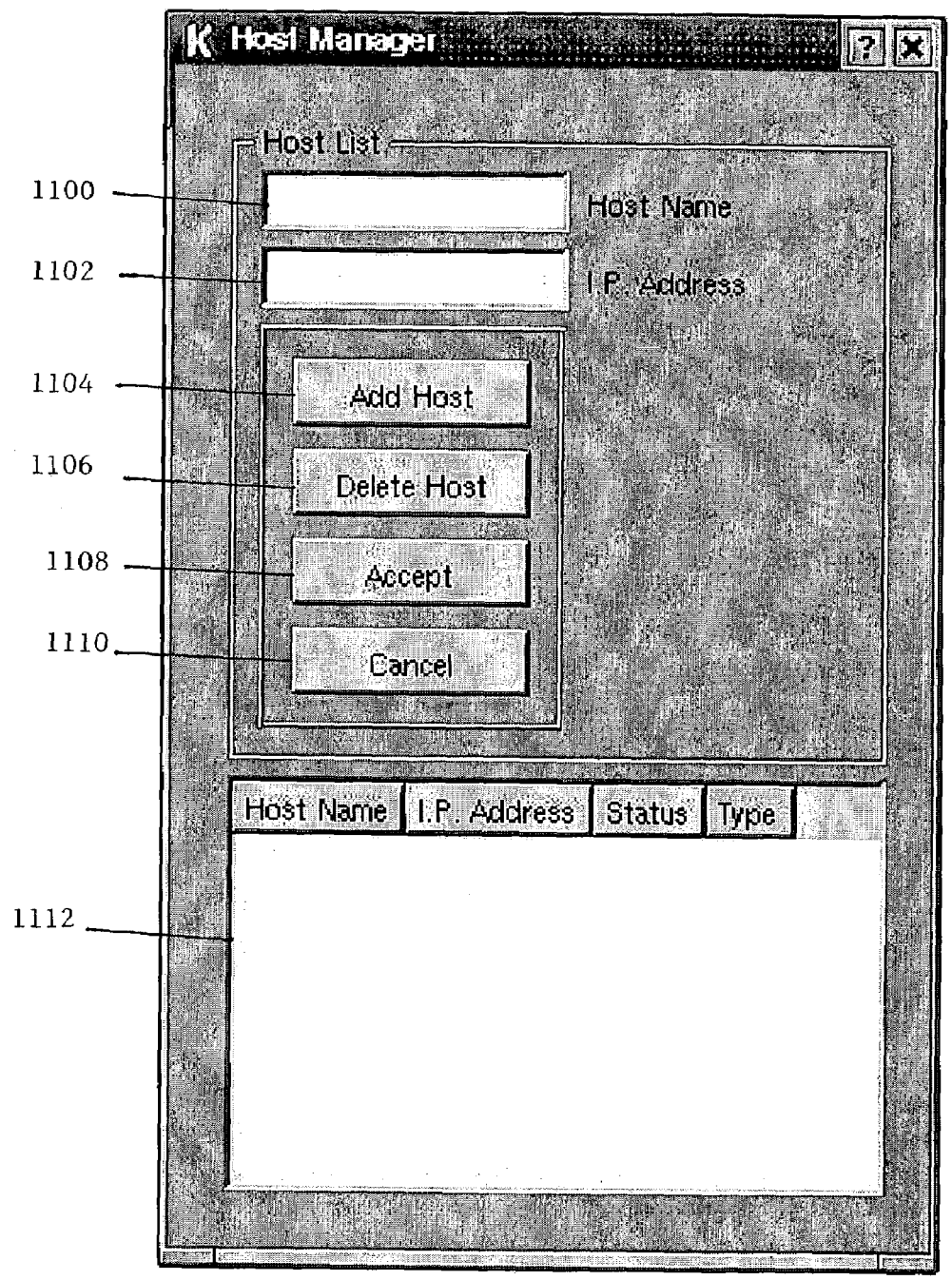
Figure 12:
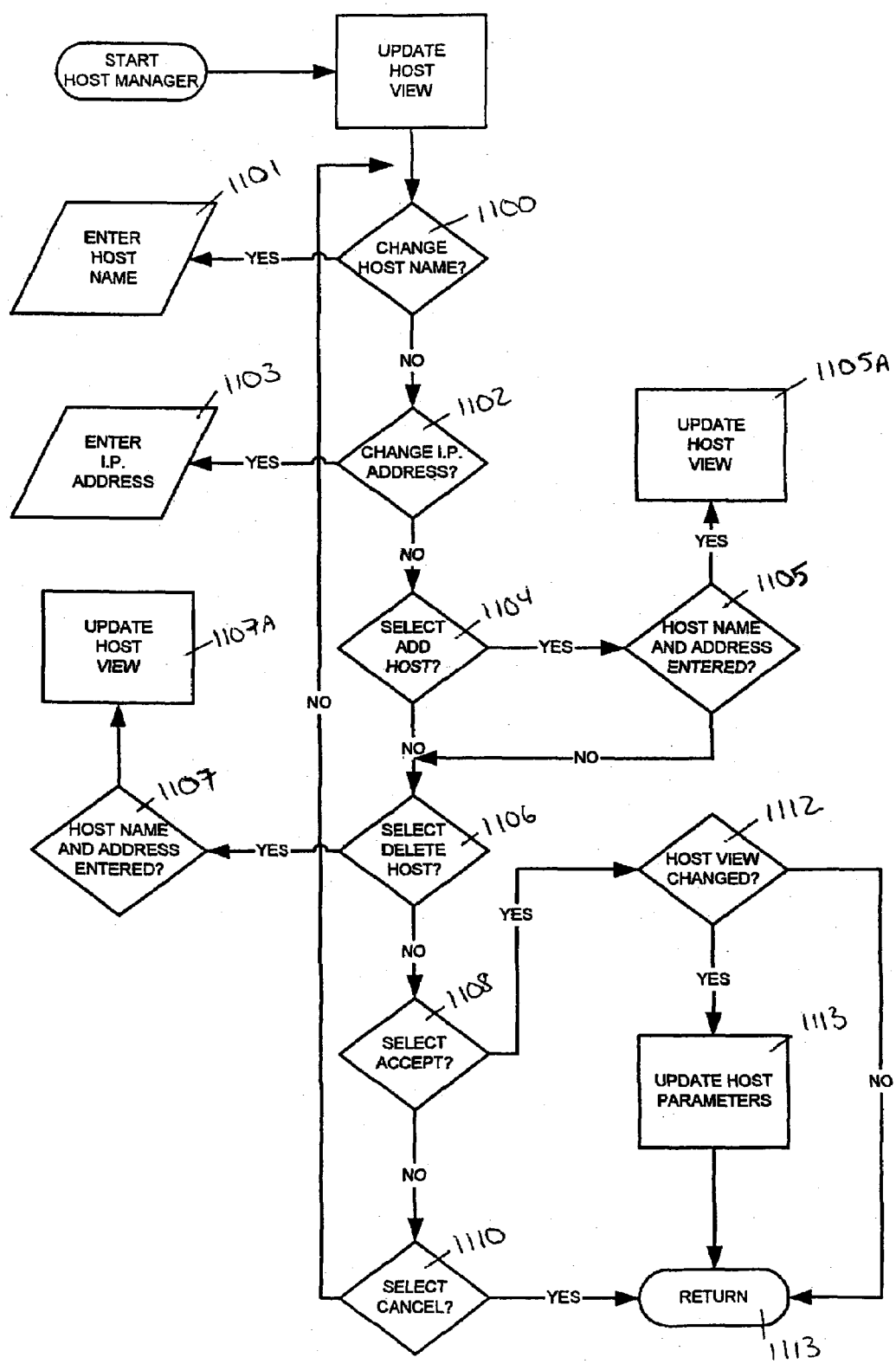
Figure 17:
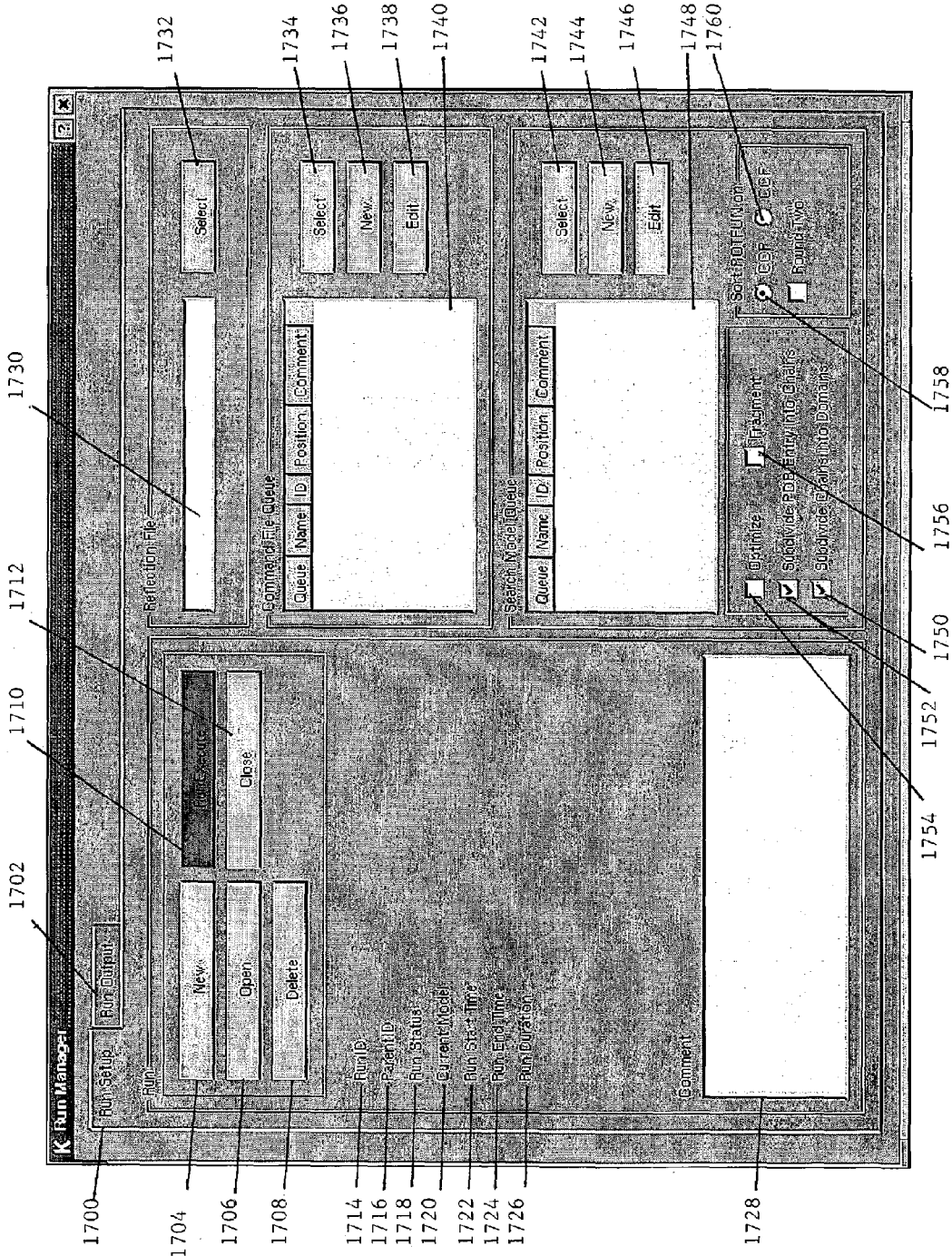
Figure 18:
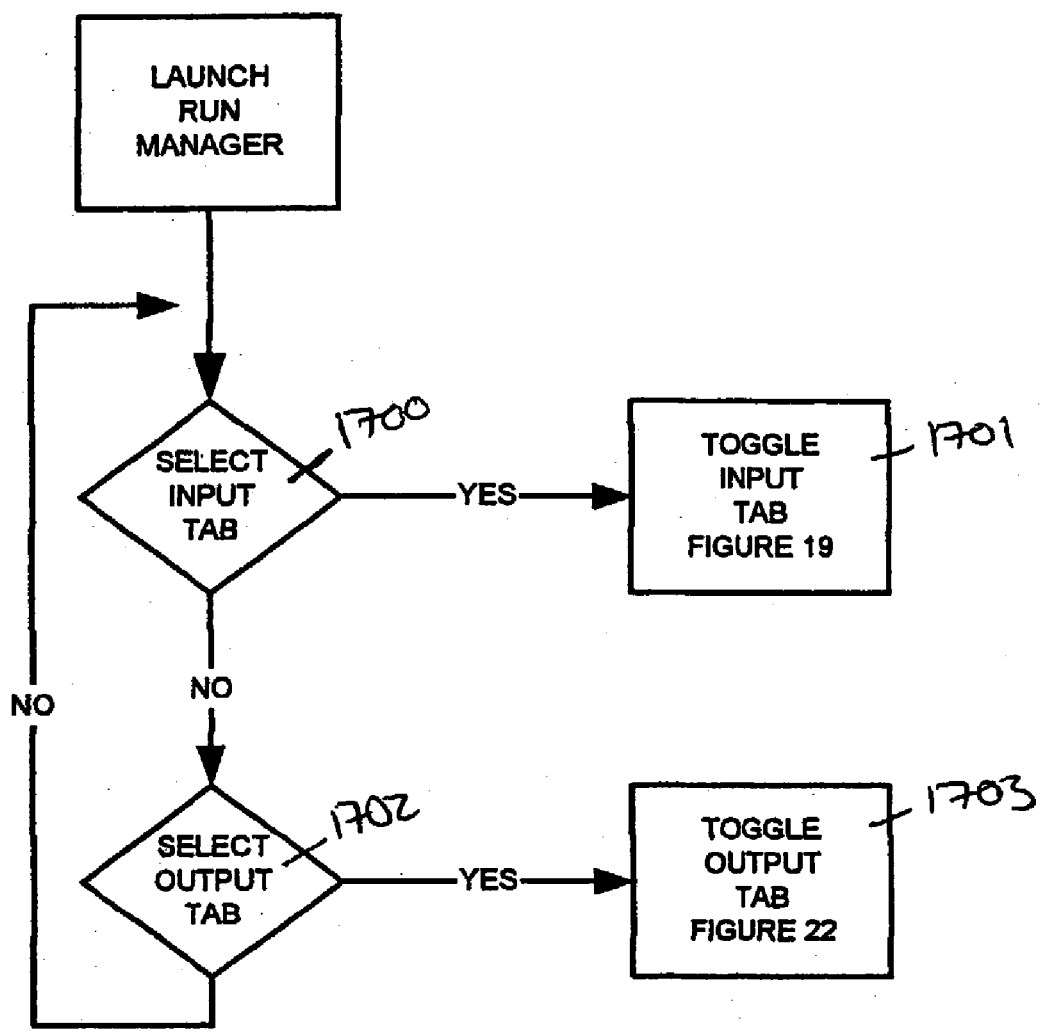
Figure 19:
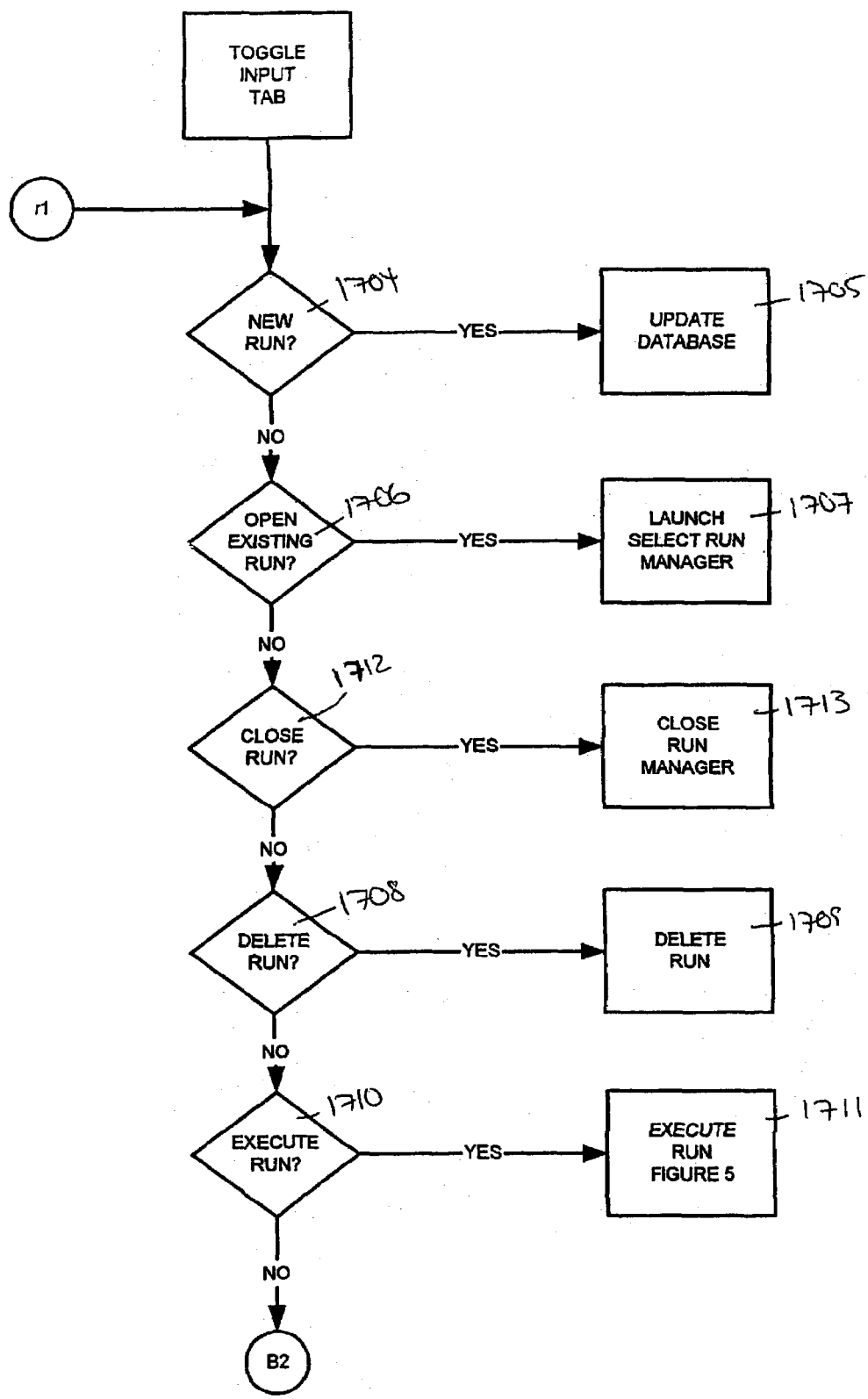
Figure 20:
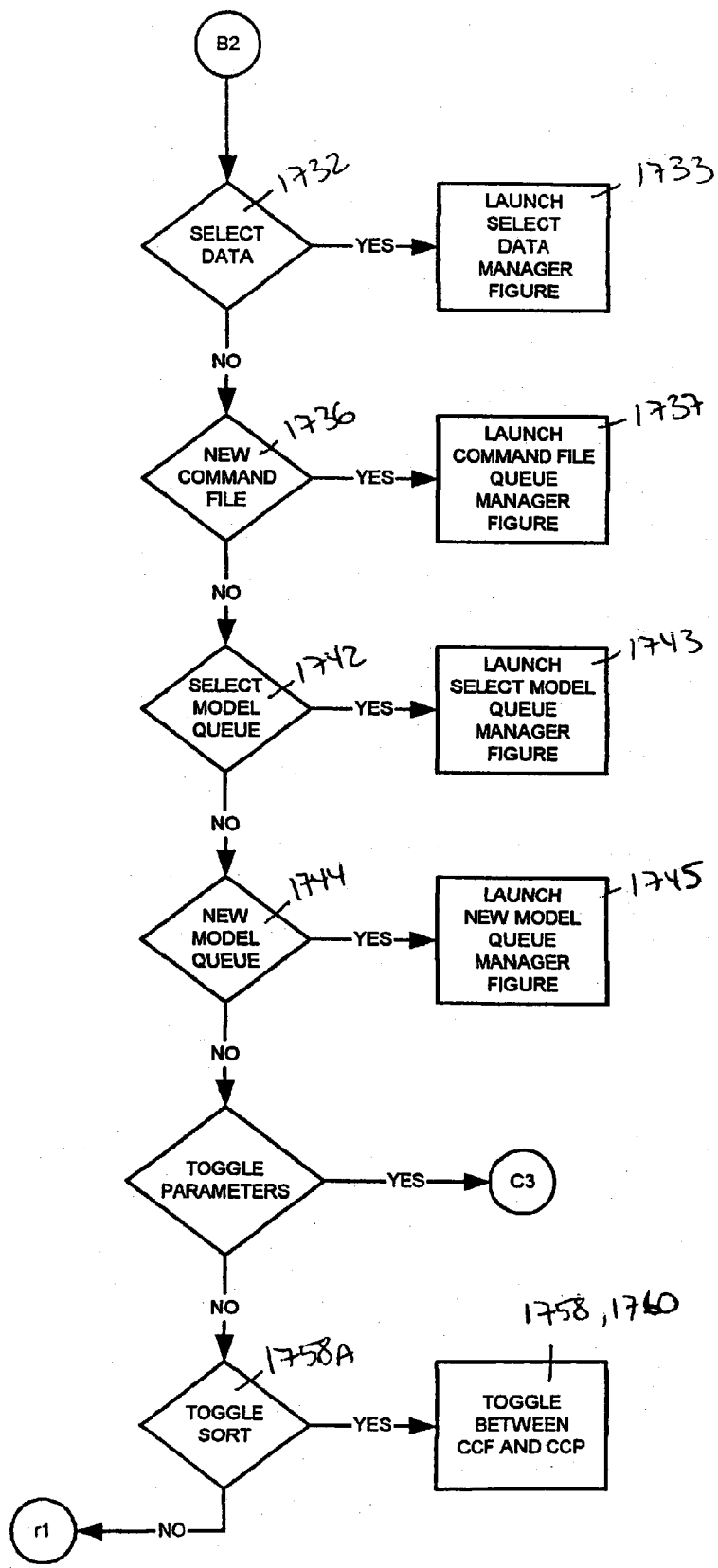
Figure 21:
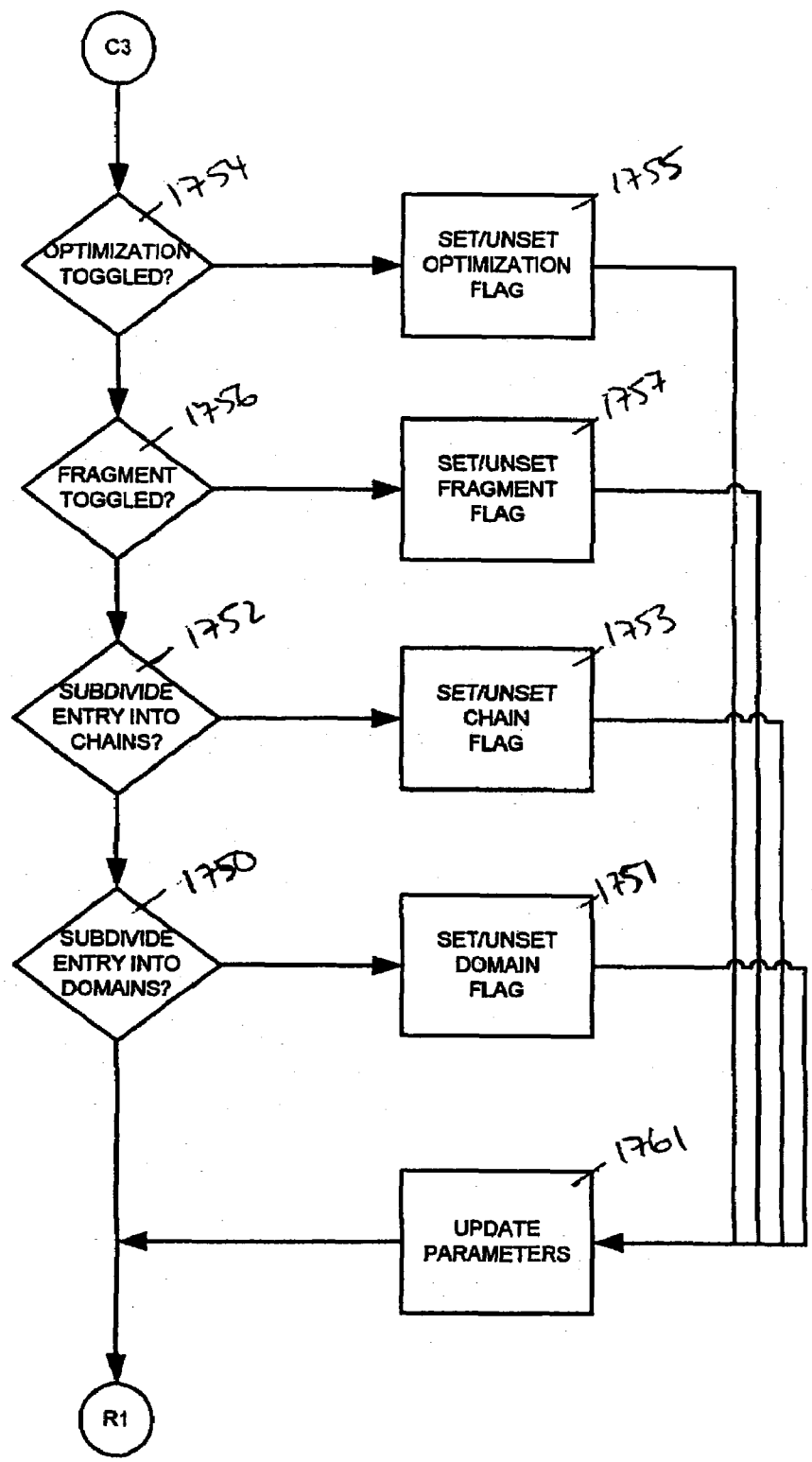
Figure 22:
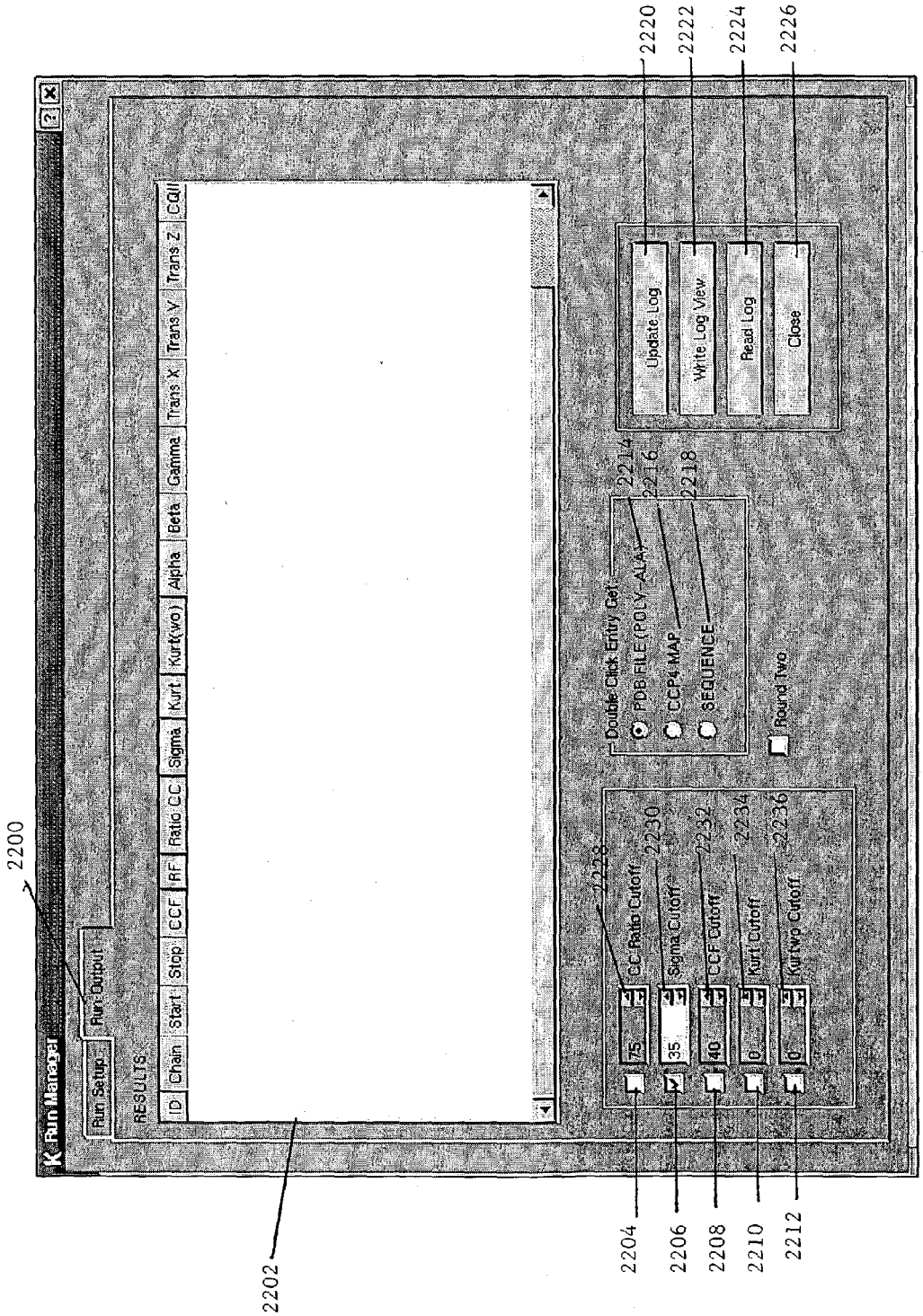

FIG. 11 shows the contents of the dialog window when the host manager button 118 is pressed and a host manager dialog window is launched. The manager contains text fields to enter host parameters and includes a hostname text field 1100 and IP address text field 1102. As shown in the functional flow diagram (FIG. 12), parameters entered into the hostname and IP address fields are displayed in the host list view 1112 by clicking on the add host button 1104. At any point, the user has the option to delete a host from the queue by selecting the host in the host view and pressing the delete host button 1106. This action is represented by steps 1106–1107 of FIG. 12. Once a list of hosts has been compiled the user has the option to accept the displayed list as the final host choice by clicking on the accept button 1108 or to abandon any modifications made to the host queue by pressing the cancel button 1110. Once the queue has been accepted the program stores the active list in memory for later execution from the run manager (FIG. 17). If the host manager is opened during the course of a run, the operational host list is recalled and displayed in the host list view along with current status of the machine and the type of machine (either Linux/Unix or Windows). Modifications (add and delete) cannot be made to the host queue if a run is in the process of executing.

Model Manager

Figure 13:
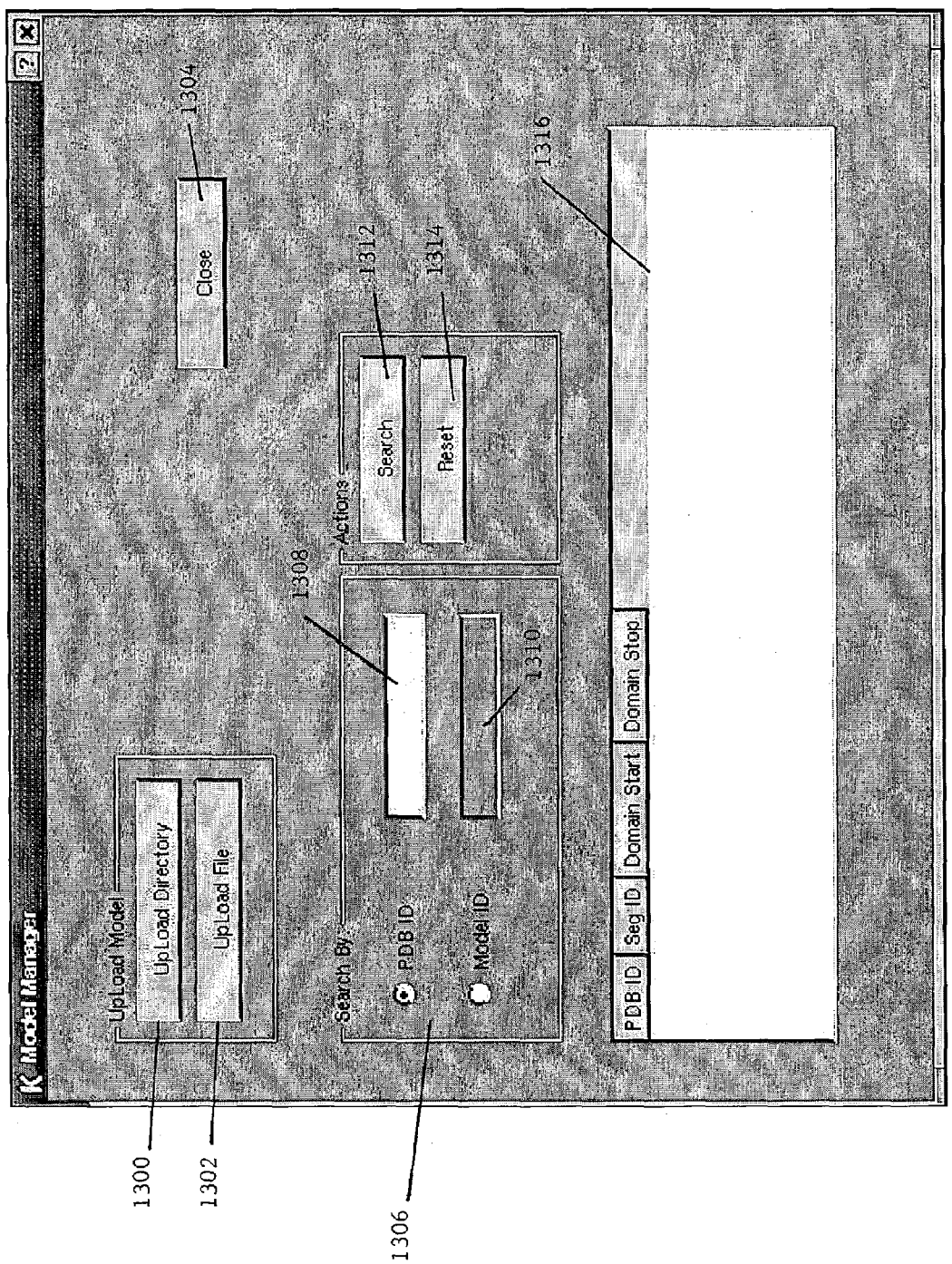

FIG. 13 show the widgets associated with the model manager. A user has the choice of uploading model coordinates singly or as a directory using the upload file button 1300 or the upload directory button 1302. The coordinates are preferably in a Brookhaven File format. At the very minimum the file must include a header providing the Protein Data Bank Identifier (PDB ID), the unit cell parameters, the space group, and a list of atom coordinates. Additionally, the user is prompted for the location of the latest SCOP (Structural Classification of Proteins) release [16]. The file is used to determine the number of protein chains associated with a molecule, the domain boundaries of the protein molecule. When proteins are loaded into the database they are also classified according to the uniqueness of the fold. Three categories are established by the invention using the information from SCOP: structures with greater than 90% sequence homology, structures with less than 90% sequence homology and structures with less than 25% sequence homology. These categories are used to limit redundancies in the search model queue.

Figure 14:
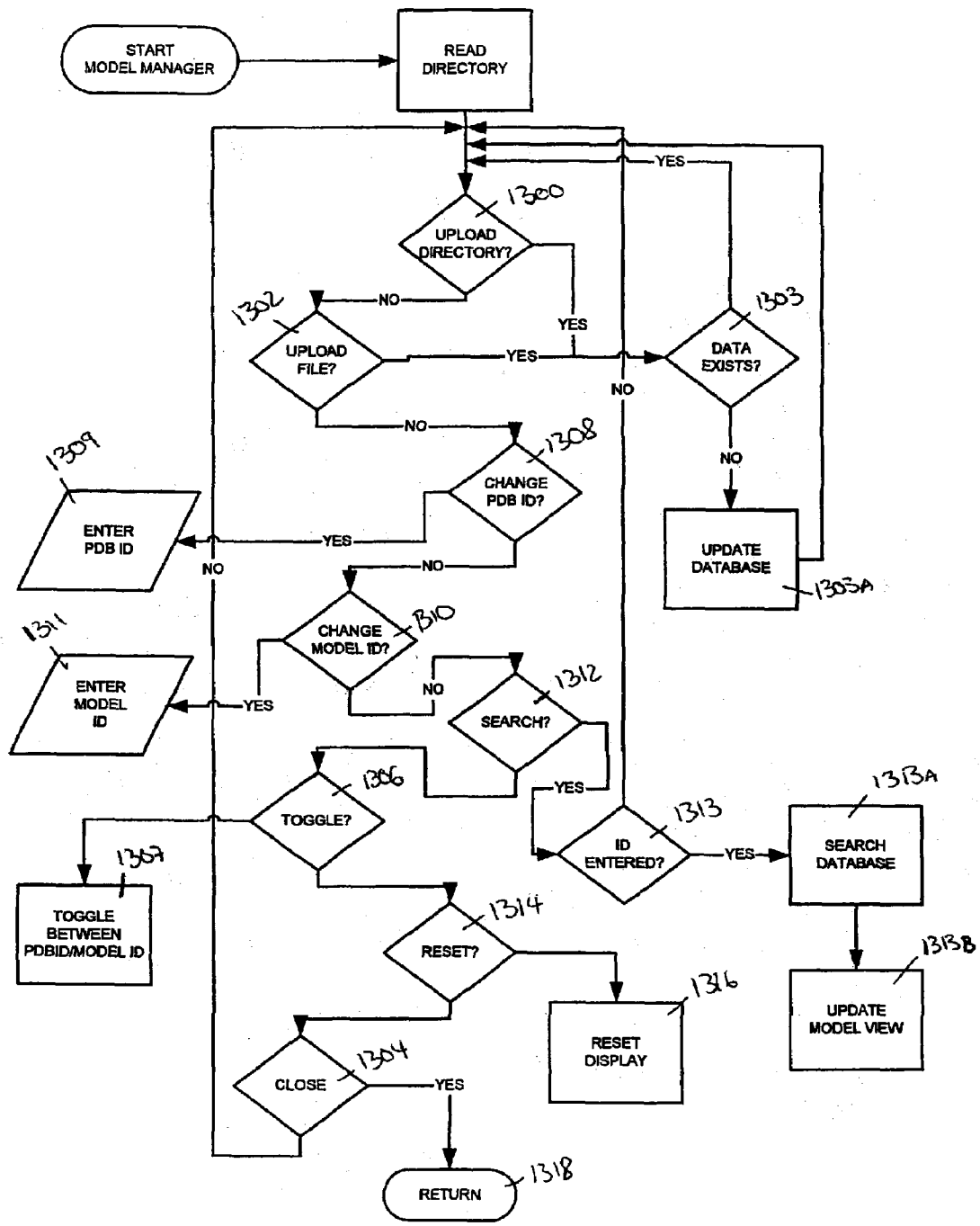

Any model may be uploaded into the database including protein molecules and small molecule compounds. According to the functional flow diagram in FIG. 14, the file is uploaded to the database only if the coordinates don't already exist in the database. This is achieved by comparing the PDB ID of the file with PDB IDs currently stored in the database. Pressing the search button 1312 allows the user to query the database for a particular PDB ID or model ID. This action is represented by steps 1312–1313 of FIG. 14. A choice between the two types of IDs can be made by toggling between the PDB ID radio button or the Model ID radio button 1306. This action is represented by steps 1306–1307 of FIG. 14. These buttons in turn enable/disable the corresponding PDB ID text field (1308 and 1310). The value entered into the text fields is used to search the database and the results are displayed in the model list view 1316. The results of the query include the PDB identifier, the segment name(s), and the boundaries of any domains contained within the model. The queries are accumulated in the list view until the reset button 1314 is pressed at which point the list view is cleared of all entries.

Reflection Manager

Figure 15:
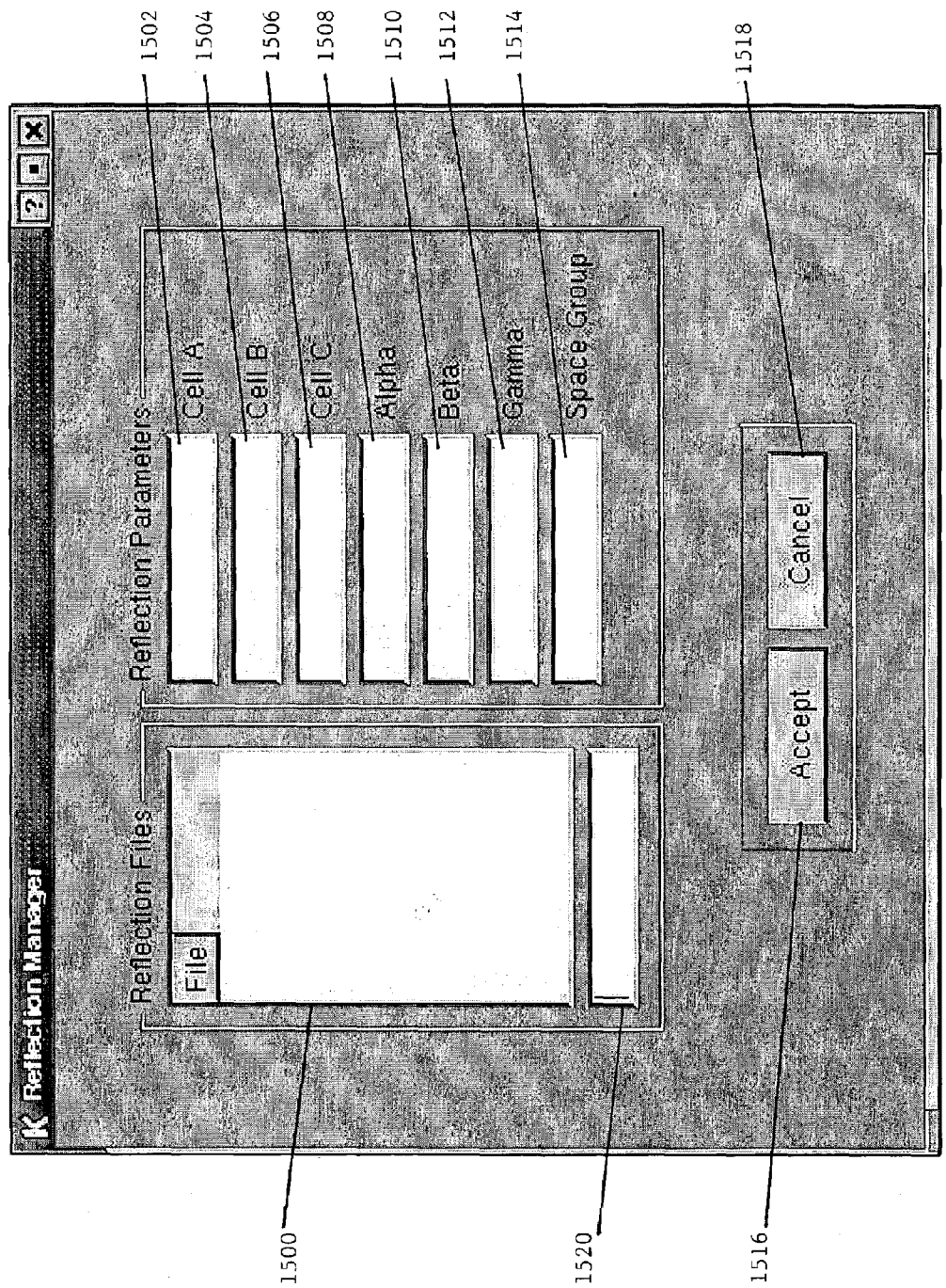
Figure 16:
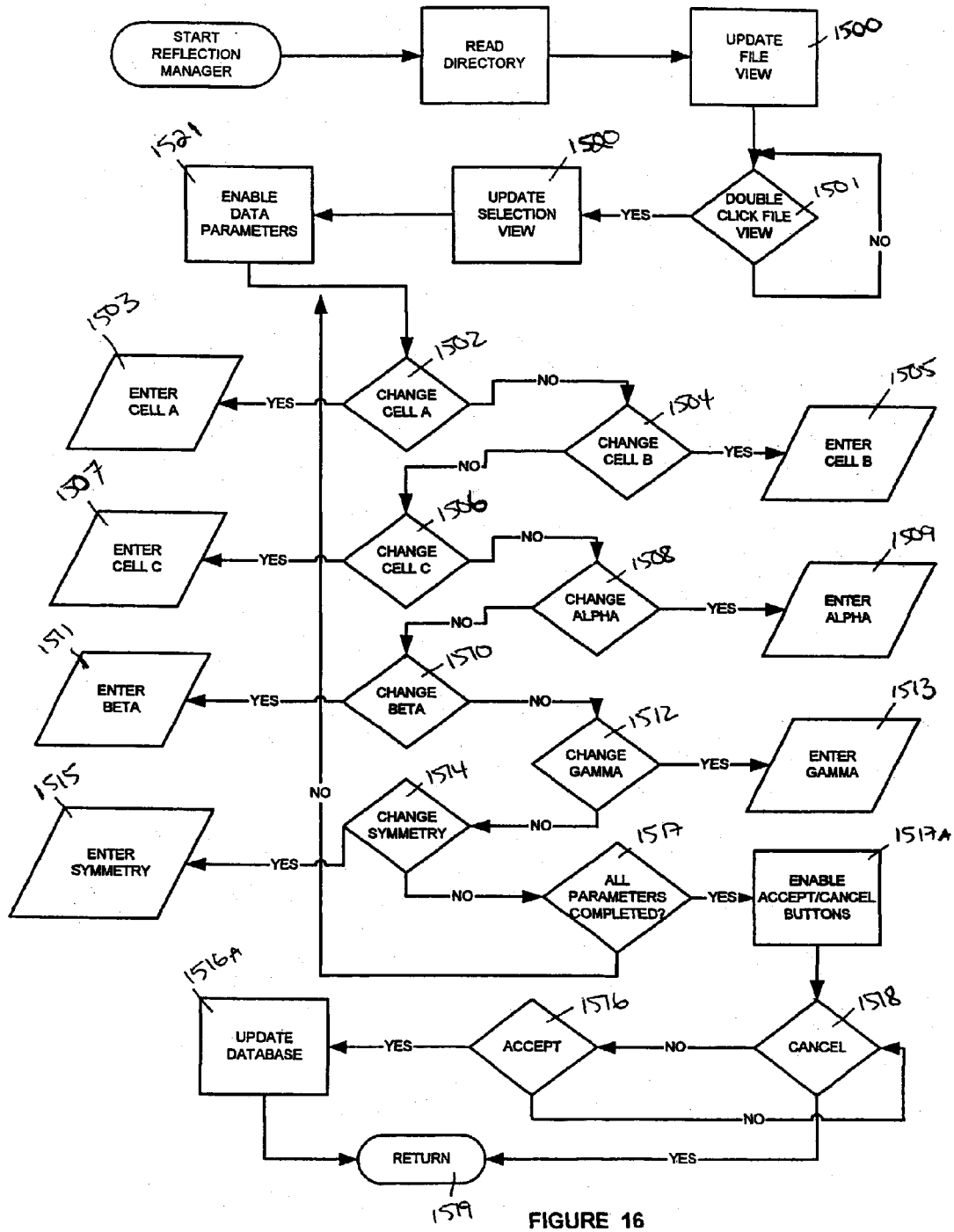

The database can be populated with reflection data sets from the reflection manager shown in FIG. 15. The reflection manager GUI consists of text fields for entering cell dimensions (1502, 1504, 1506) and cell angles (1508, 1510, 1512), as well as a field for entering the space group of the data set. When the manager is first activated, a scan is made of the default working directory for files with the appropriate suffix (.fin). The reflection file must be in ASCII (American Standard Code for Information Interchange) format. The files are listed in the data list view 1500 according to file name. As shown in the functional flow diagram in FIG. 16 (steps 1500, 1501, 1520), the user may select a file to upload by clicking on the entry in the list view. The name of the selected entry will appear in the selection text field 1520. Once the reflection is selected by the user, parameters that describe the reflection data are entered using the text fields for cell dimensions, cell angles, and space group. This action is represented by steps 1502–1515 and 1517 of FIG. 16. The selection is finalized and the file is uploaded by pressing on the accept button 1516. The upload procedure may be aborted by selecting the cancel button 1518.

Run Manager

Figure 23:
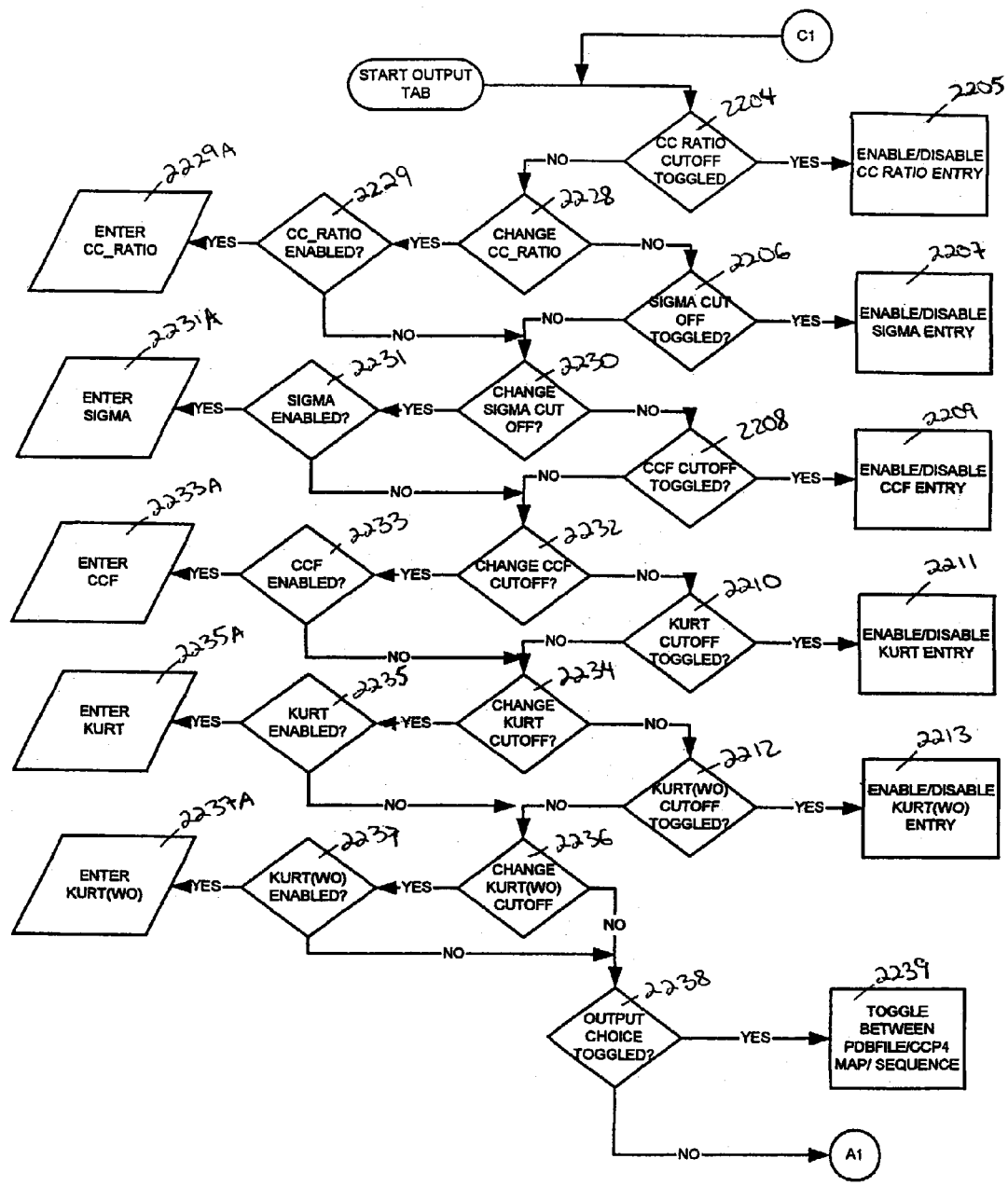
Figure 24:
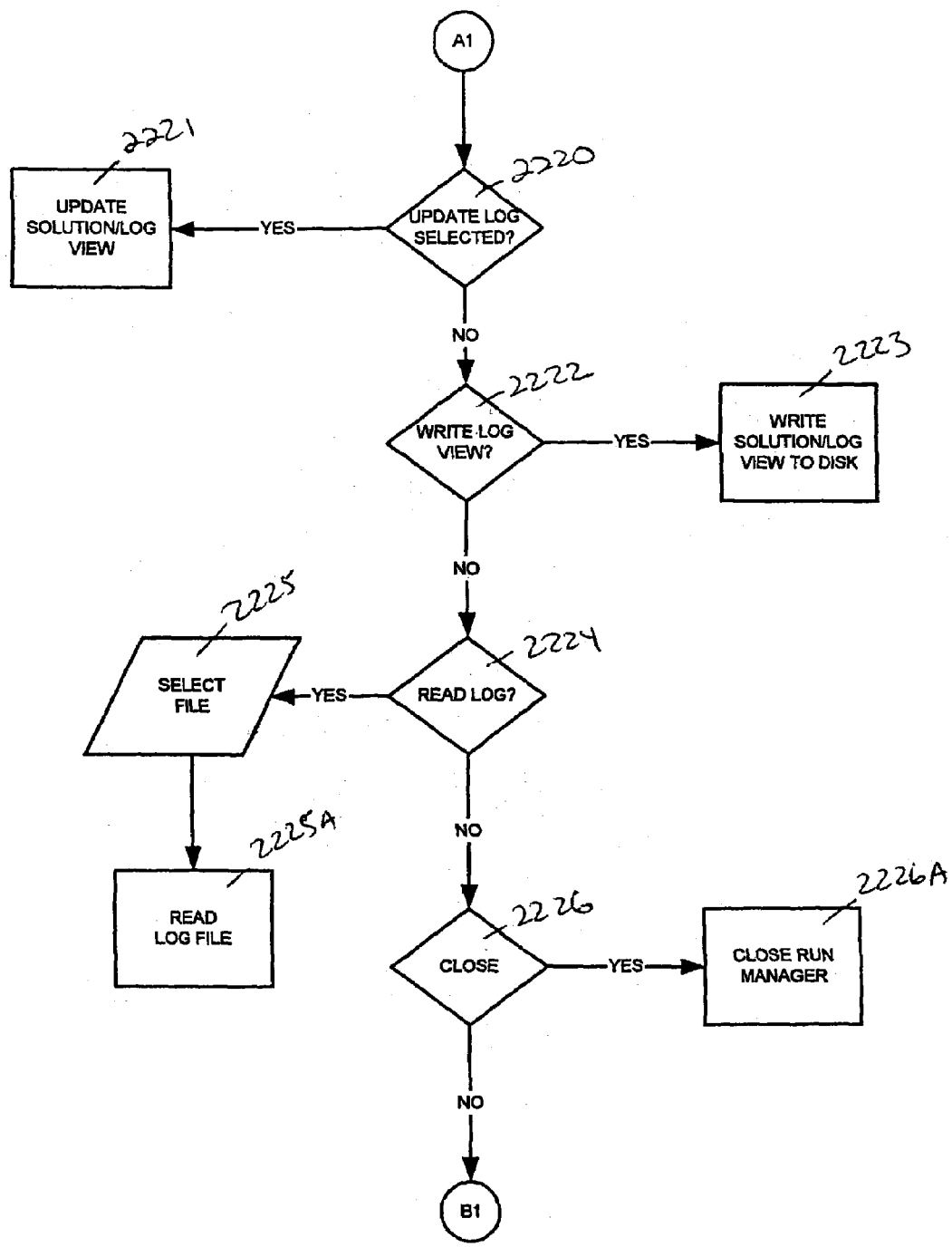
Figure 25:
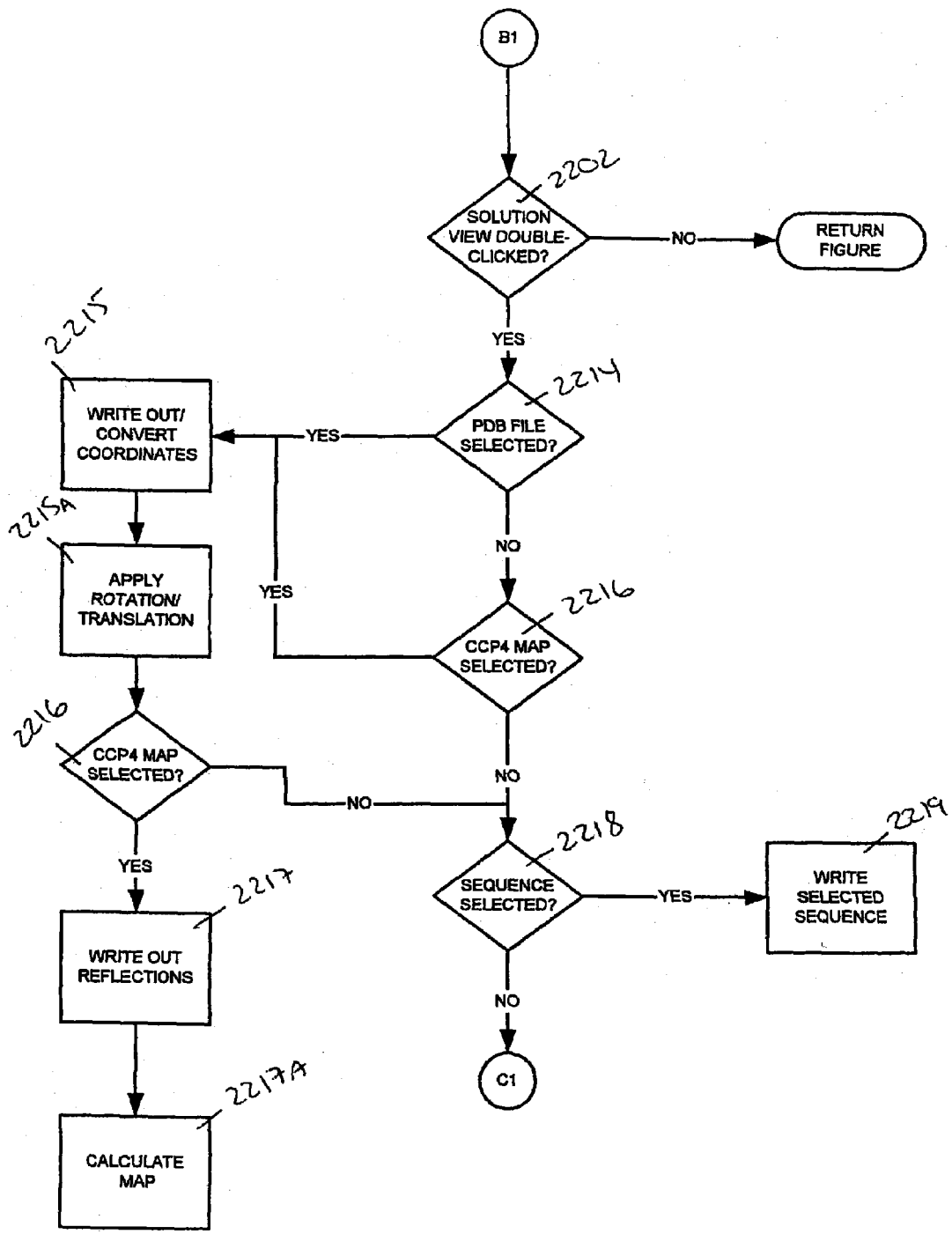

The run manager is the core of the invention. The run manager is activated directly by pressing the run manager button 112 from the main manager or indirectly through the project manager dialog (FIG. 7). The run manager dialog consists of two tab windows: a run setup tab 1700 and a run output tab 1702. The run input tab controls all the parameters required for the execution of molecular replacement searches, while the output tab allows users to review the results from molecular replacement searches. The functional flow diagram in FIGS. 18–21 describes the way in which a run may be initiated and executed via the run input tab. The functional flow diagram in FIGS. 23–25 describes the way in which output from the run may be viewed via the run output tab.

RunManager: Run Input Tab

Figure 26:
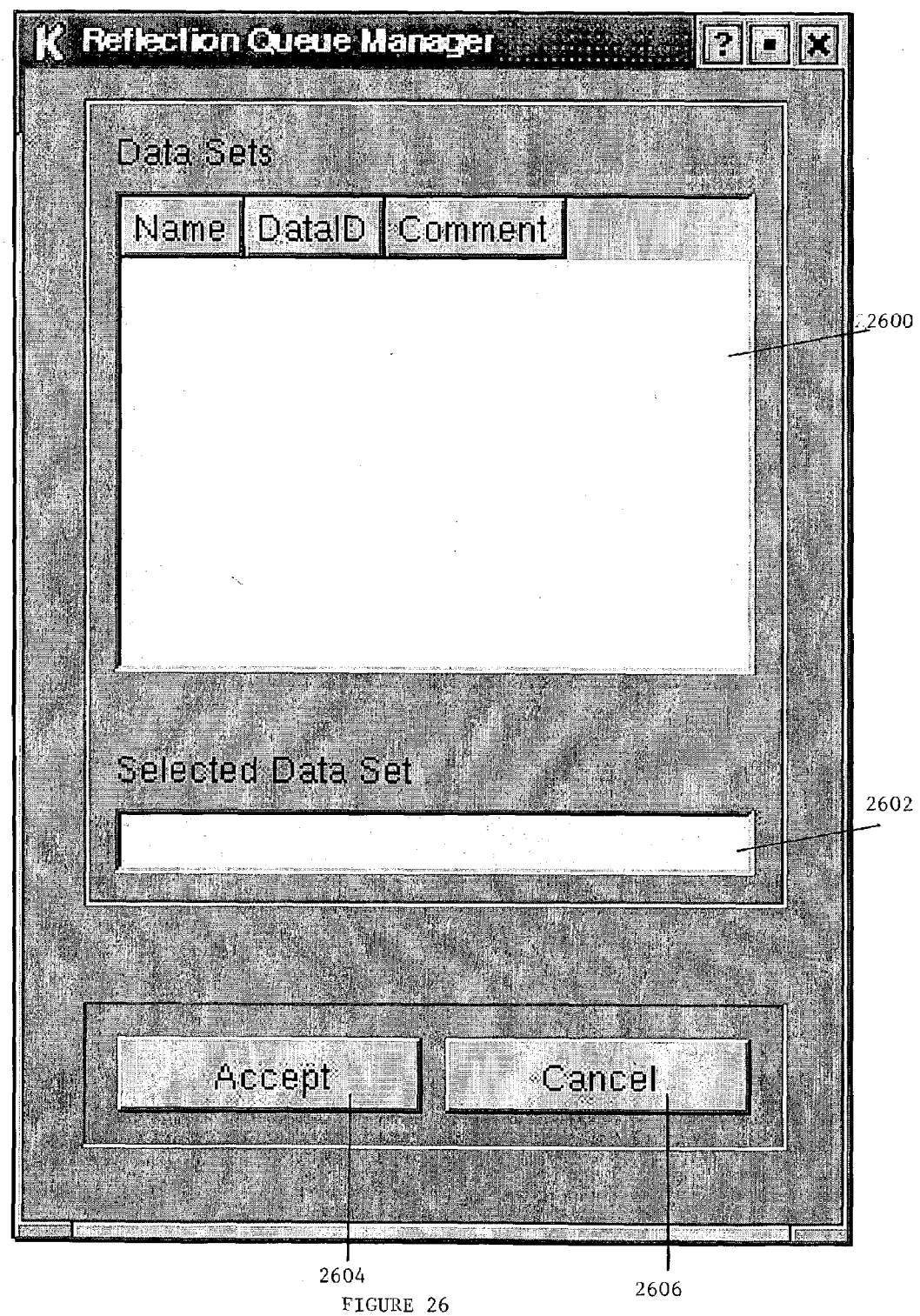
Figure 28:
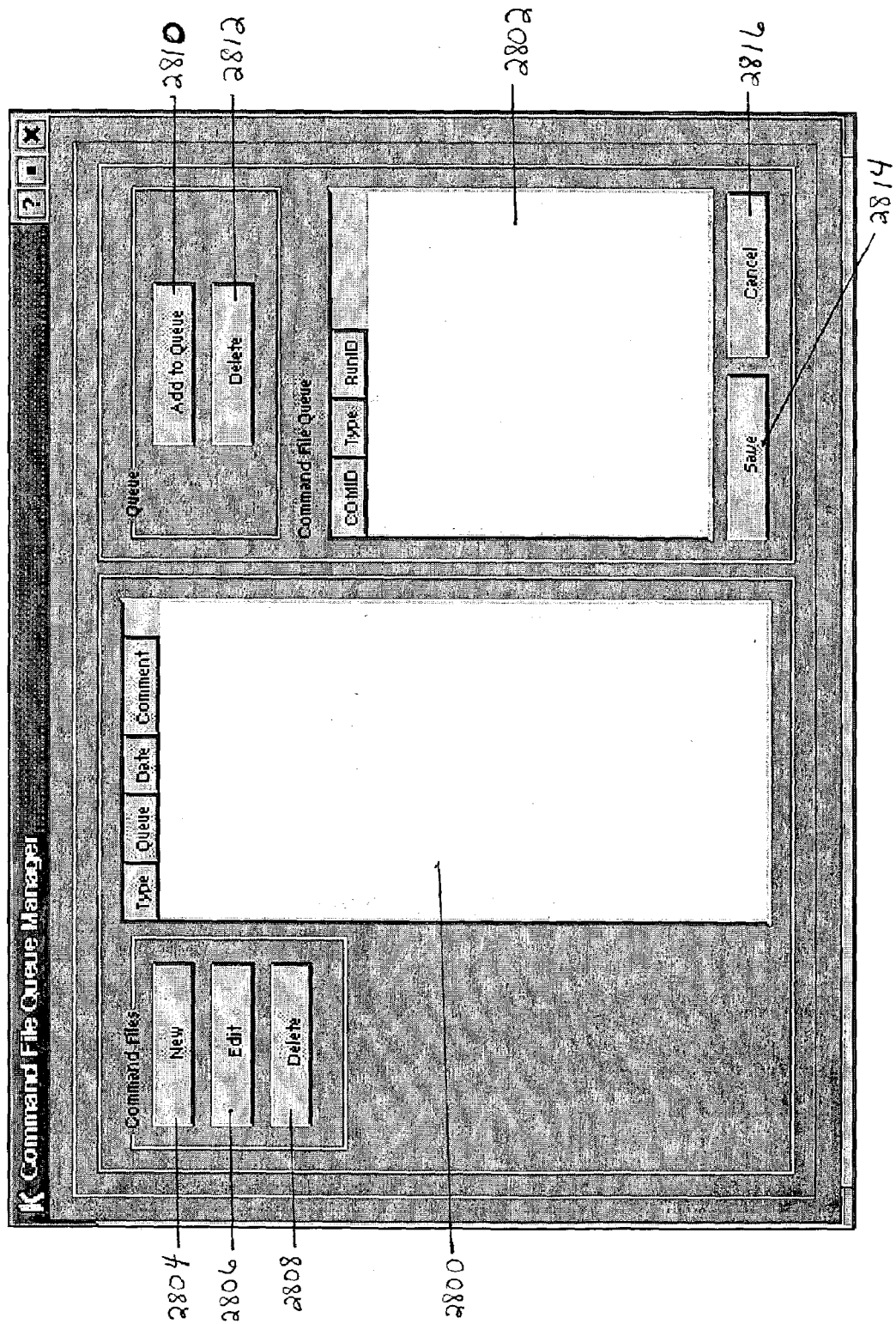

The input tab's primary function is to tabulate the user's choice in run parameters. The steps required to execute a run begin with the activation of the new button 1704. A new run entity is created in the database tables. The user must then select a data set, a template command file, and a search model queue in order to complete the minimum steps necessary to execute a run. A data set is selected from the database by pressing the reflection file select button 1732. There upon a reflection queue manager dialog window is opened (FIG. 26). Once a data set has been selected, the user may proceed to the command file queue manager. Under normal operation, the user will press the new command file queue button 1736, which will launch a new command file queue manager dialog window (FIG. 28). The final step includes selection of the search model queue. The search model queue is selected by pressing the select search model queue button 1742. Additional run specific parameters are selected from the parameters listed in the window.

Several customizations can be made to the search model queue via the optimize 1754 check box, the fragment check box 1756, the subdivide chains check box 1752, and the subdivide domains check box 1750. These actions are represented by steps 1750–1760 in FIGS. 20–21. The fragment check box causes each model in the selected queue to be fragmented in 50 residue intervals and tested in the molecular replacement. Similarly, the subdivide chains and domains check box causes any chains or domains to be treated as separate search models. In the case where the subdivide chain checkbox is selected, a hypothetical heterotrimeric protein with A, B, and C subunits would be subdivided into three separate search models according to the three different chain identifiers. If the subdivide domains checkbox is toggled, any chains composed of two or more domains will be subdivided into two or more search models. The original queue selected by the user in the second step will be expanded to accommodate these customizations prior to execution.

The user also has the ability to determine how the best solutions are selected from the results of the rotation function. These solutions form the starting point for the translation and rigid body functions. The log file generated by AMoRe includes four different correlation coefficients as a means to evaluate how well the model and data are correlated for any given solution. Most crystallographers rank the solutions according to CCF or CCP. The user can choose between the two by toggling the CCP radio button 1758 and the CCF radio button.

And finally, the optimize checkbox 1754 provides the user with the possibility of optimizing two of the parameters used in the rotation function. Both cell model parameter and sphere parameters are optimized when this check box is selected. A search model is run using a range of combinations for cell model and sphere parameters. In total, optimization includes approximately 4500 iterations per model and is thus computationally intensive.

The user is provided feed back during the run execution via real time updates that appear in the setup tab window. The updates include the run id 1714, the run status 1718, the current search model 1720, the run start time 1722, run end time 1724, and the run duration 1726.

The user may perform additional operations on a run. By pressing the run delete button 1708, the user deletes the currently loaded run. Pressing the run close button 1712 causes the run manager to exit and return to the main manager. Any comments the user would like to associate with a run can be entered into the database via the comment field 1728. Pressing the execute button 1710 causes the program to launch a molecular replacement search according to the parameters specified in the run manager. At the same time, the execution button is disabled to prevent the user from accidentally initiating another run without first going through the process of initializing a new run.

The run open button 1706 allows the user to load a currently executing or previously completed run into run manager. A run must be loaded into the run manager in order to access output parameters via the output tab.

Run Manager: Run Output Tab

The output tab provides a framework for viewing the solutions generated by a molecular replacement search. It includes a solution list view 2200. To load solutions into the list view a user must first press the update log button 2220. All solutions belonging to the run and which meet the statistics cutoff criteria set in the output tab at the time the log button was press are loaded into the list view. Each solution is listed along with statistics calculated at run time. These statistics are provided as a way to gauge the strength and quality of the solution. The user may chose to apply a cutoff for each of the statistical values and thereby cull out the weakest solutions. Cutoffs may be applied for the CC Ratio 2228, Sigma (signal-to-noise) 2230, CCF 2232, inclusive Kurtosis 2234, and exclusive Kurtosis 2236. The cutoffs may be enabled/disabled through check boxes. These actions are represented by steps 2204–2205, 2206–2207, 2208–2209, 2210–2211, and 2212–2213 of FIG. 23. Once enabled, the cutoff value may be entered directly in the text field of the scroll box adjacent to the check box or incremented/decremented via the up and down arrow keys of the scroll box. These actions are represented by steps 2229, 2231, 2233, 2235, and 2237 of FIG. 23.

By double clicking on an entry in the list view, the user may write out to the hard disk, a coordinate file, a calculated electron density map, or the sequence for the search model of a particular solution. The different choices may be selected by toggling between the PDB radio button 2214, the CCP4 map radio button 2216, and the sequence radio button 2218. At any time, the user may also write out a copy of the current list view to the hard disk by pressing the write log view button 2222. Any file written out in such a manner may be read into memory and redisplayed in the list view by pressing the read log button 2224.

Reflection Queue Manager

Figure 27:
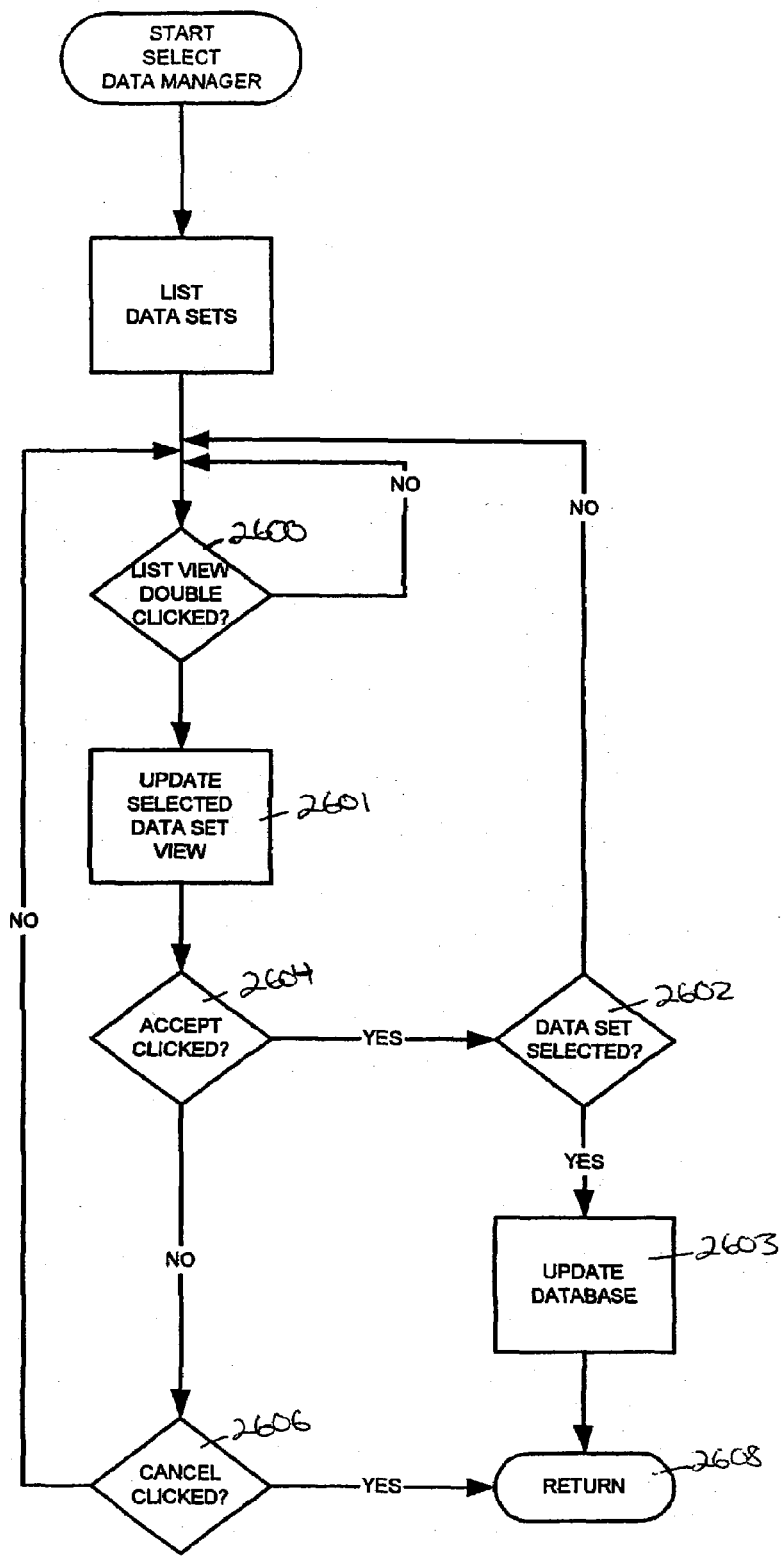

The data selection manager allows the user to select a reflection data set from the database. The data selection manager is called from the run manager. The new dialog window displays the name, data id, and comments of the appropriate data sets in the list view 2600. A user may chose a data set by double clicking on an entry in the list view. The name of the entry is displayed in the selected data set text view 2602. This action is represented by steps 2600–2601 in FIG. 27. A user may chose to accept the selected data set by actuating the accept button 2604 which will update the database and close the dialog window. Otherwise the user may chose to select another entry from the list view or cancel the operation entirely by pushing the cancel button 2606. These actions are represented by steps 2602–2608 in FIG. 27.

Command File Queue Manager

Figure 29:
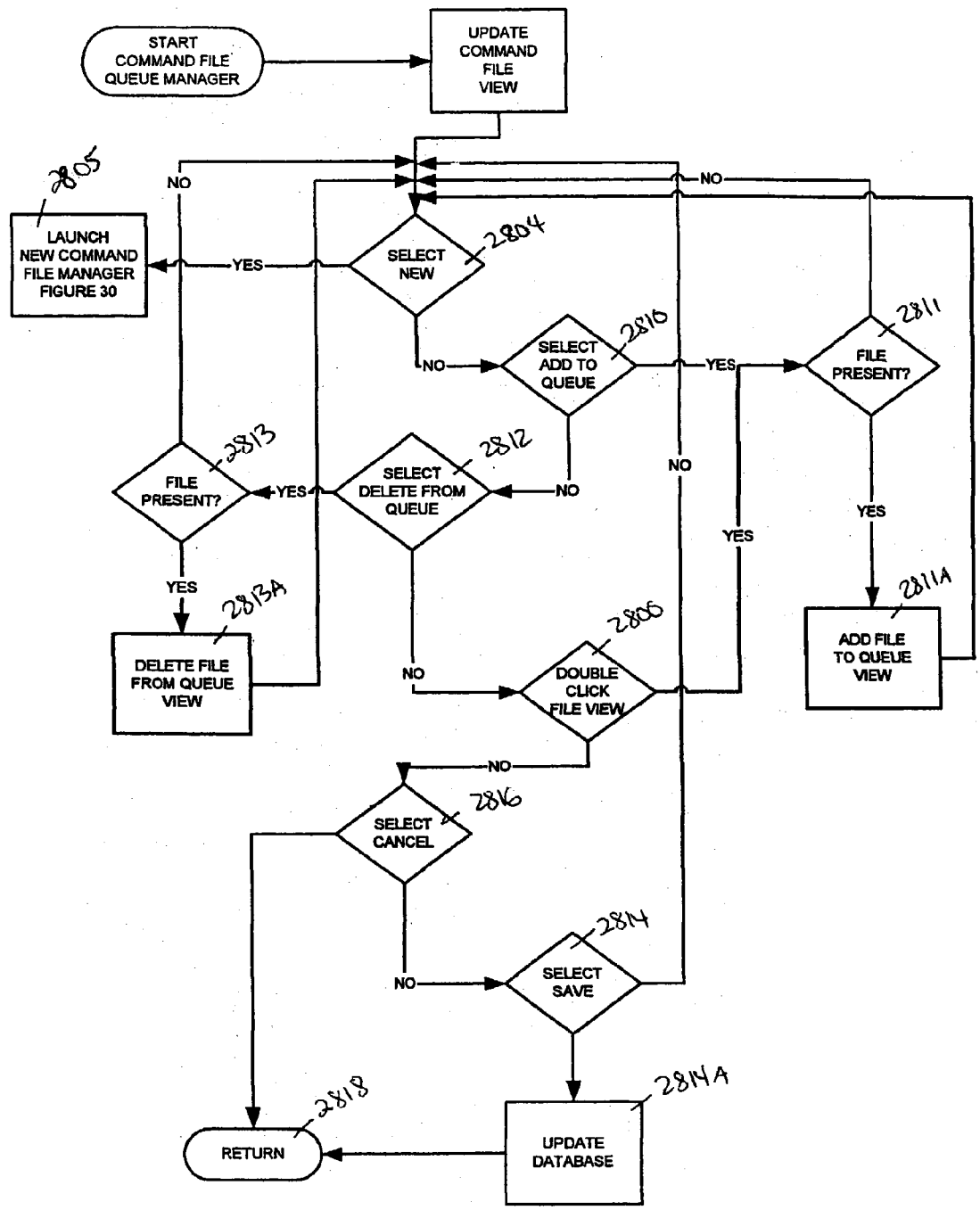
Figure 30:
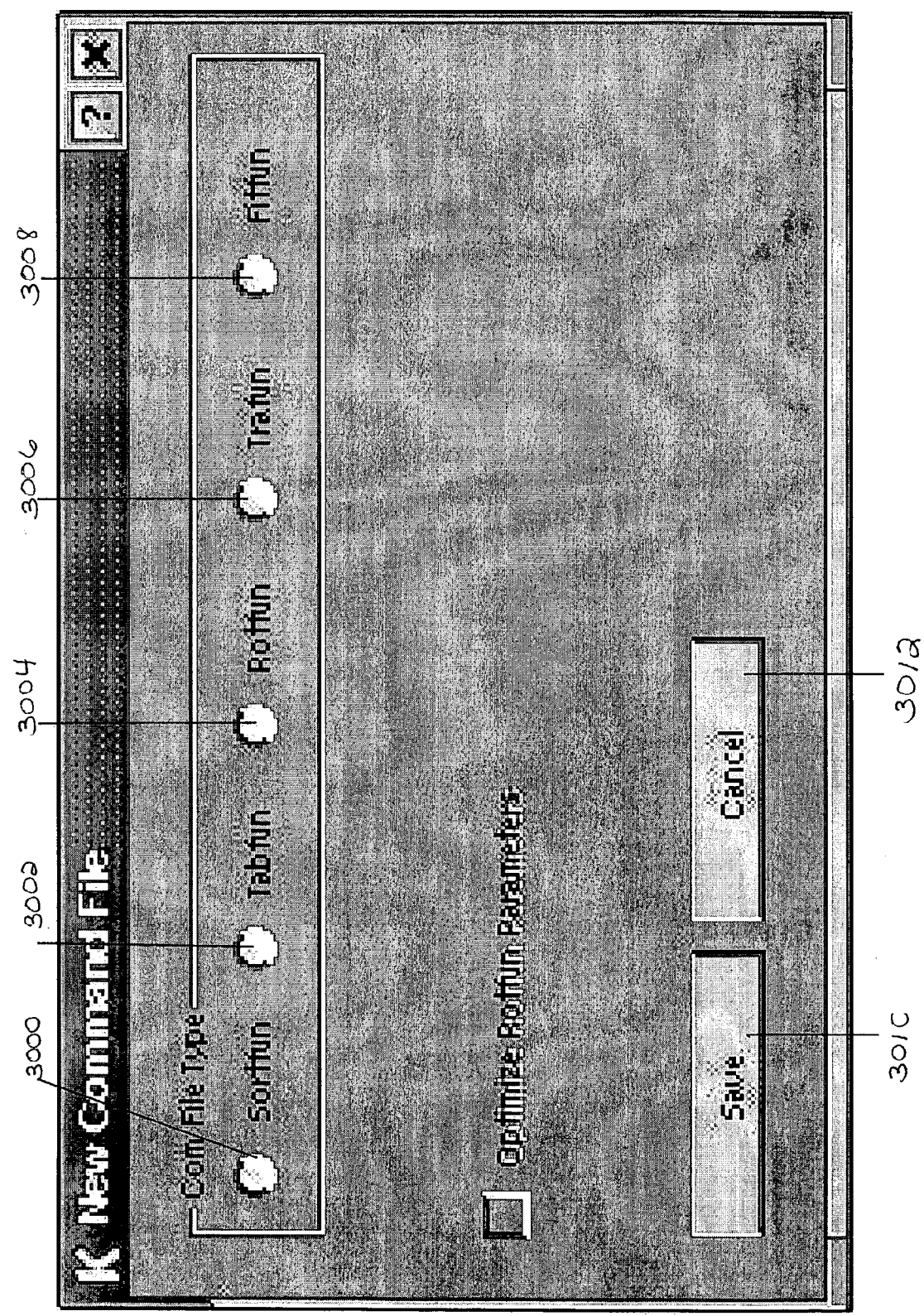

A new command file queue is creating by first generating the template command files and then adding them to a user defined command file queue. A set of new command files may be generated by means of the new command file manager (activated by clicking on the new button 2804). Typically, new command files will include files for the SORTFUN function, the TABFUN function, the ROTFUN function, the TRAFUN function and the FITFUN function of AMoRe. The command file list view 2800 is refreshed after the template fore each command file is generated. After the desired command files are generated, each command file is added to the command file queue by double clicking on the entry in the command file list view. The action causes the entry to be transferred to the queue list view 2802. These actions are represented by steps 2810, 2811 of FIG. 29. Alternatively, the entry may be added by clicking on the add to queue button 2810. This action is represented by steps 2800 and 2811 of FIG. 29. A file may be deleted from the command file queue by selecting the entry and then clicking on the delete button 2812. The selection is finalized and the database is updated when the user clicks on the save button 1814. The entire process of generating a queue may be canceled and the manager closed by clicking on the cancel button 2816. The final steps of command file queue selection are represented by steps 2814, 2816 and 2818.

New Command File Manager

Figure 31:
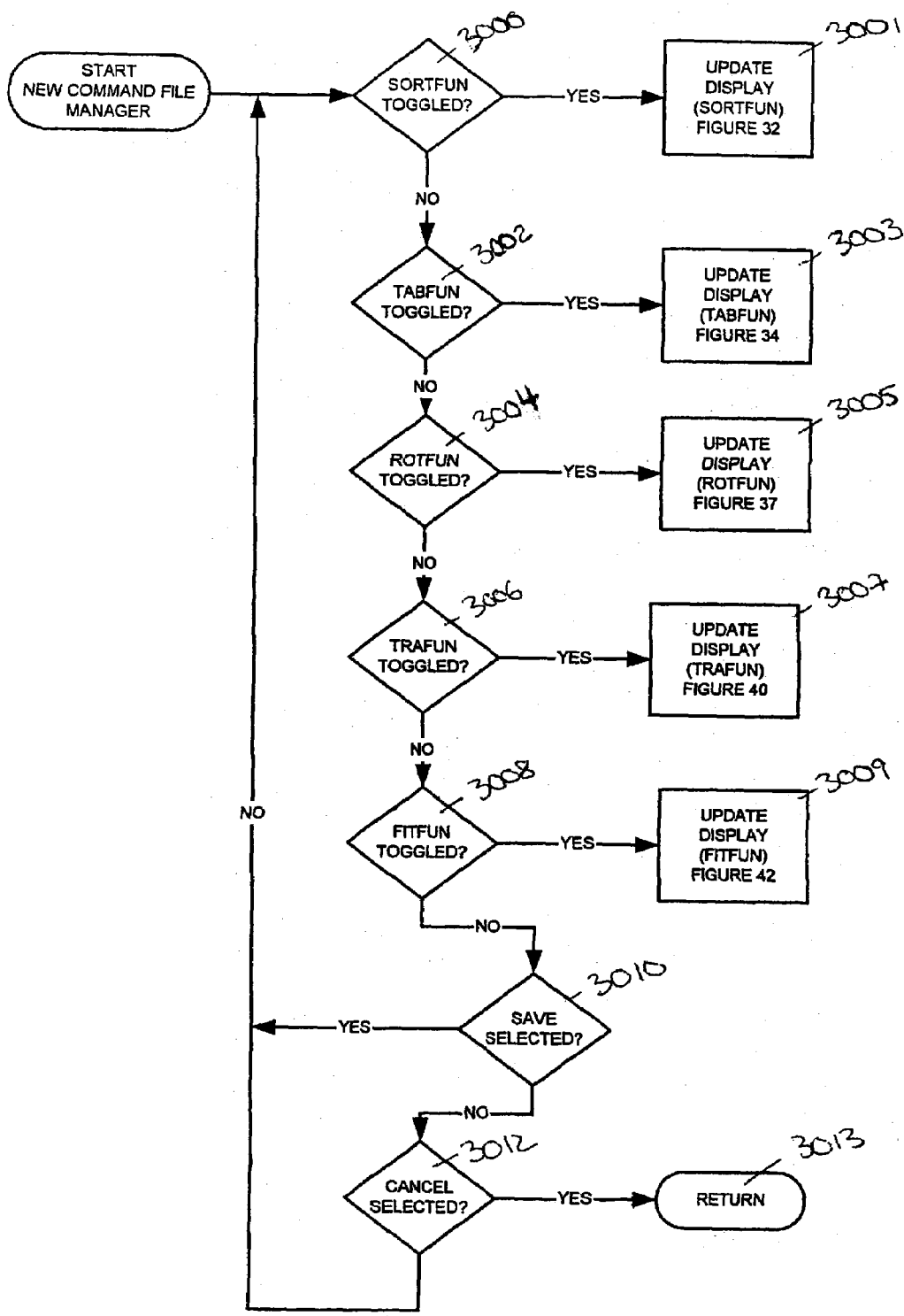

The command file manager allows the user to customize a command file template for each of the five different command files normally required to execute a complete molecular replacement search with AMoRe. The initial configuration of the manager consists of a dialog window with five radio buttons. A user may elect to generate a new command file template for the SORFUN function of AMoRe by toggling the sortfun radio button 3000. In a similar manner, other command files may be generated by clicking on the tabfun radio button 3002, the rotfun radio button 3004, the trafun radio button 3006, or the fitfun radio button 3008. A click on any of the radio buttons causes the command file manager to be redrawn to accommodate command file specific widgets (FIGS. 32–43). These actions are represented by steps 3000–3009 of FIG. 31. The widgets allow the user to enter command file parameters for the various functions used in the molecular replacement search. The user may chose to save or discard the command file parameters by clicking either the save button 3010 or the cancel button 3012 respectively.

Command File Manager: Sortfun Widget

Figure 32:
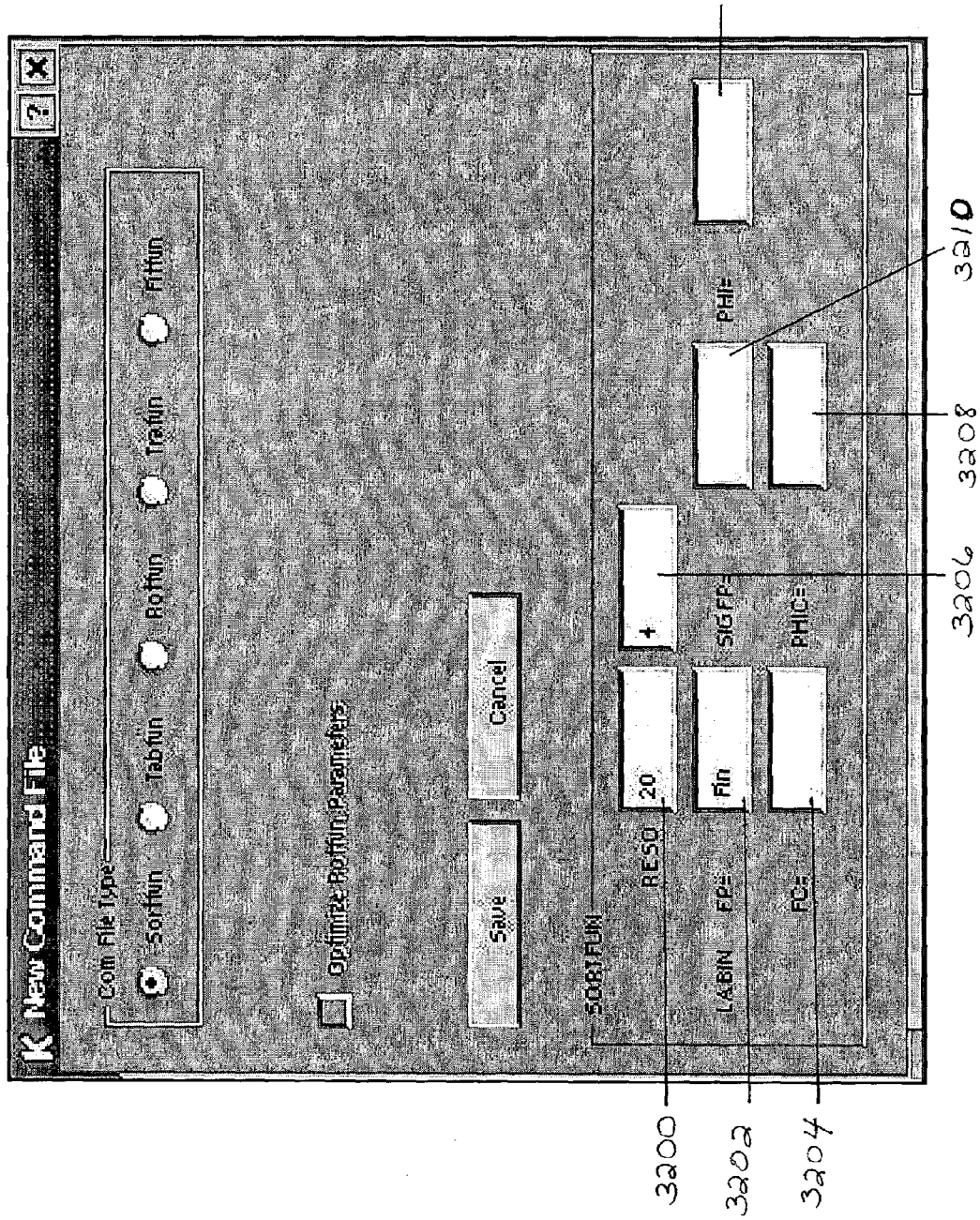
Figure 33:
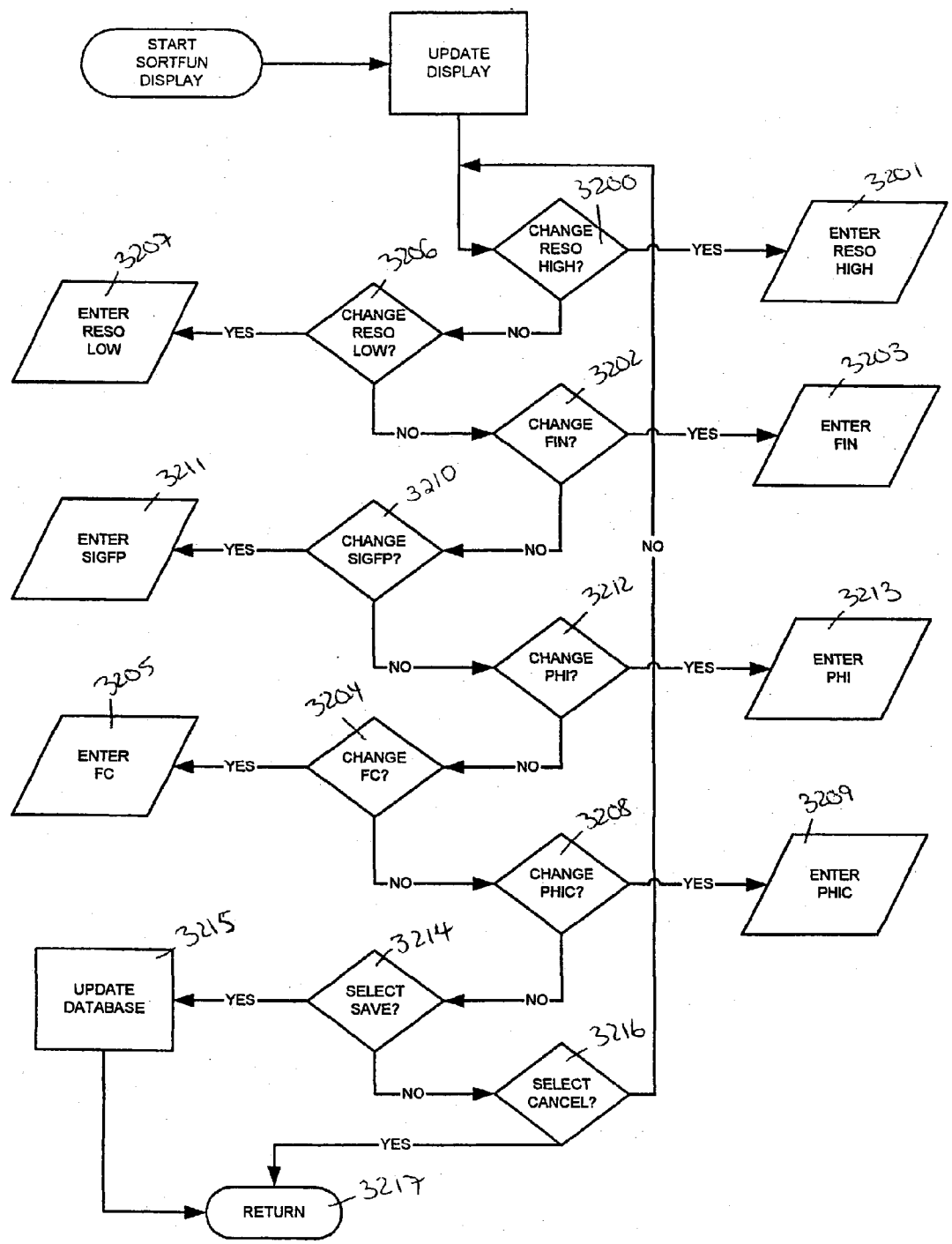

FIG. 32 shows the sortfun widget displayed in the context of the command file manager. The widget has data entry fields with which the user may enter values for the high and low resolution limits in the high resolution text field 2300 and the low resolution text field 3206. Data columns in the reflection file may be labeled according to values entered in the FP text field 3202, the SIGFP text field 3208, the PHI text field 2312, the FC text field 3204, and the PHIC text field 3210. These actions are represented by steps 3200–3209 of FIG. 33. Each sortfun command file is preset with default values, which are displayed in the appropriate text box. The default, or modified values, may be saved to the database, or rejected, in a manner described previously for the command file manager.

Command File Manager: Tabfun Widget

Figure 34:
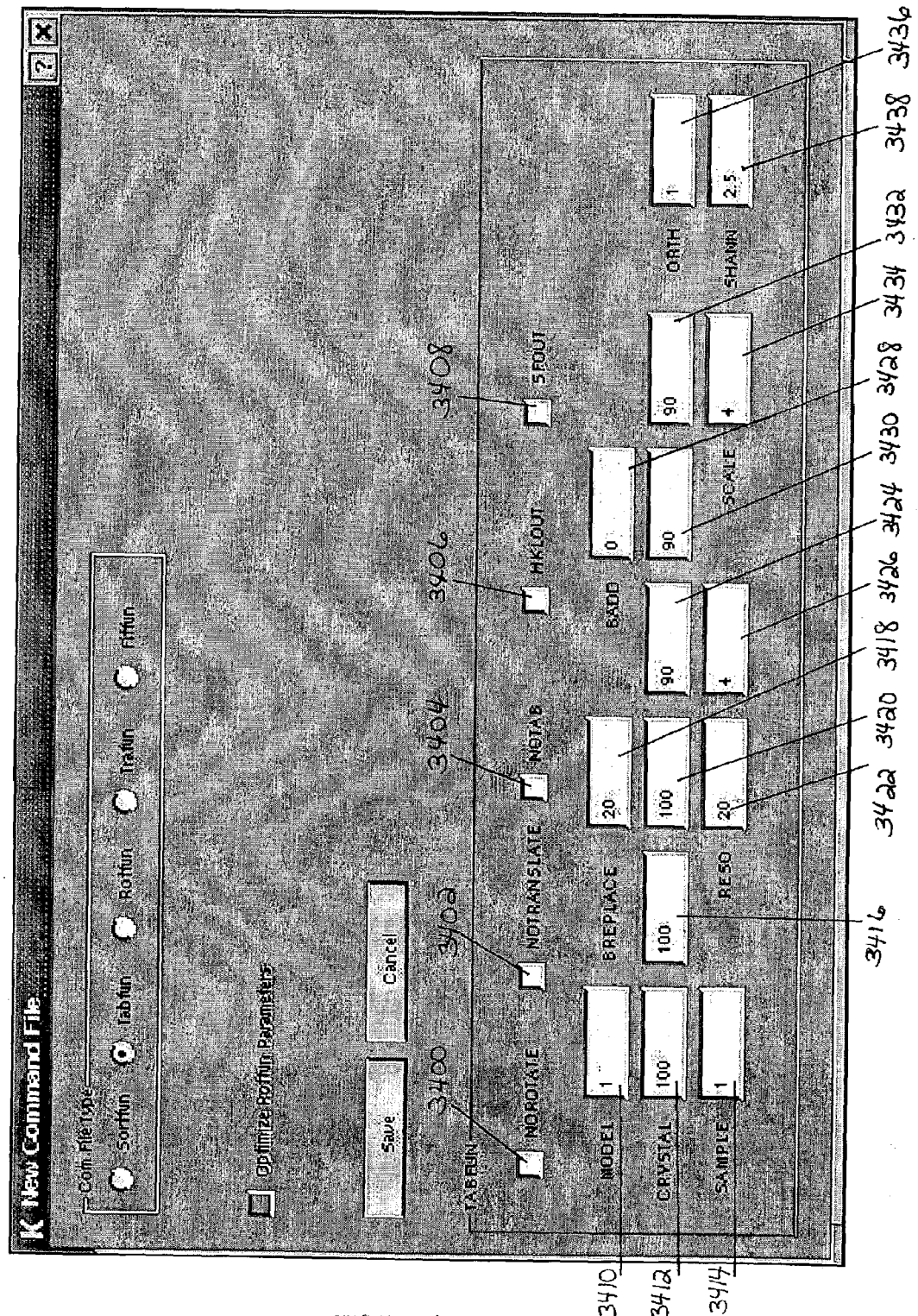
Figure 35:
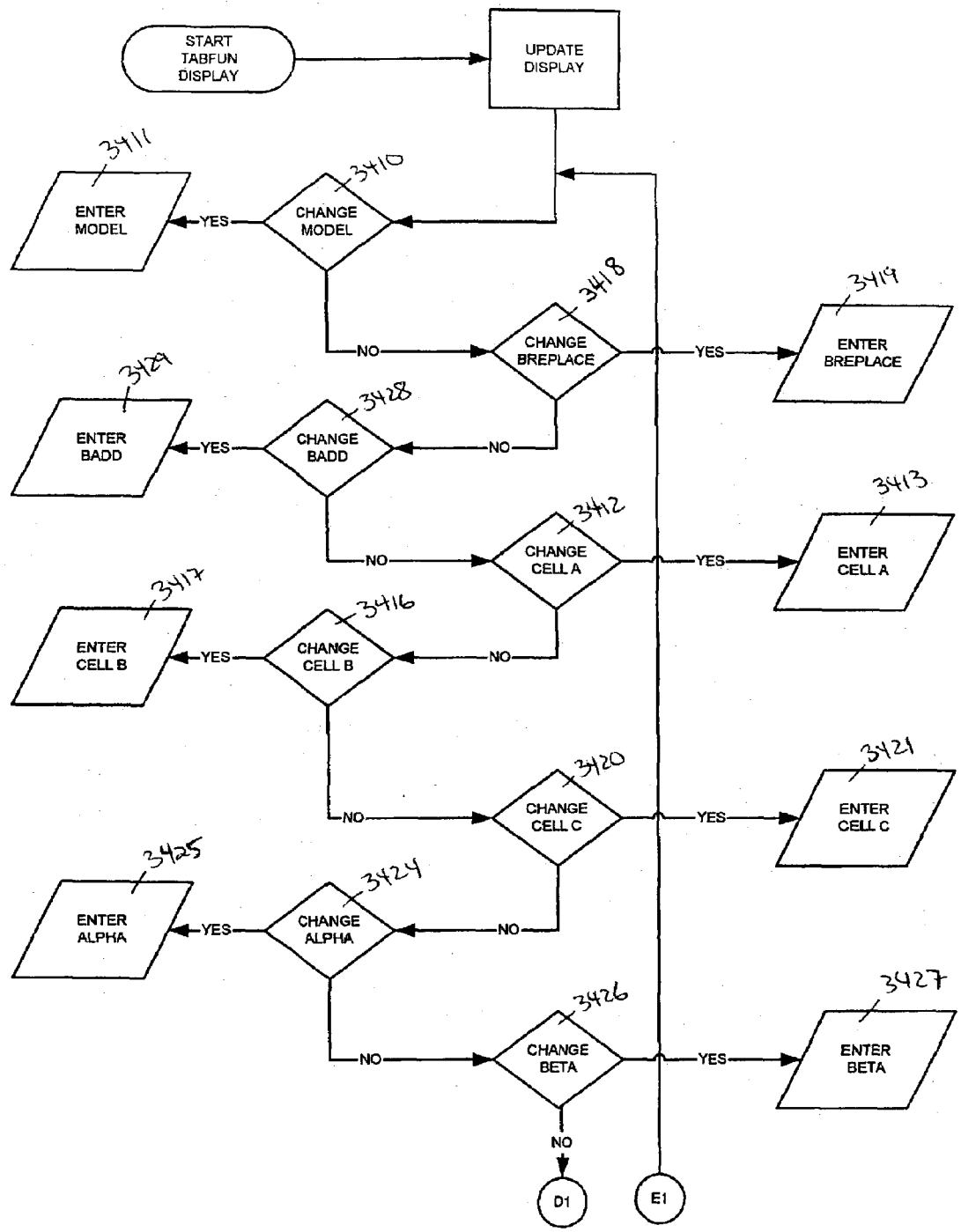
Figure 36:
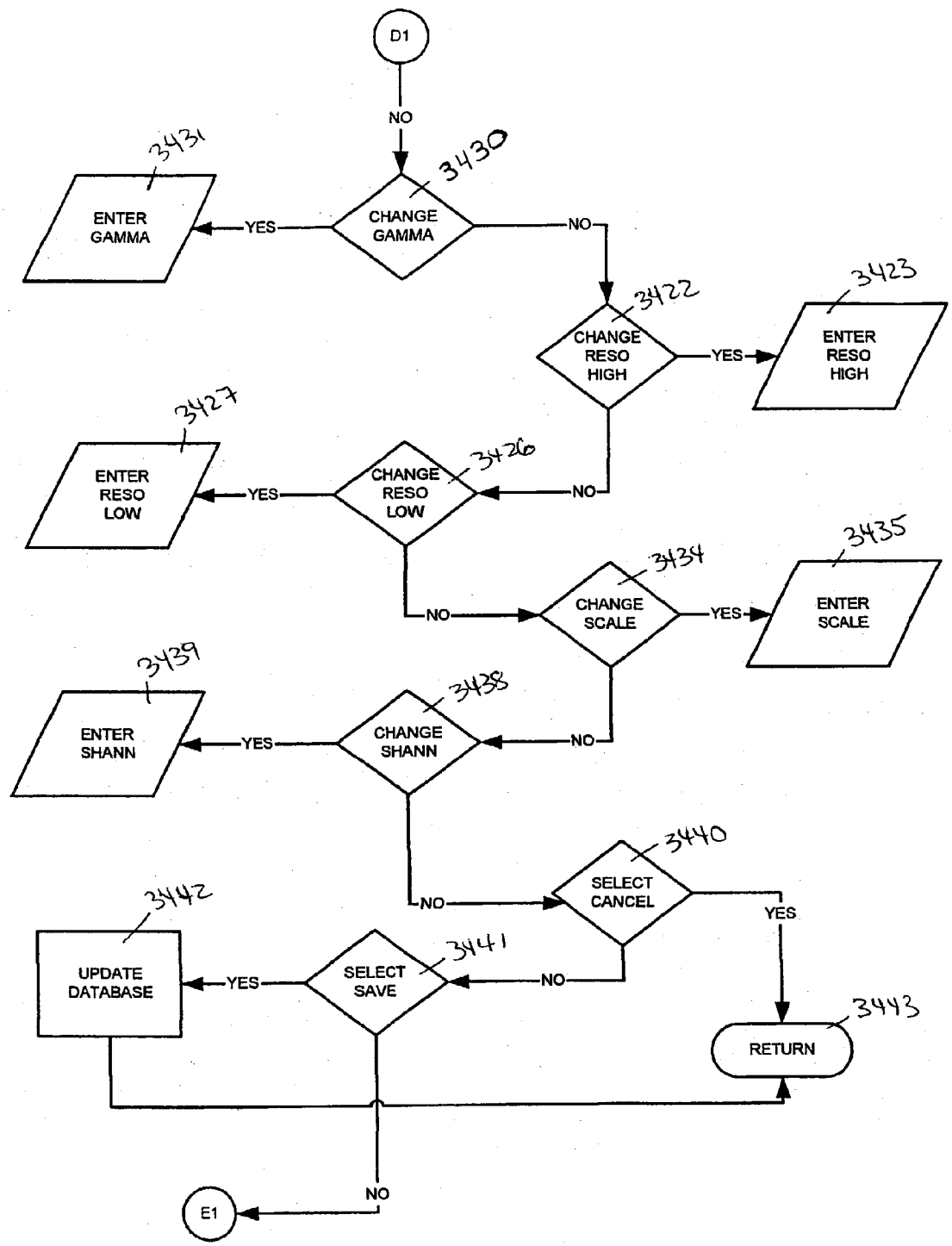

FIG. 34 shows the tabfun widget displayed in the context of the command file manager. The widget has data entry fields with which the user may enter parameters specific to the AMoRe tabfun function. A user may enter parameters in the model text field 3410, the breplace text field 3418, and the badd text field 3428. Unit cell parameters for the data may be entered in fields 3412, 3416, 3420, 3430, and 3432. Additional parameters may be entered in text fields 3414, 3422, 3426, 3434 and 3438. Tabfun specific flags may be included by selecting the norotate check box 3400, the notranslate check box 3402, the notab check box 3404, the hklout checkbox 3406, or the sfout check box 3408. These actions are represented by steps 3410–3439 of FIGS. 35 and 36. Each tabfun command file is preset with default values, which are displayed in the appropriate text box. The default, or modified values, may be saved to the database, or rejected, in a manner described previously for the command file manager.

Command File Manager: Rotfun Widget

Figure 37:
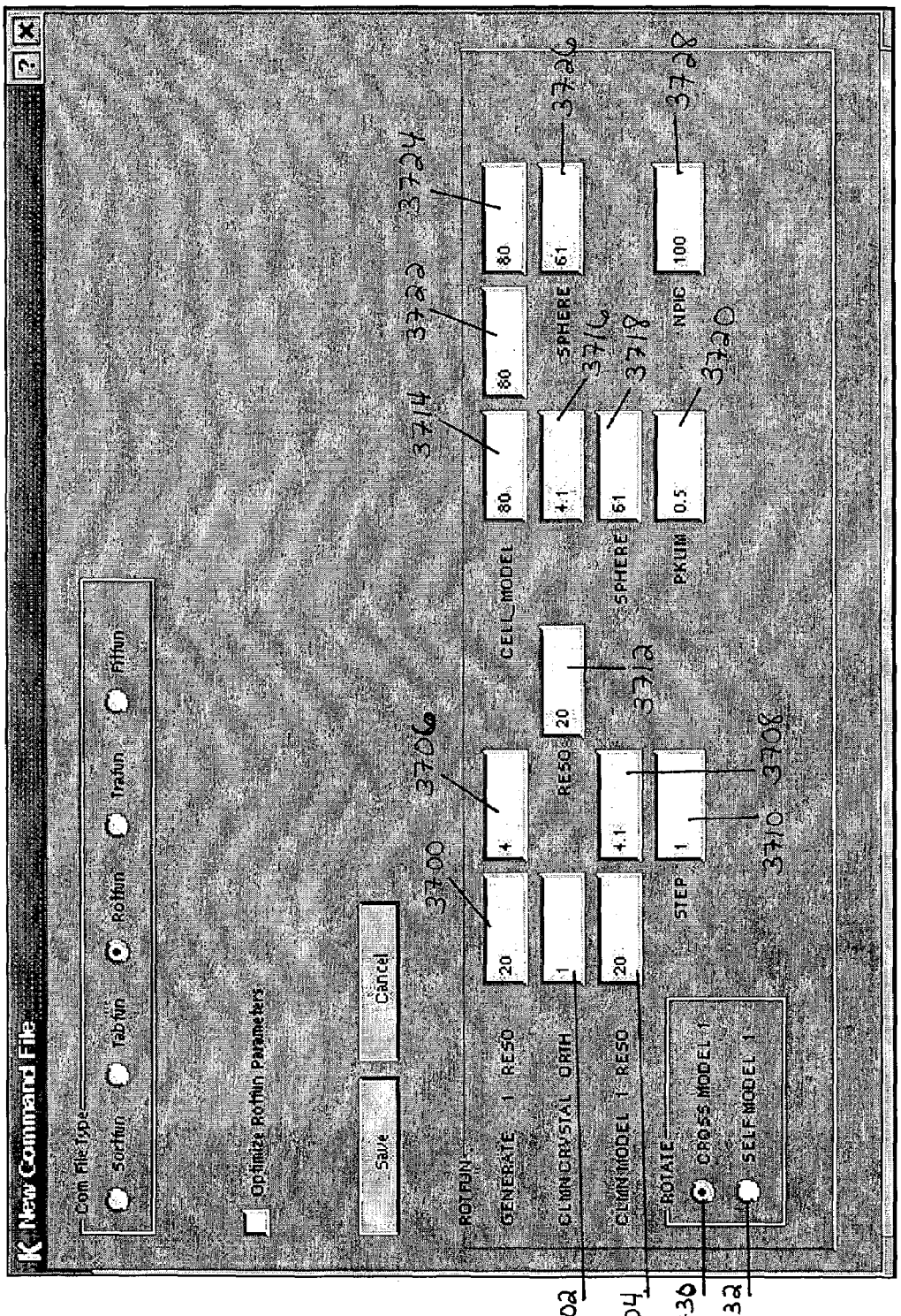
Figure 38:
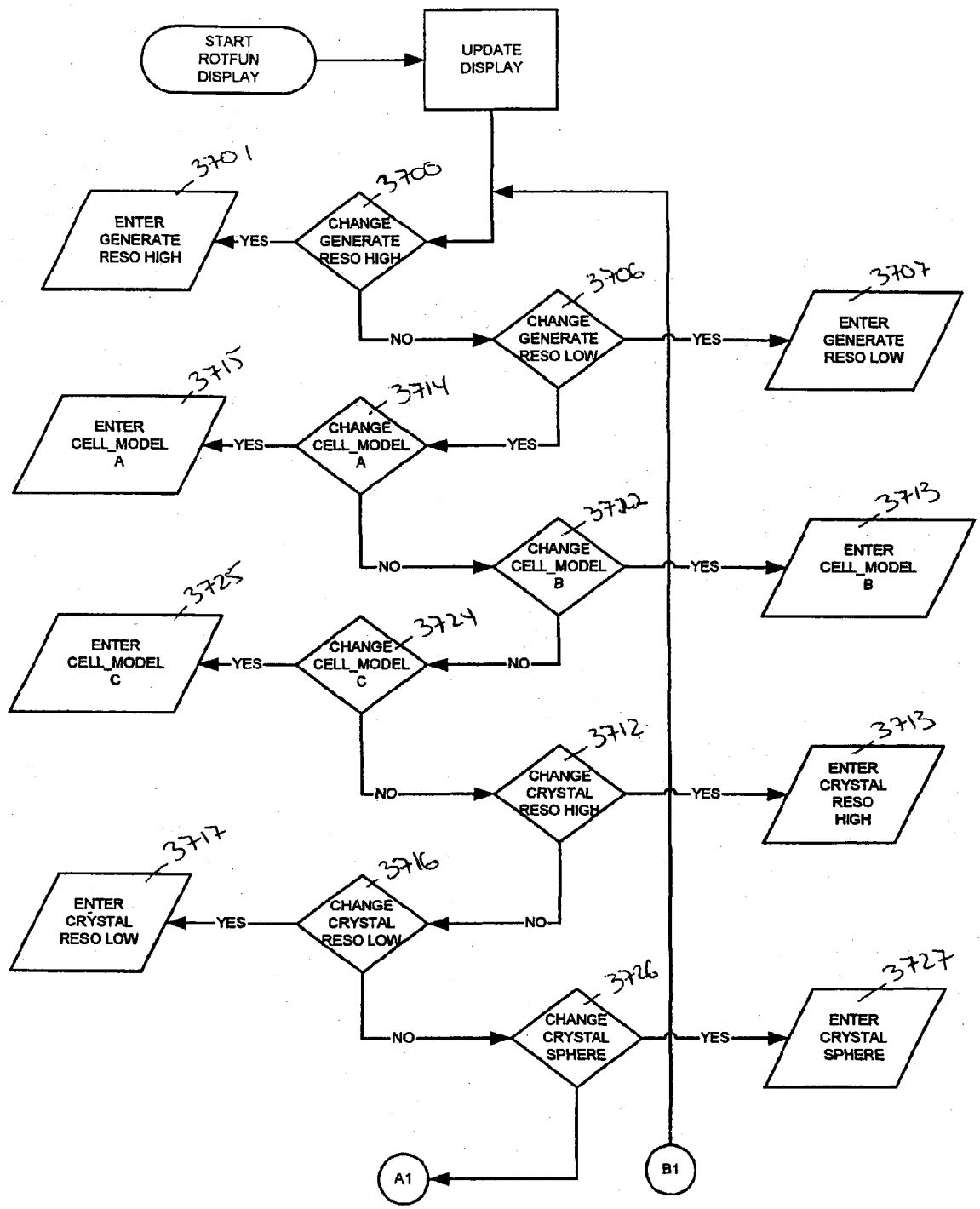
Figure 39:
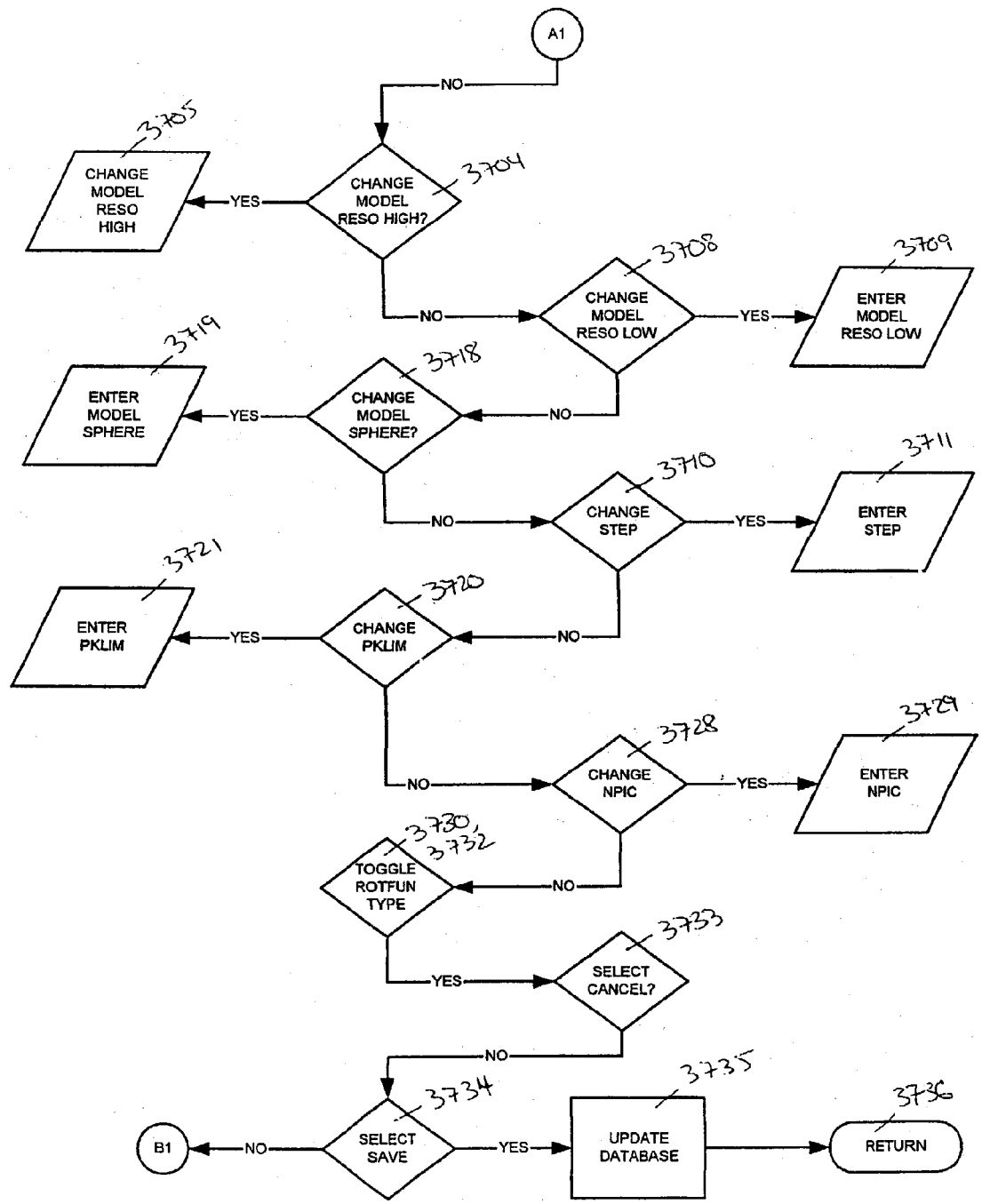

FIG. 37 shows the rotfun widget displayed in the context of the command file manager. The widget has data entry fields with which the user may enter parameters specific to the AMoRe rotfun function. A user may enter parameters in the low resolution text field 3700 and the high resolution text field 3706. The dimensions for the P1 unit cell box may be entered via the cell_model text fields 3714, 3722, and 3724. Additional rotfun specific parameters may be entered in the fields 3702, 3712, 3716, 3726, 3704, 3708, 3710, 3718, 3720, and 3728. The user may chose to pass flags to the rotfun module of AMoRe that indicate the type of rotation search to conduct by toggling between the cross radio button 3730 and the self radio button 3732. These actions are represented by steps 3700–3732 of FIGS. 38 and 39. Each rotfun command file is preset with default values, which are displayed in the appropriate text box. The default, or modified values, may be saved to the database, or rejected, in a manner described previously for the command file manager.

Command File Manager: Trafun Widget

Figure 40:
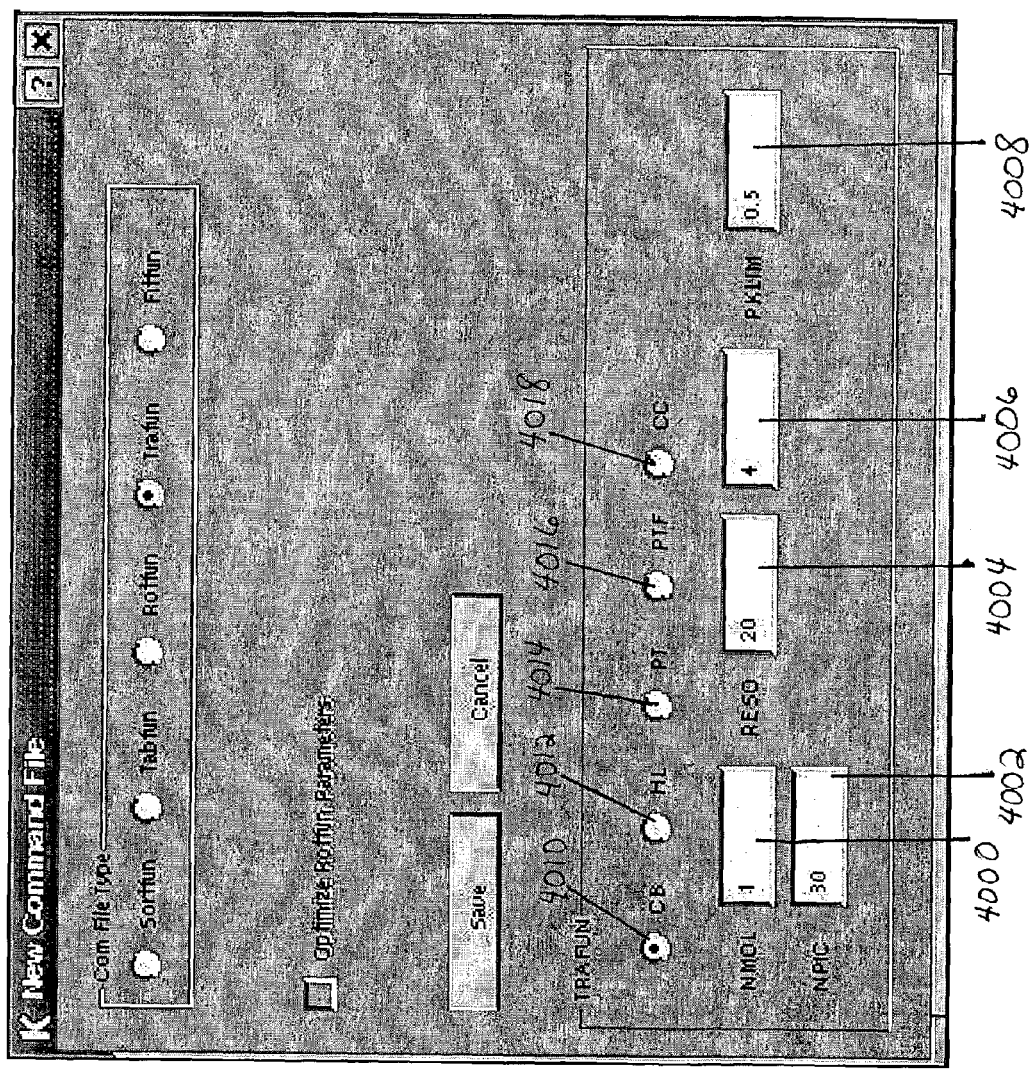
Figure 41:
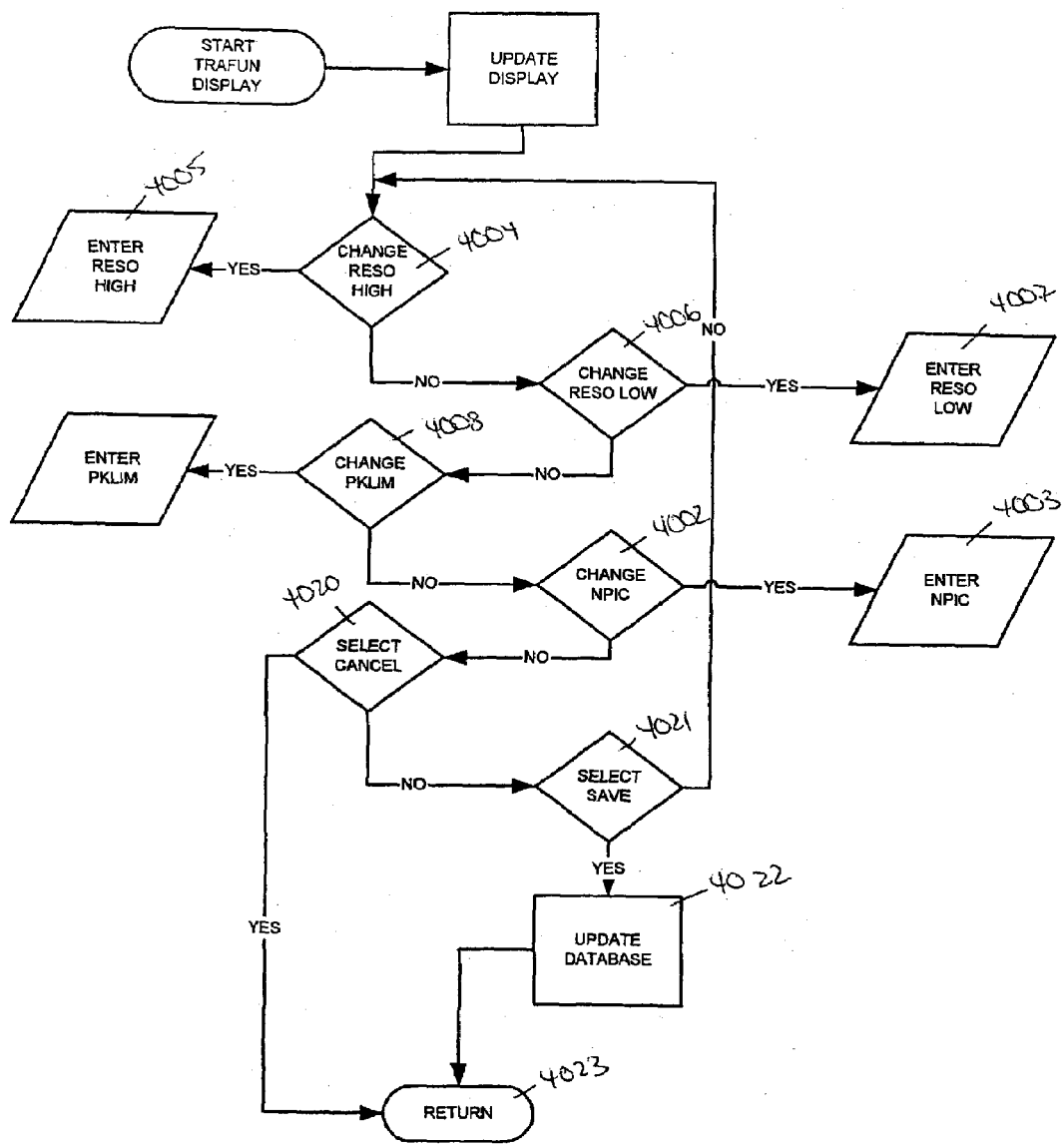

FIG. 40 shows the trafun widget displayed in the context of the command file manager. The widget has data entry fields with which the user may enter parameters specific to the AMoRe trafun function. The parameters may be entered via text fields 4000, 4002, 4004, 4006, and 4008. The user may chose to pass flags to the trafun module of AMoRe to indicate the type of rotation search to be conducted. This is achieved by toggling between the cb radio button 4010, the hl radio button 4012, the pt radio button 4014, the ptf radio button 4016, or the cc radio button 4018. These actions are represented by steps 4004–4003 of FIG. 41. Each trafun command file is preset with default values, which are displayed in the appropriate text box. The default, or modified values, may be saved to the database, or rejected, in a manner described previously for the command file manager.

Command File Manager: Fitfun Widget

Figure 42:
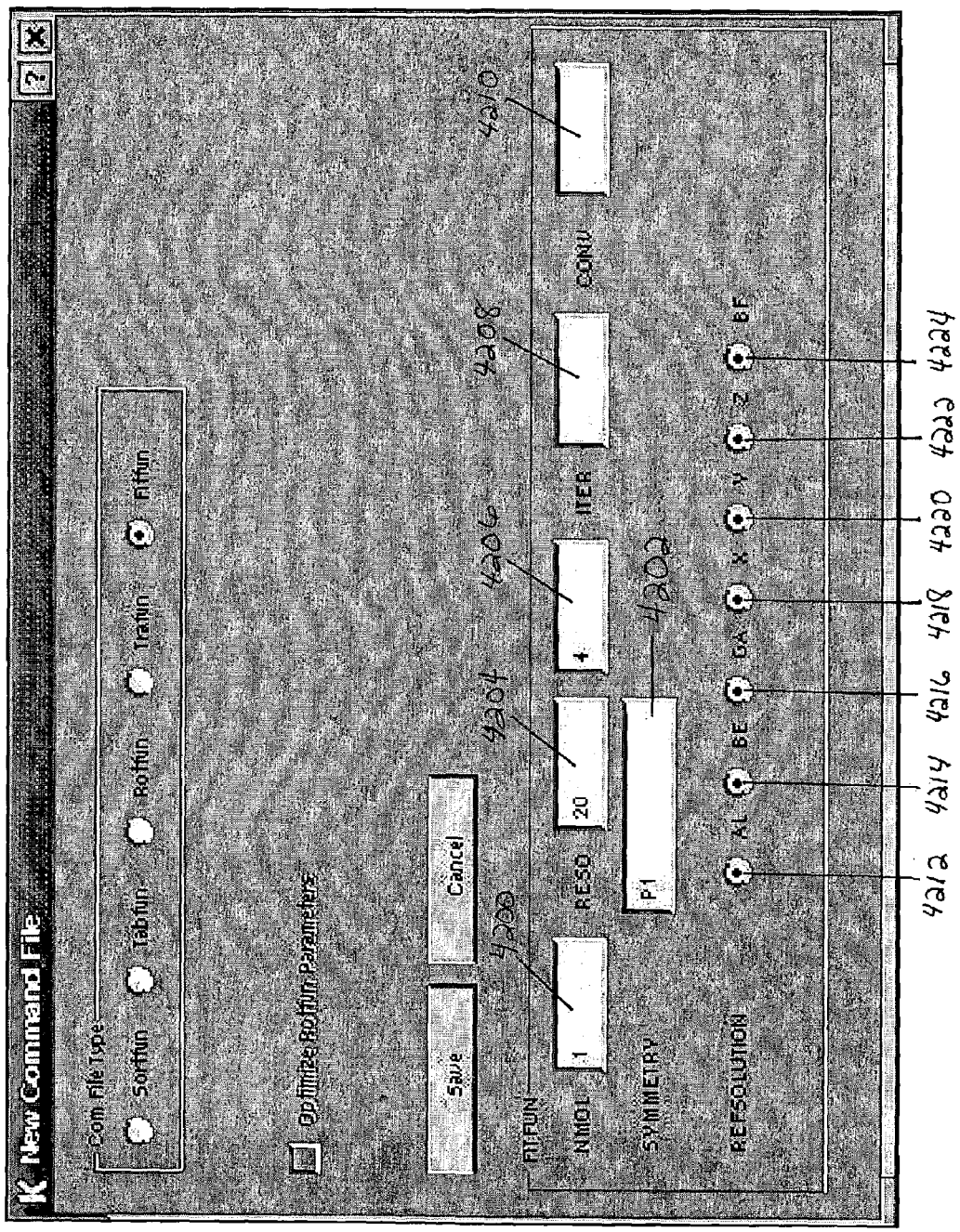
Figure 43:
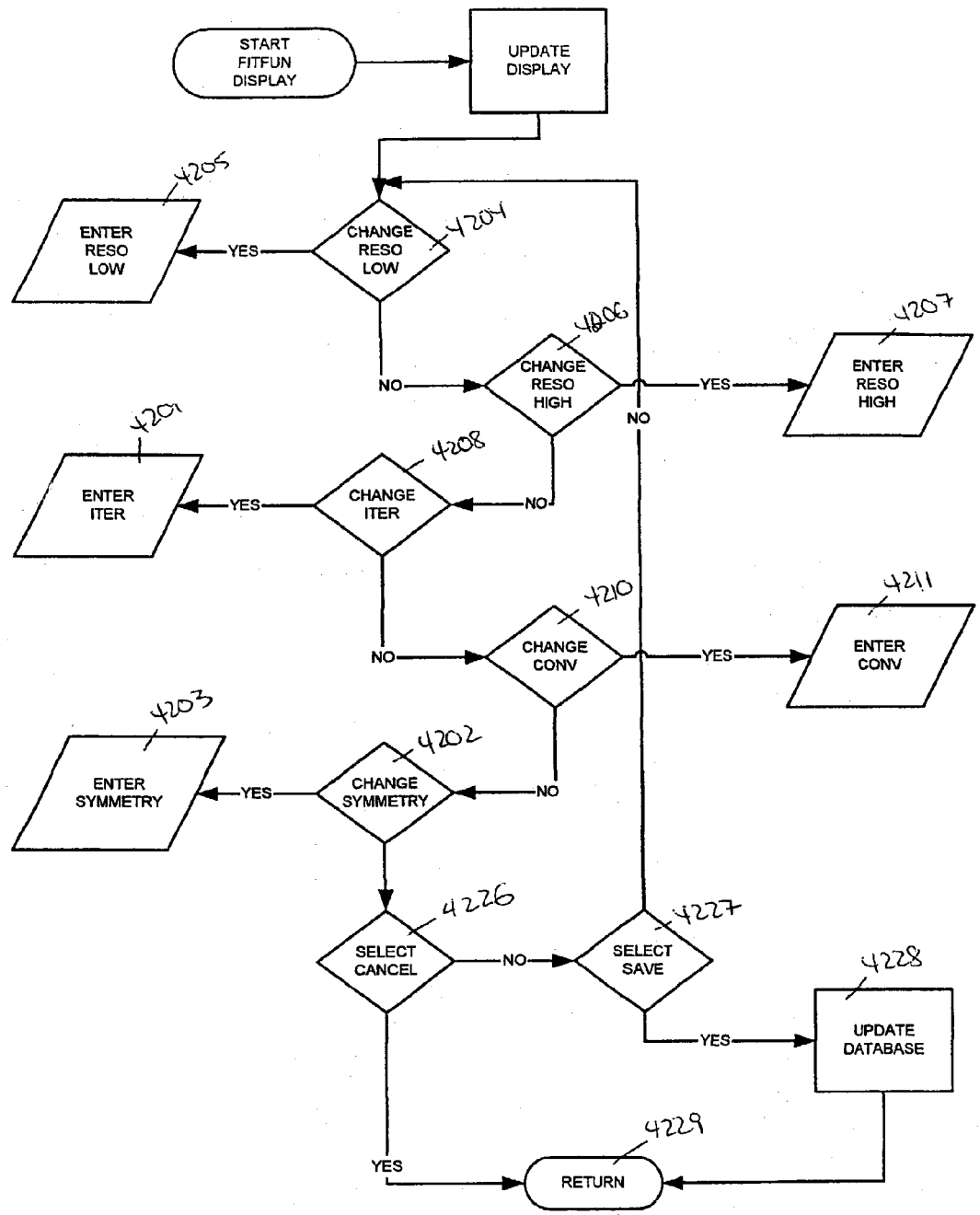
Figure 44:
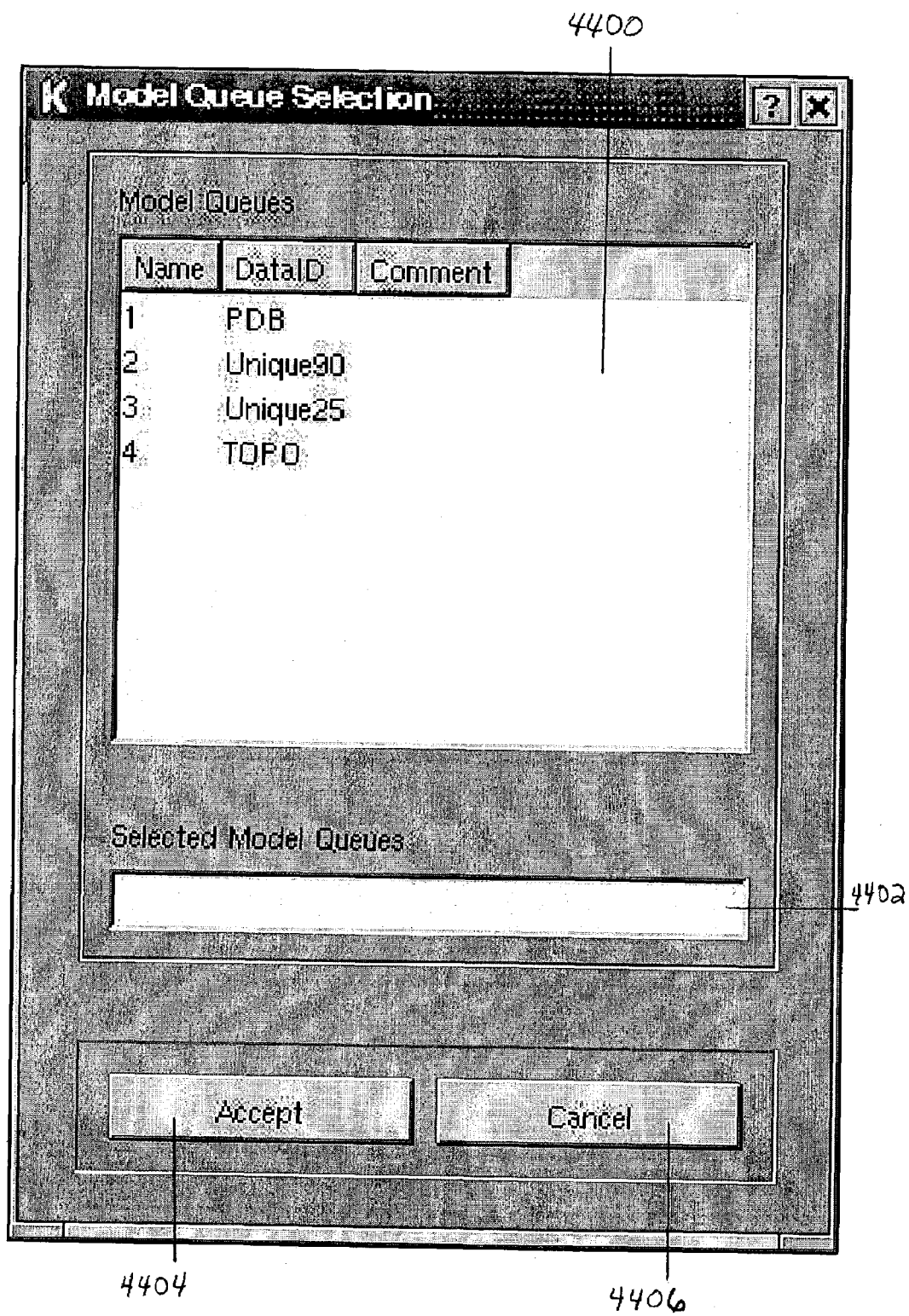

FIG. 42 shows the fitfun widget displayed in the context of the command file manager. The widget has data entry fields with which the user may enter parameters specific to the AMoRe fitfun function. A user may enter resolution limits via the low resolution text field 4204 and the high resolution text field 4206. Information regarding the space group is entered via the symmetry text field 4202. Additional parameters are entered in the text fields 4200, 4208, and 4210. Solution fields to be included in the log file are selected via the radio buttons 4212, 4214, 4216, 4218, 4220, 4222, and 4224. These actions are represented by steps 4204–4203 of FIG. 43. Each fitfun command file is preset with default values, which are displayed in the appropriate text box. The default, or modified values, may be saved to the database, or rejected, in a manner described previously for the command file manager.

Search Model Queue Selection Manager

Figure 45:
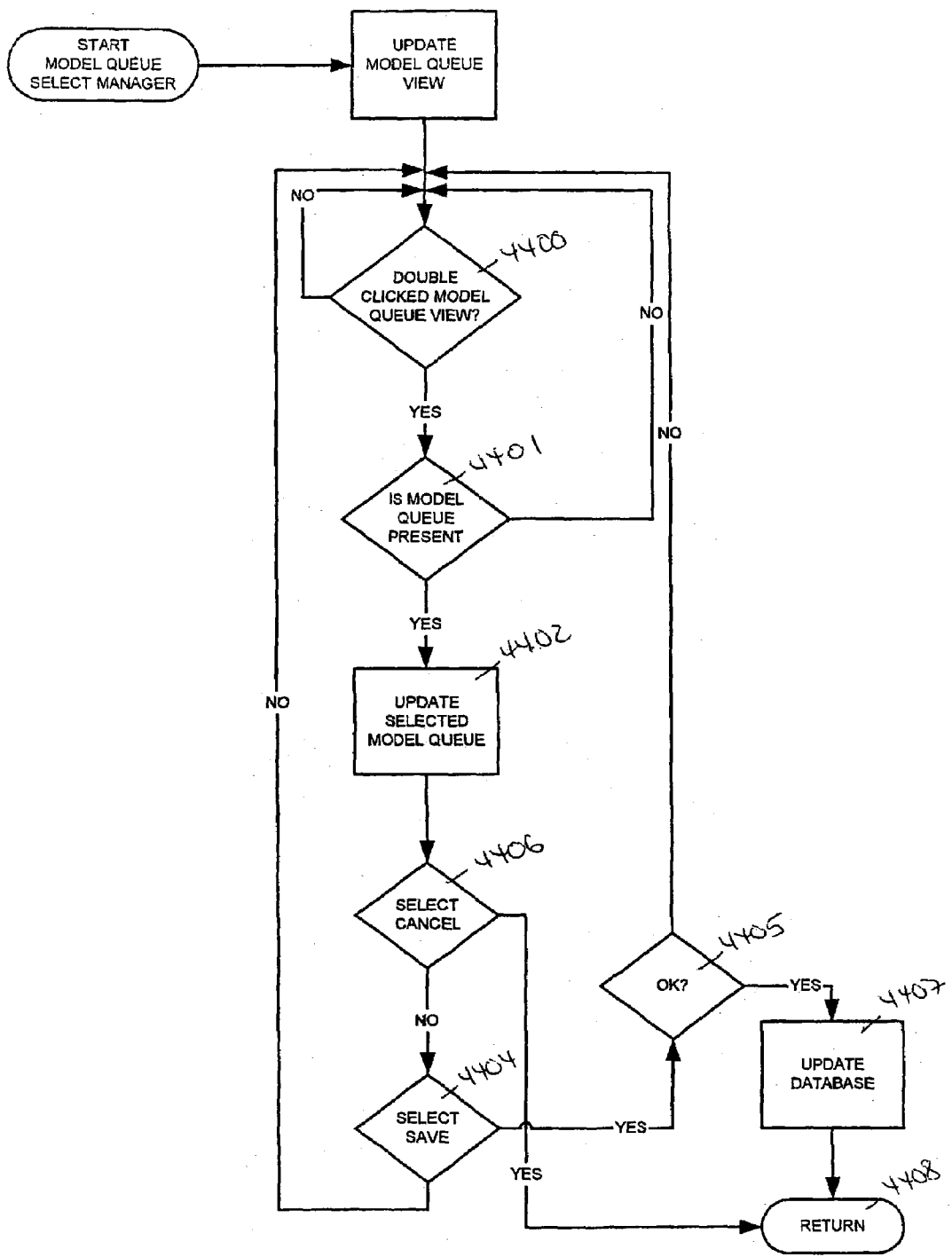
Figure 46:
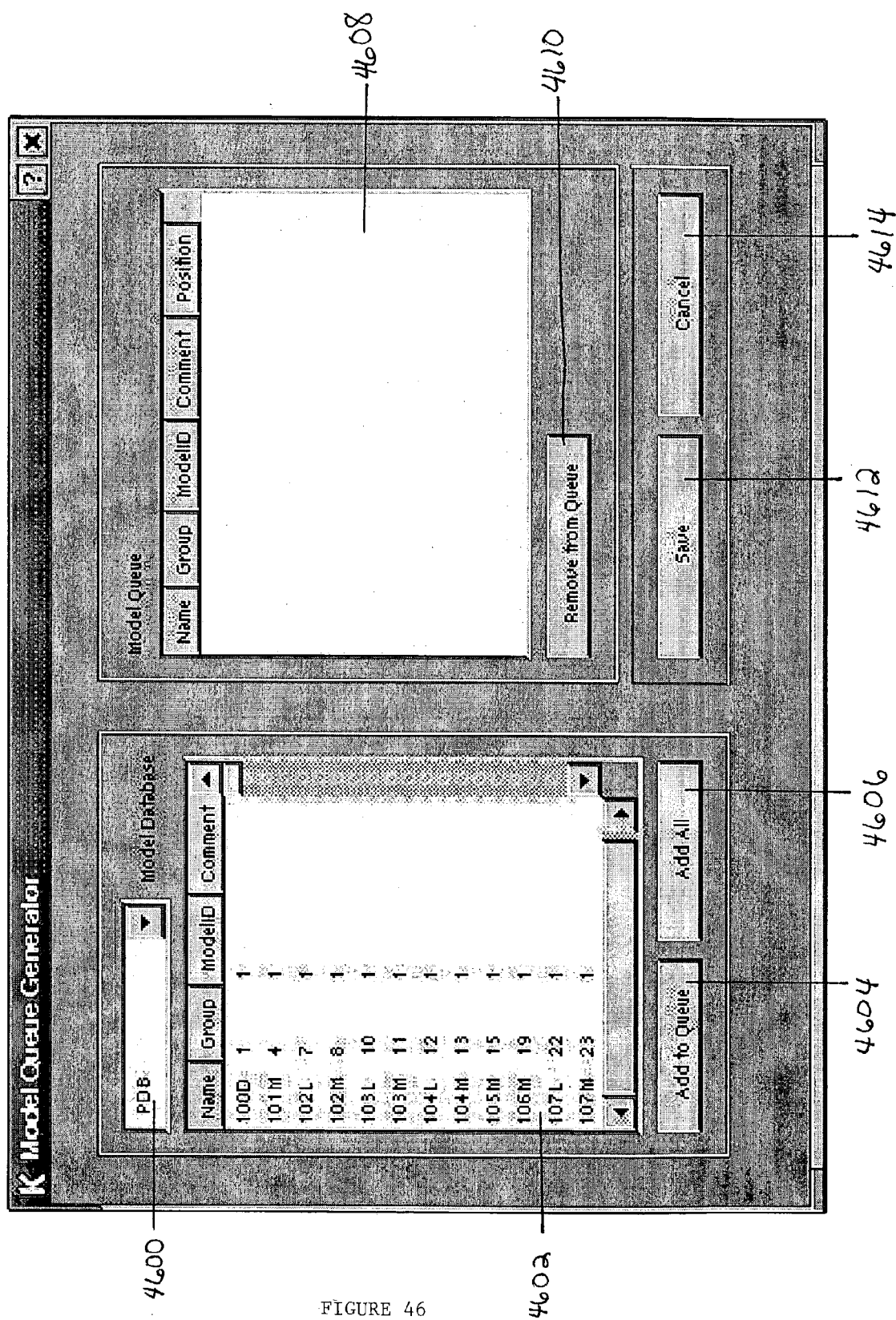
Figure 47:
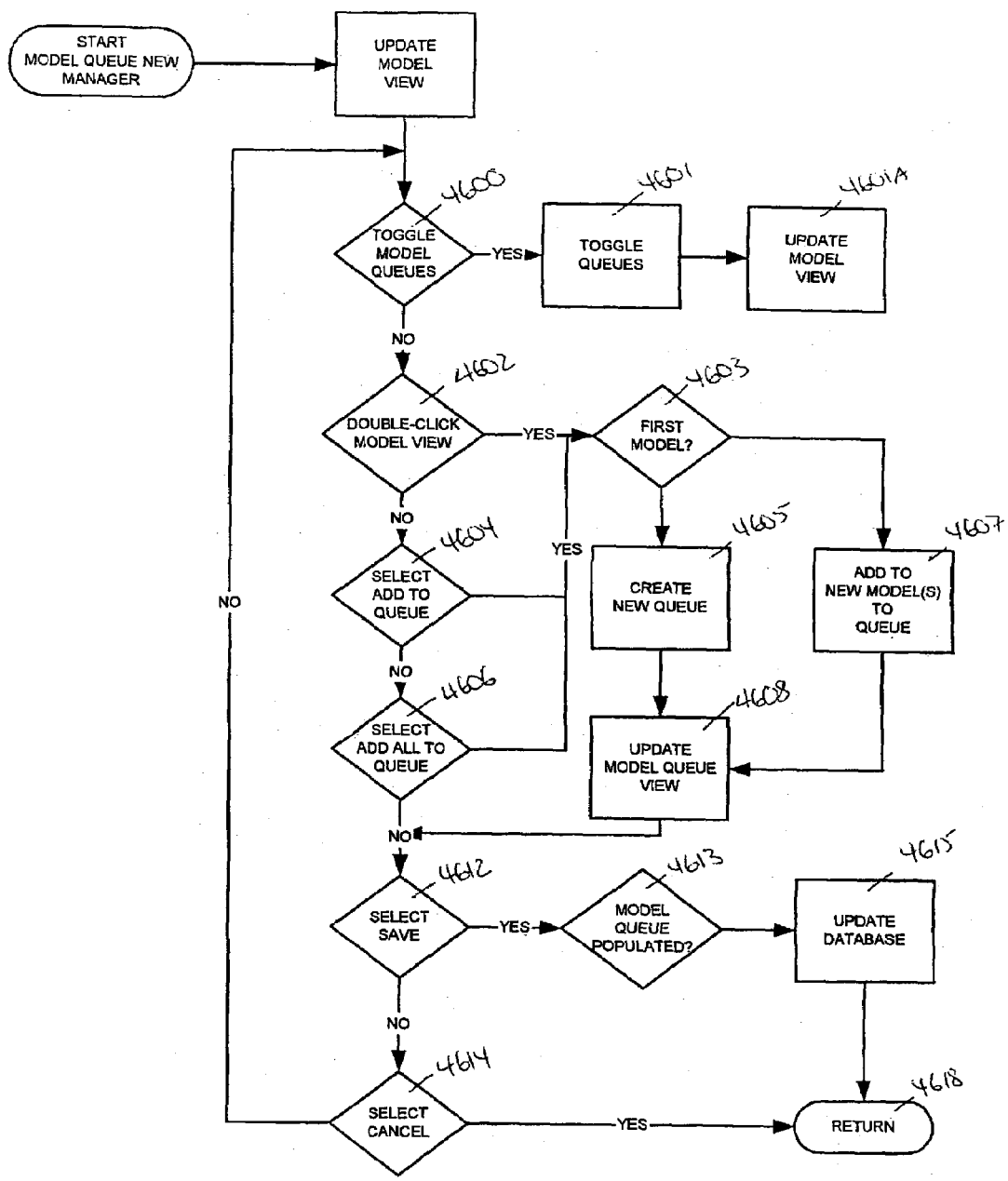

The search model queue selection manager allows the user to select a predefined search model queue. Upon launching the manager, all preset queues are displayed in the queue list view 4400. Entries are distinguished by the name, data id and comments, which are provided for each entry in the list view. A user may select a search model queue for the molecular replacement search by double clicking the appropriate entry in the list view. The action causes the name of the queue to be displayed in the selected model queue text field 4402. The text field will update every time the user double clicks on an entry in the queue list view. These actions are represented by steps 4400–4402 of FIG. 45. A selection may be finalized by clicking on the accept button 4404 where upon the database is updated with the user choice of model queues. Otherwise the user may elect to cancel any selection made and exit the manager by clicking on the cancel button 4406.

New Search Model Queue Manager

The user may choose to construct a new search model queue in the new search model queue manager. The model list view 4602 displays all the search model entries of a database selected by the user. A user may toggle between different model databases by clicking on the database scroll view 4600. Any entry in the list view may be added to the list view by double clicking the entry or highlighting the entry and then pushing the add to queue button 4604. All the entries in a selected database are added to a search model queue by clicking on the add all button 4606. Either of the previously described actions causes the entry in the model list view to be moved to the queue list view 4608. Any entry appearing in the queue list view may be removed by clicking on the remove from queue button 4610. A customized queue may be finalized by clicking on the save button 4612 where upon a new search model queue is created in the database and populated with the listed models. Otherwise, the user may elect to cancel the search model queue build process and exit the manager by clicking on the cancel button 4614.

Execution Manager

Figure 48:
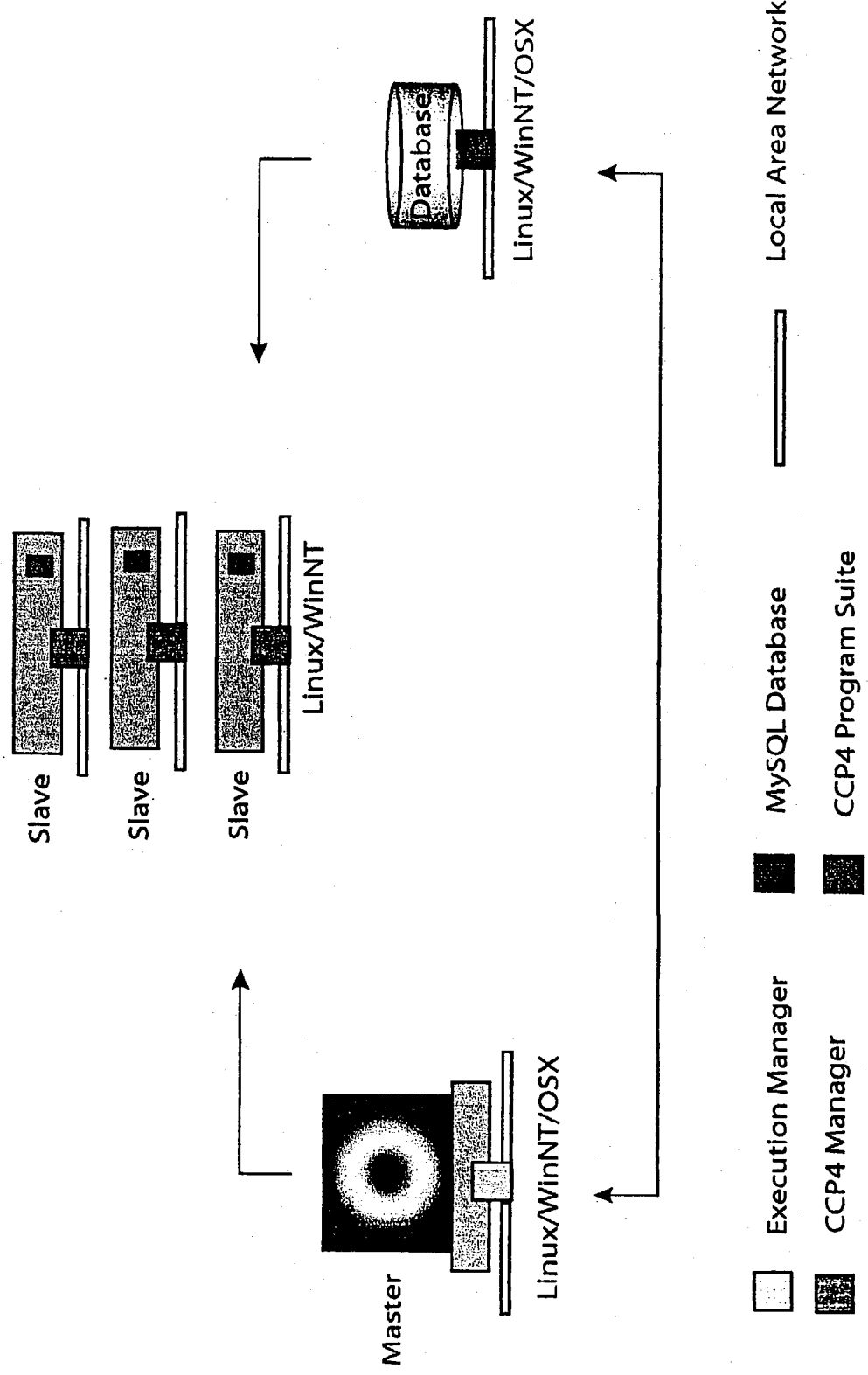

The execution manager is spawned as a separate thread from the run manager. The execution manager is responsible for collecting input parameters defined in the GUI and passing those parameters to various host machines across a computer cluster. As part of the operation, the execution manager recruits, monitors and interacts with hosts connected through a local area network. FIG. 48 shows the basic layout of machines required to execute a molecular replacement according to the present invention. A single machine acts as a master and governs the timing and execution of the CCP4 manager on subordinate slave machines. The execution manager resides on the master machine. Each slave machine must have a copy of the CCP4 manager. Both the master machine and the slave machines have access to the MySQL database. Access is provided through MySQL client libraries.

Figure 49:
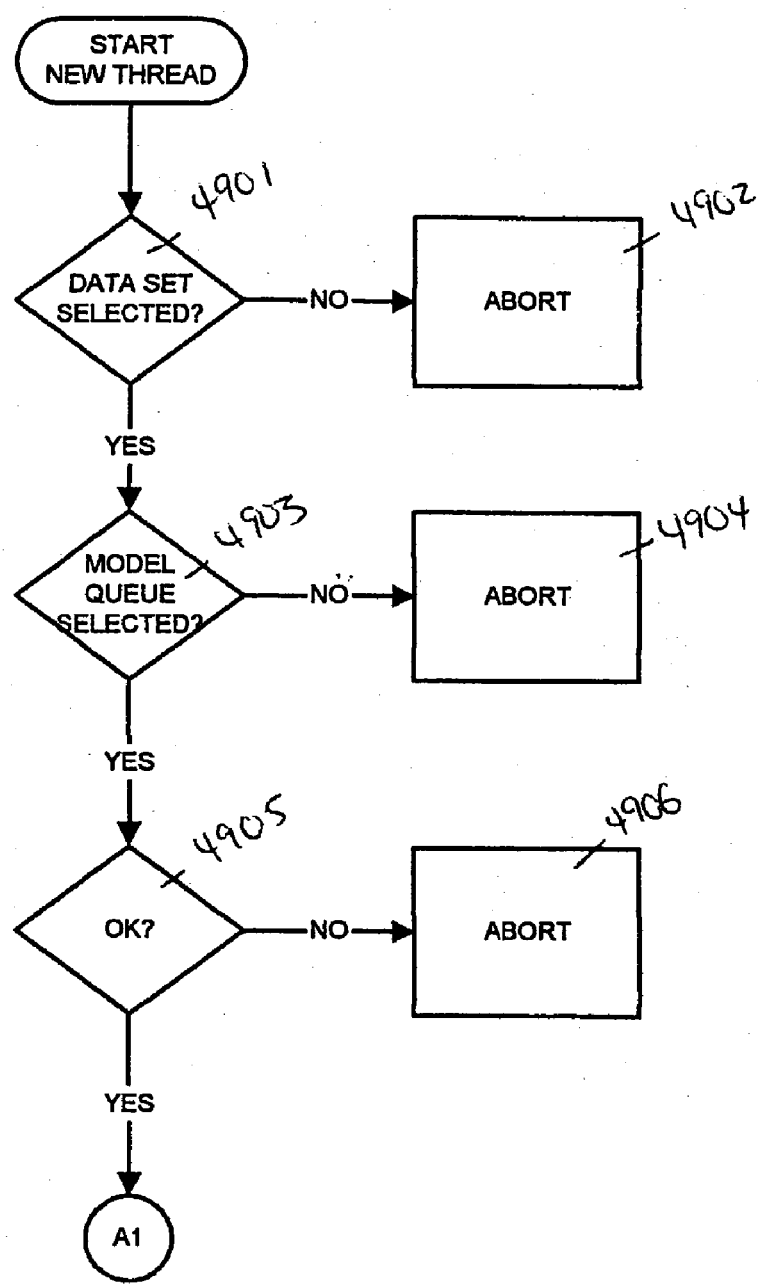
Figure 50:
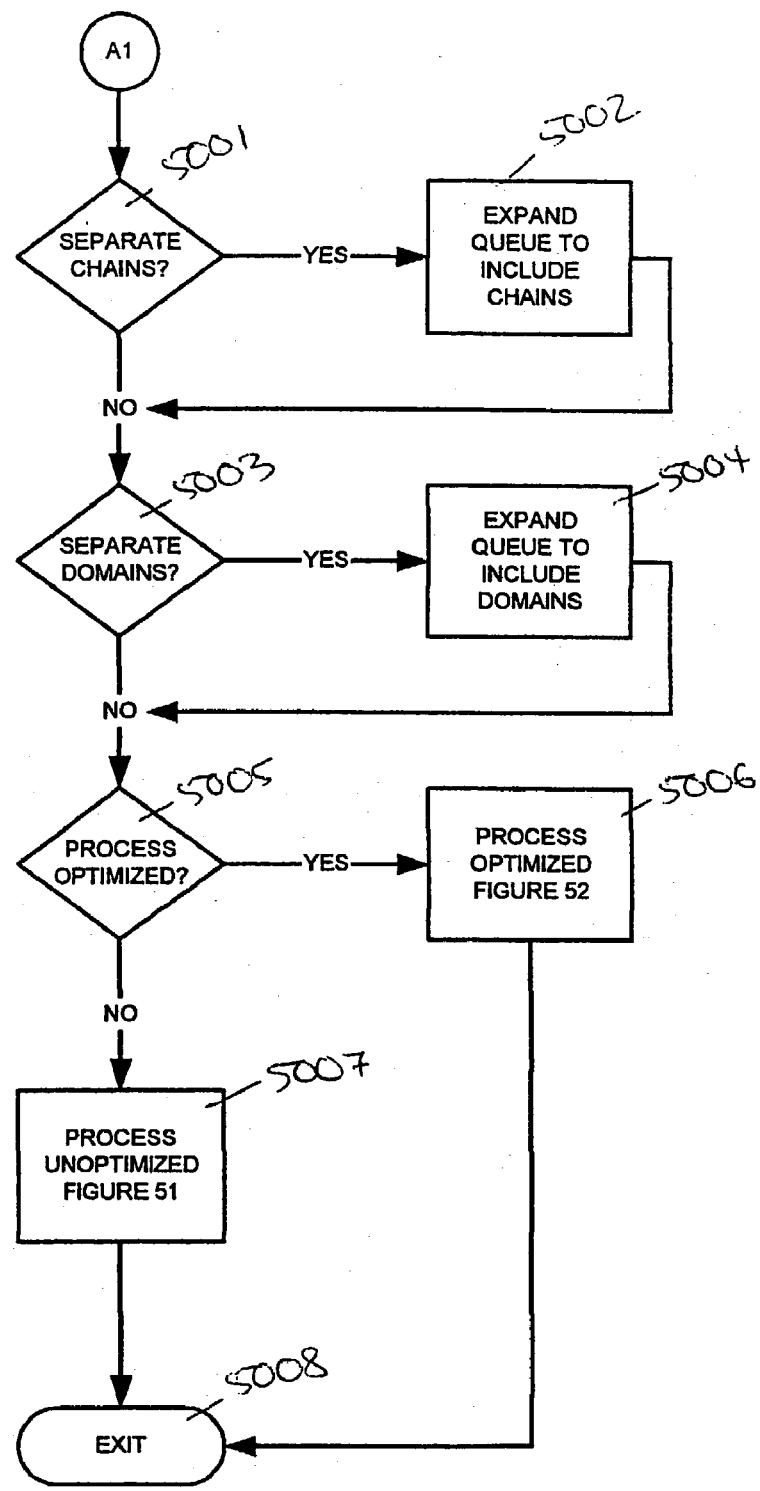
Figure 51:
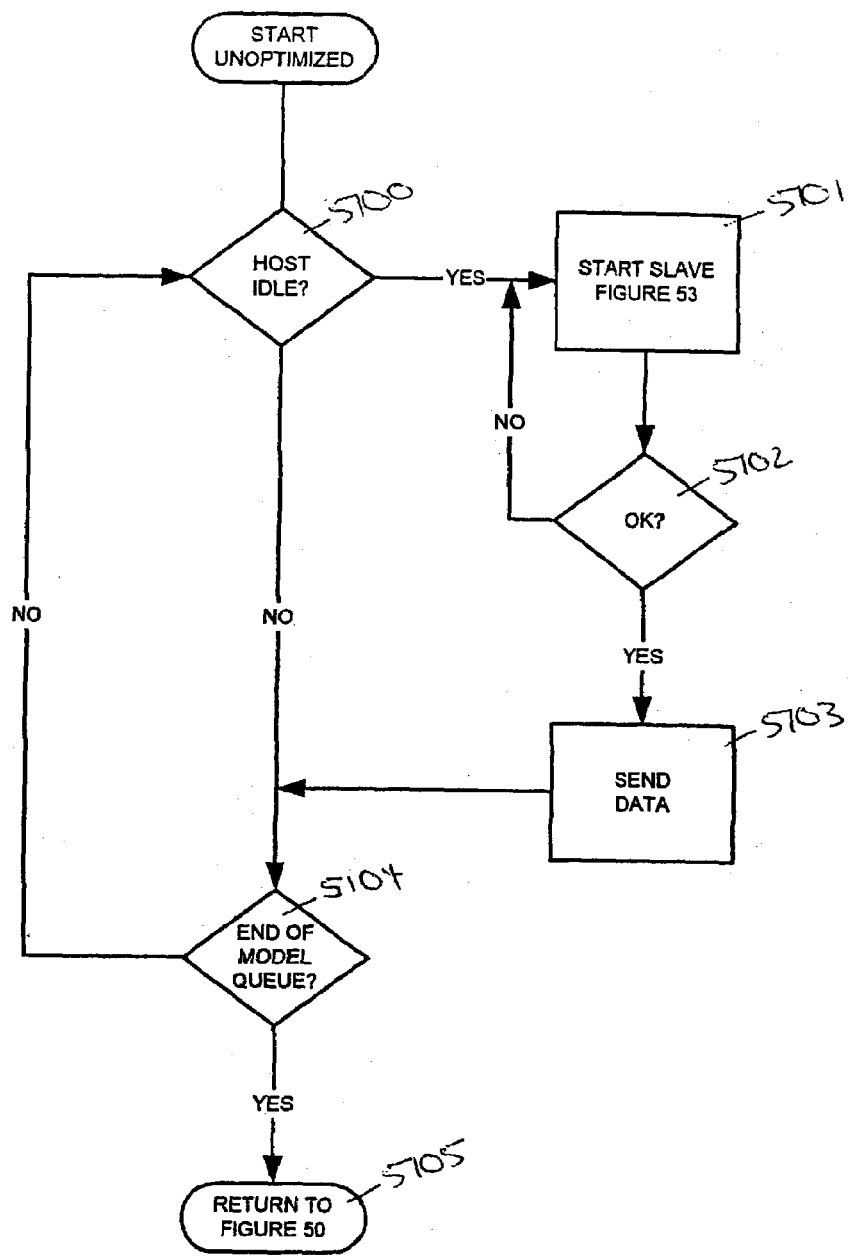
Figure 52:
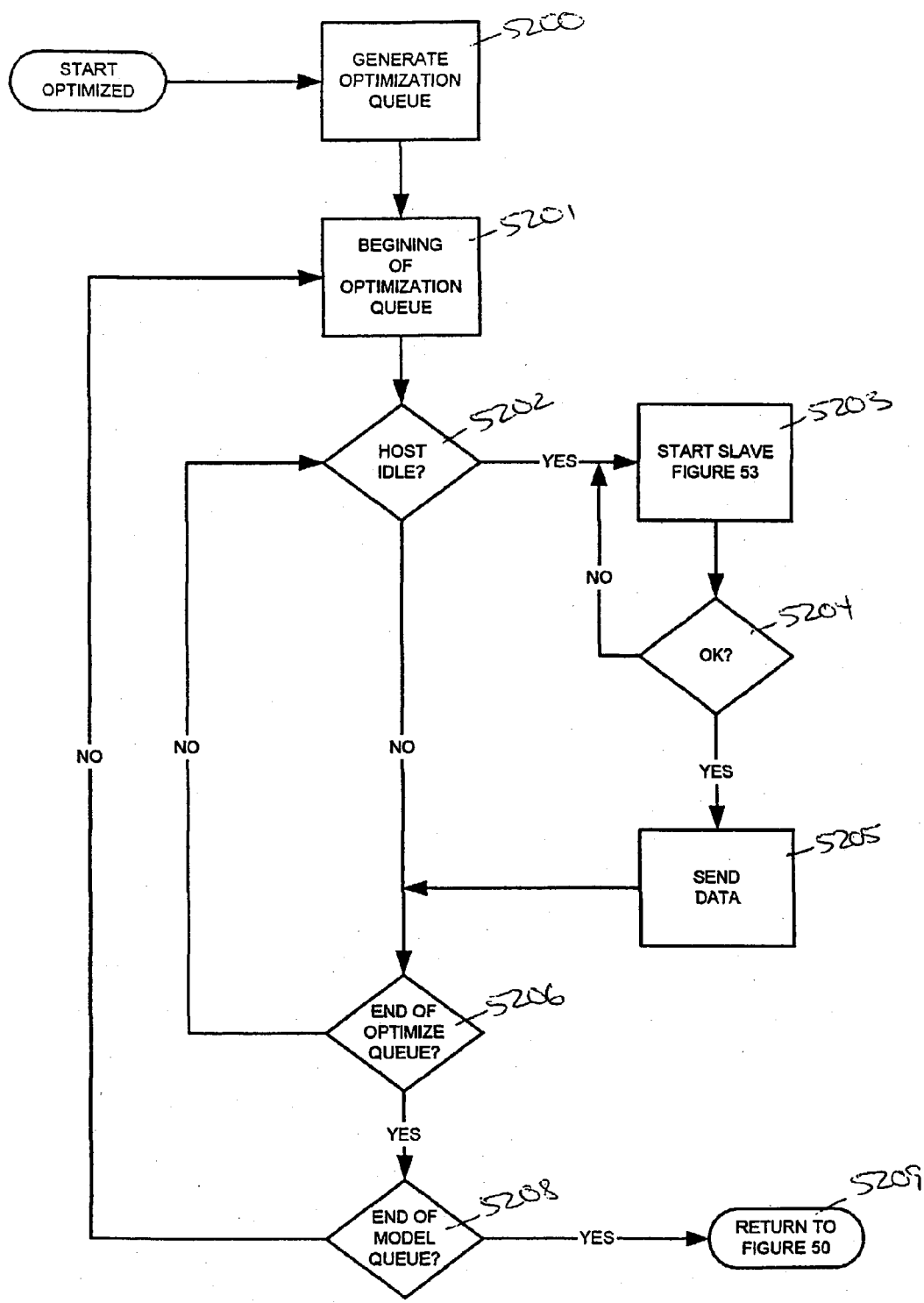

After the execute button 1710 (FIG. 17) has been actuated, the execution manager compiles a list of search models requested by the user. The list is expanded according to flags passed from the GUI. For example, if the subdivide PDB entry into Chains check box 1752 is selected, then each entry in the model queue list is expanded into as many fragments as there are chain identifiers in the coordinate set. These actions are represented by steps 4901–5004 of FIGS. 49 and 50. Next, a host list is compiled, and the various hosts initialized through the PVM interface. Initialization consists of spawning a PVM daemon process on the host machine, which acts as a communication link between the execution manager and the CCP4 manager. This process is represented by steps 5006–5007 of FIG. 50. Once the hosts have all been initialized, the execution manager starts processing the model queue. The CCP4 manager is launched remotely by the execution manager. Parameters required for the CCP4 manager to process a data set/search model pair are passed through the PVM interface. The CCP4 manager acknowledges receipt of the parameters and begins processing the data. Meanwhile, the execution manager continues processing the model queue and sends data to each of the initialized hosts. Once the CCP4 manager has been supplied with data on each of the hosts, the execution manager enters into idle mode and waits for a message to be passed from one of the CCP4 managers indicating that a molecular replacement job has finished. This process is represented by steps 5100–5104 of FIG. 51 and steps 5200–5206 of FIG. 52. Upon notification of a completed or terminated process, the execution manager launches another CCP4 manager on the slave host. The cycle just described is repeated until the last search model has been processed.

CCP4 Manager

A CCP4 manager on the slave host is launched by the execution manager, which resides on the master host. The CCP4 manager responds to the execution manager at several points during execution: at the beginning, to acknowledge that it has been successfully started, again when run parameters have been sent from the execution manager, and finally just before terminating to indicate that a search model has been processed. With the exception of parameters passed from the execution manager, the CCP4 manager operates independently of any other process.

Figure 53:
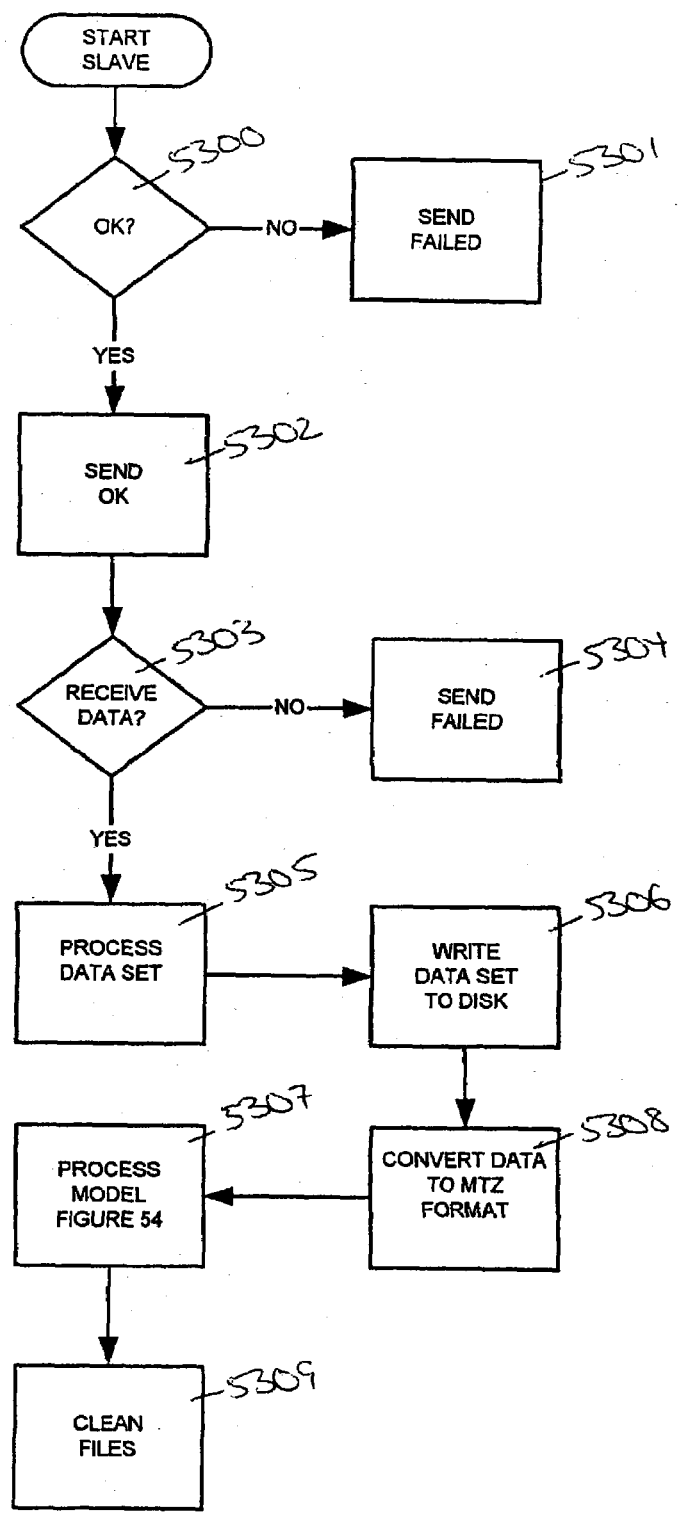
Figure 54:
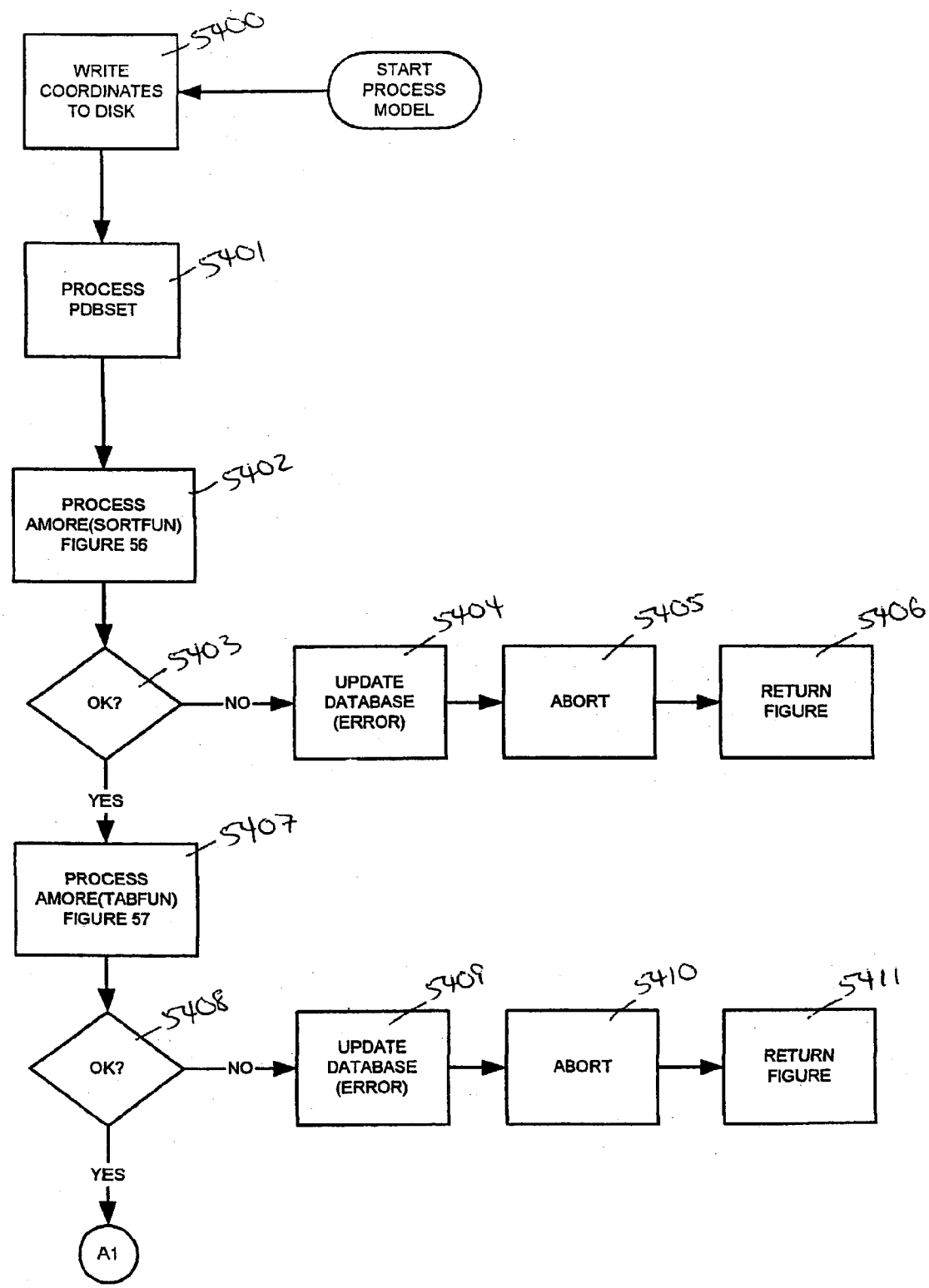
Figure 56:
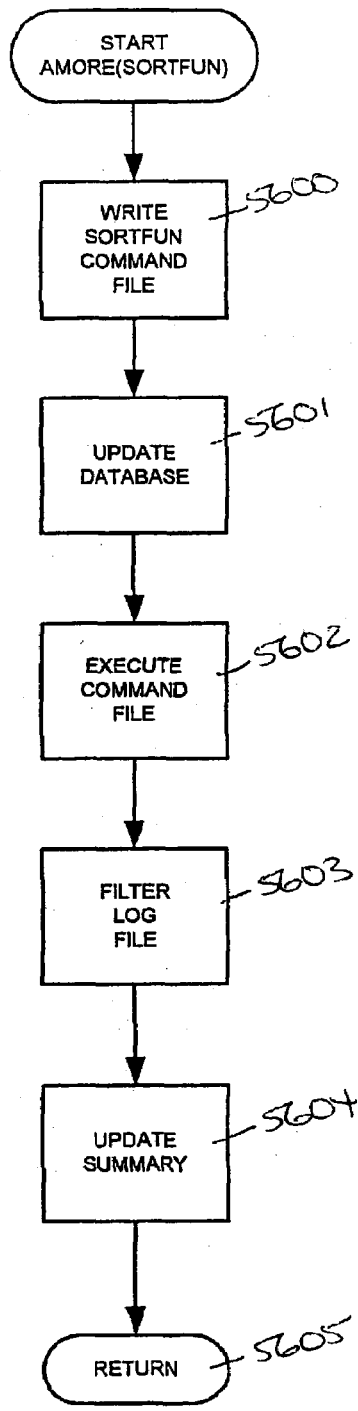
Figure 57:
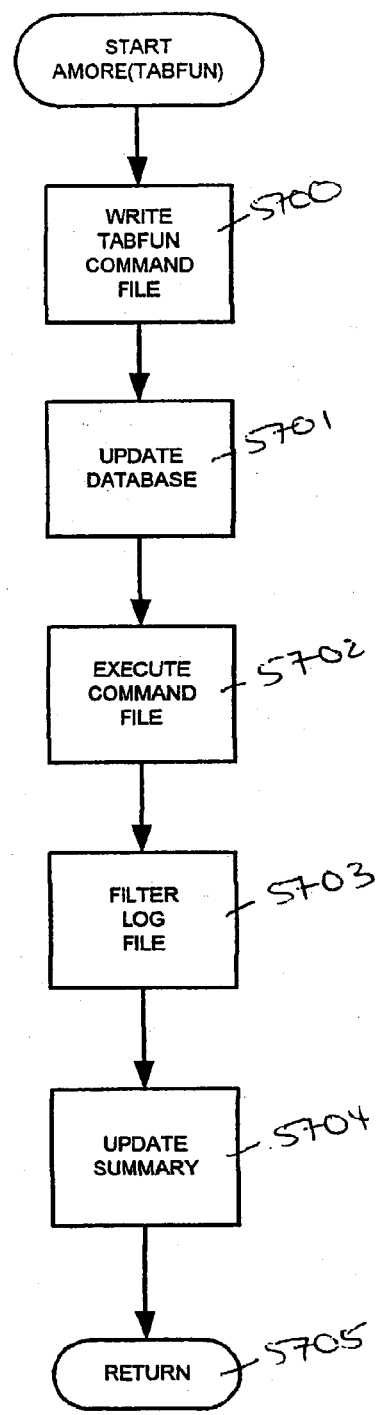

The first action of the CCP4 manager is to download the reflection data set from the database to the hard disk. The files are converted to a binary format compatible with CCP4 programs using f2mtz. Next, the coordinates of the search model are downloaded to the hard disk from the database and then converted to an ASCII formatted text file compatible with CCP4 programs. This process is represented by steps 5305–5308 of FIG. 53. Command files to execute AMoRe SORTFUN and TABFUN functions are written to the hard disk. The parameters used in each of the files are stored in the database. The command files are executed and the output captured in log files. The log files are filtered by the CCP4 manager for confirmation of input parameters and other values necessary to execute subsequent rounds of AMoRe. The TABFUN file provides suggested values for CELL MODEL and SPHERE parameters. These values are processed by the CCP4 manager and included in the command file for the ROTFUN function. The filtered output of the each log file is saved to the database. Any time an error occurs during the execution of AMoRe, the error is documented in the log file. The CCP4 manager also filters the log file for error messages. If an error is found the message is saved to the database. The CCP4 manager does not attempt to correct the problem and treats all errors as fatal. In the case of an error, the CCP4 manager provides the execution manager with an error status and exits. The process is represented by steps 5400–5411 of FIG. 54 and the functional flow diagrams in FIGS. 56–57.

Figure 58:
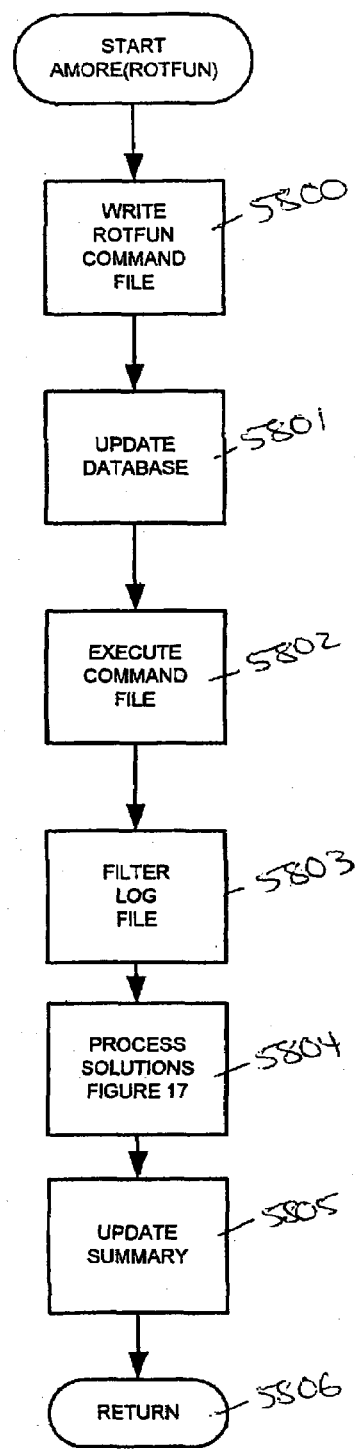
Figure 61:
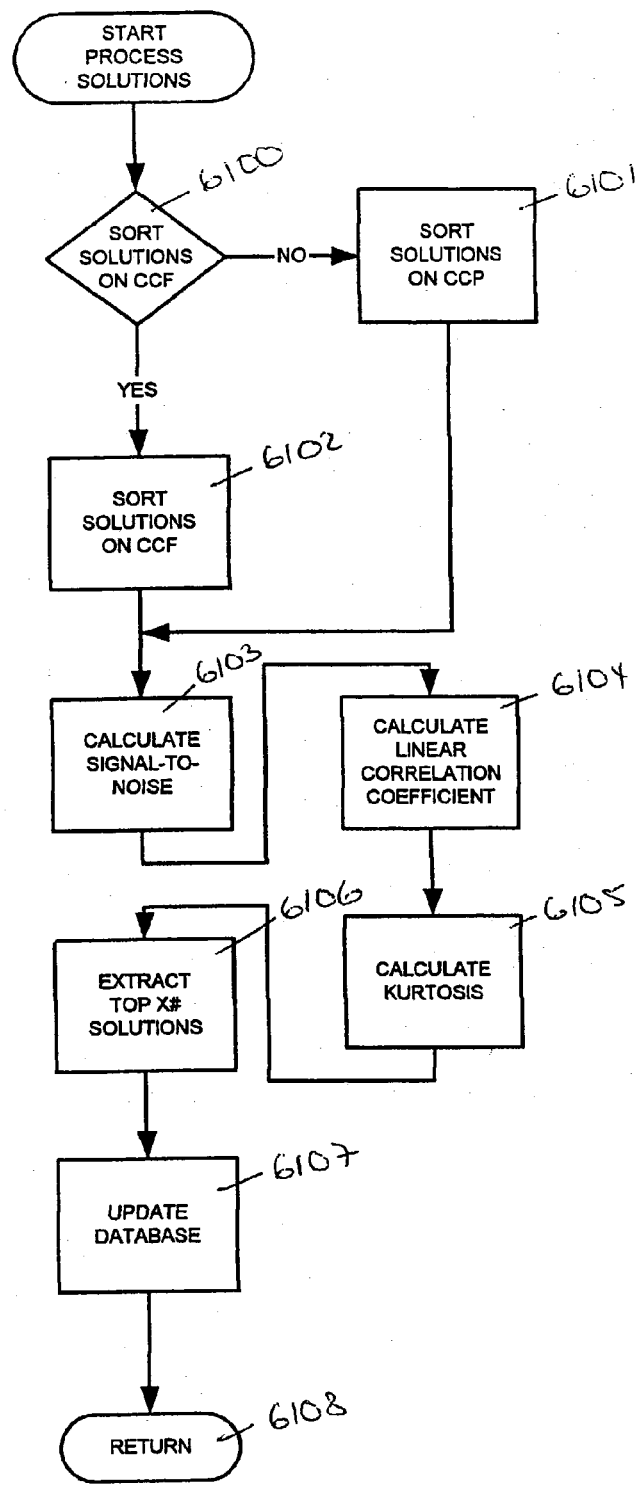

If execution has been successful up to this point, the ROTFUN command file is written to the hard disk, executed, and the output captured in a log file. These steps are captured in the functional flow diagram of FIG. 58. The log file is filtered by the CCP4 manager for confirmation of input parameters and also for solutions of the rotation search. The solutions are sorted according to the strength of either CCF or of CCP. This process is represented by steps 6100–616102 of FIG. 61. The strength of each of the rotation solutions is accessed using several statistical measurements. It is assumed, that correct solutions will appear as outliers in the background of other solutions and that these outliers will impact significantly any statistics performed on the solution data set. Therefore, for some of the statistical measurements, two calculations are carried out: one calculation with the strongest peak included, and another in which the strongest peak is excluded (inclusive and exclusive).

The statistical assessment includes a measure of signal-to-noise for each solution, a ratio of inclusive and exclusive correlation coefficients, and an inclusive and exclusive kurtosis factor. The ratio of correlation coefficients serves as a means to evaluate whether a solution data set is well behaved and provides a context for the signal-to-noise ratio assigned to a solution. The kurtosis factor can also be used to evaluate whether a solution is an outlier. After the solutions have been assigned statistical descriptors, the top five solutions according to CCF or CCP are uploaded to the database. This process is represented by steps 6103–6107 of FIG. 61. If no error has occurred, the CCP4 manager proceeds to the next step—the translation search.

Figure 55:
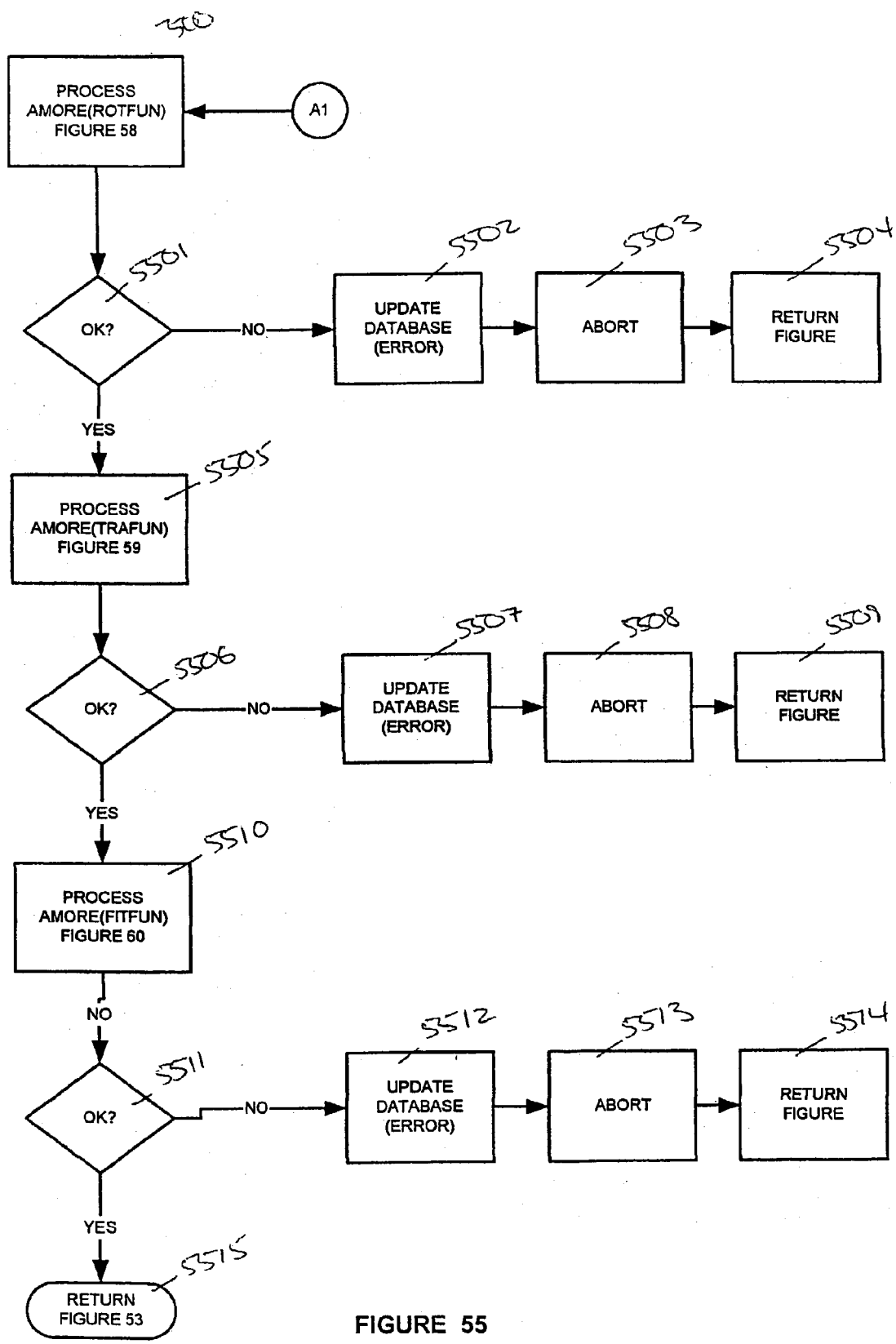
Figure 59:
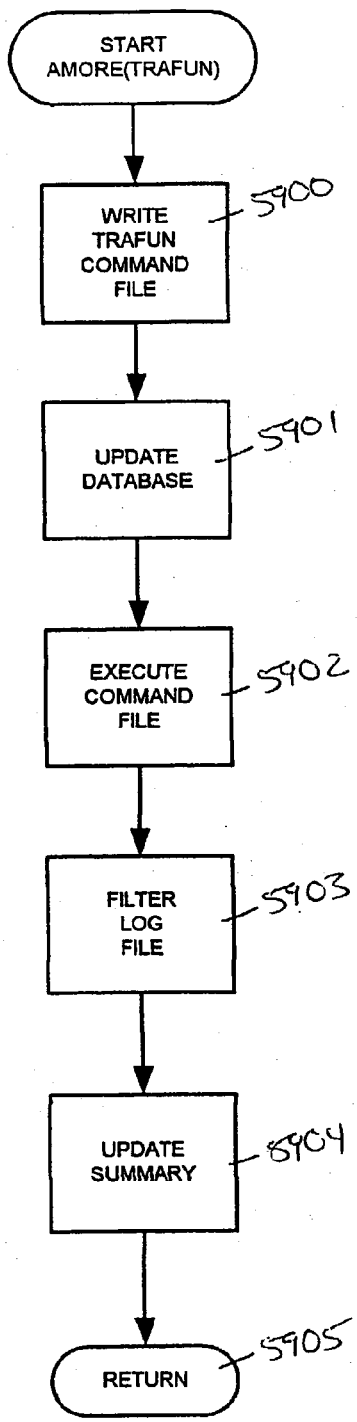

After a rotation search has been made a translation search is conducted using the top five solutions in the rotation function. Command files to execute AMoRe TRAFUN function is written to the hard disk. The parameters used in the file are stored in the database. The command files are executed and the output captured in log files. The log files are filtered by the CCP4 manager for confirmation of input parameters and other values necessary to execute subsequent rounds of AMoRe and saved to the database. This process is represented by steps 5505–5509 of FIG. 55 and steps 5900–5905 of FIG. 59. If no error has occurred, the CCP4 manager proceeds to the next step—rigid-body refinement.

Figure 60:
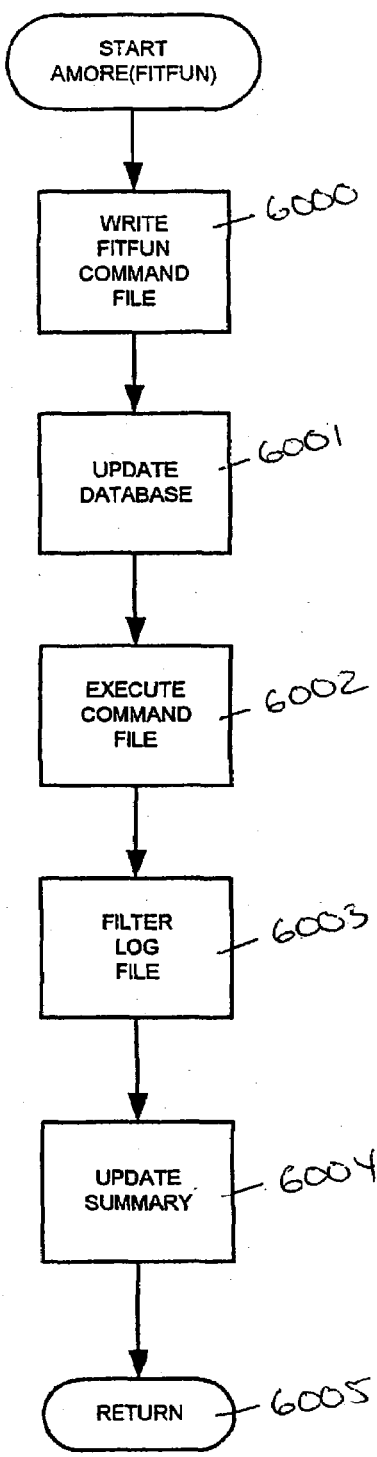

Refined solutions output by the translation module are also filtered from the log file and included in the command file for the FITFUN function of AMoRe. The parameters used in the file are stored in the database. The command files are executed and the output captured in log files. The log files are filtered by the CCP4 manager for confirmation of input parameters and refined solutions from the rigid body refinement. The filtered results are saved to the database. This process is represented by steps 5510–5515 of FIG. 55 and steps 6000–6005 of FIG. 60.

Database Structure: Table Relationships

The database includes tables, having fields or attributes, and forming relationships with one or more tables. Data is mined via the use of keys that link tables to each other. Thus one field can be mapped to any other field. In this manner the entire database can be searched for data. For example, to retrieve the coordinates of a model from the database, the COORD_MODEL_ID field of the Coords table is mapped to the MODEL_ID in the Models table. Information regarding Atom types associated with a set of coordinates is mapped using the COORD_ATOM_ID of an entry in the Coords table. The foregoing are meant to be given by way of example and should not be construed as limiting on the number of fields capable of being mapped by the present invention.

FIG. 62

Shows the relationships for the Projects, User, and Runs tables. The primary key to the Projects table is PROJECT_ID, and the fields include PROJECT_Name, PROJECT_Date, USER_ID, and PROJECT_Comment. The primary key to the Users table is USER_ID and the fields include USER_ORG_ID, USER_Password, and USER_Name. The primary key to the Runs table is RUN_ID and the fields include RUN_PRJCT_ID, RUN_Status, RUN_StartTime, RUN_EndTime, RUN_REFL_ID, RUN_Comment, RUN_Log, and RUN_Parent_ID. Users may access project information through the key PROJECT_USER_ID while Runs included in a project may be accessed through the RUN_PRJCT_ID.

FIG. 63

Figure 62:
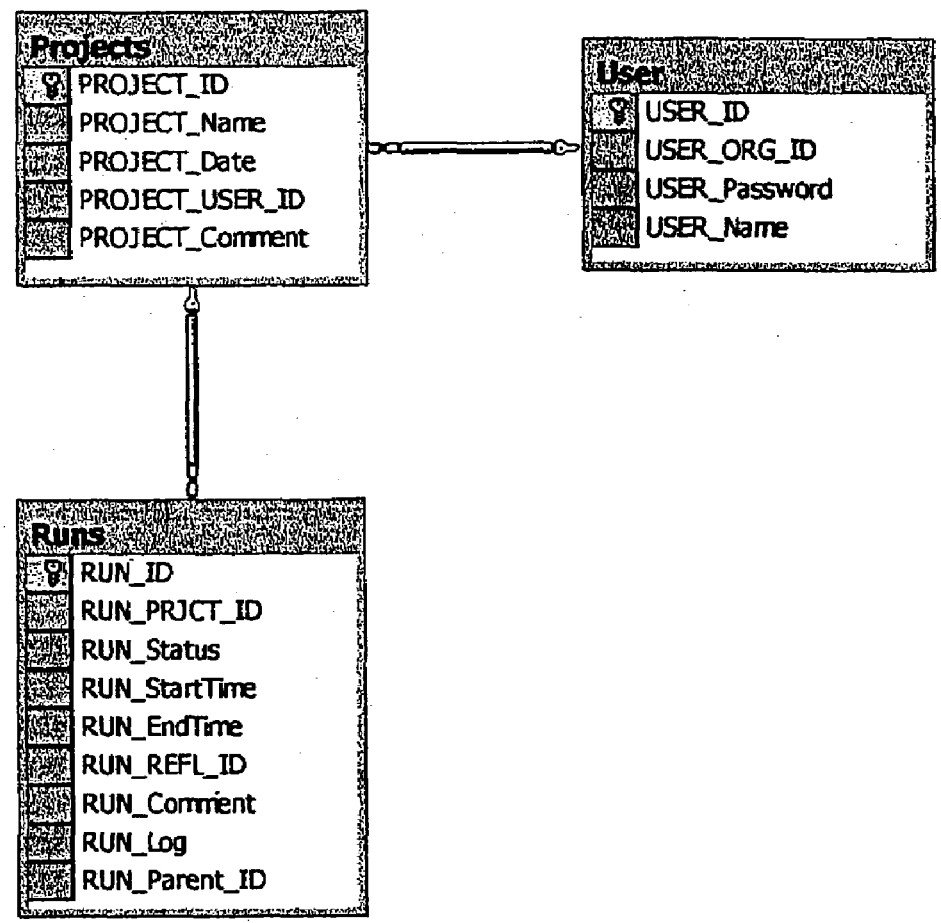

Shows the relationships for the Runs, Reflections, ComQueue, and Projects tables. The Runs and Projects tables are described in FIG. 62. The primary key for the Reflections table is REFL_ID and the fields include REFL_RPARAM_ID. The primary key for the ComQueue table is CQ_ID and the fields include CQ_MQ_ID, CQ_DOM_ID, CQ_CMF_ID, CQ_RUN_ID, CQ_Log, CQ_Position, CQ_Name, and CQ_Summary. Reflections may be accessed from the Run table through the key RUN_REFL_ID while the Runs table may be accessed from the ComQueue table through the CQ_RUN_ID.

FIG. 64

Figure 63:
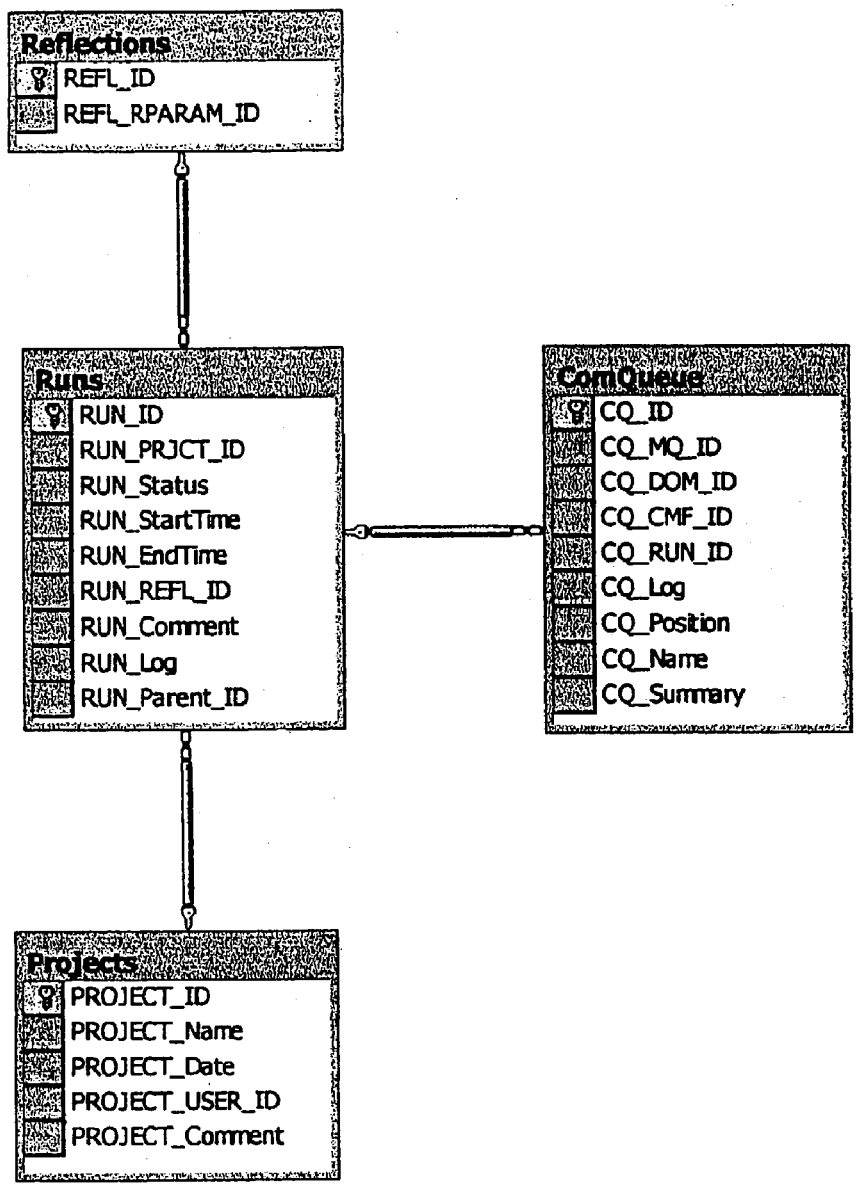
Figure 64:
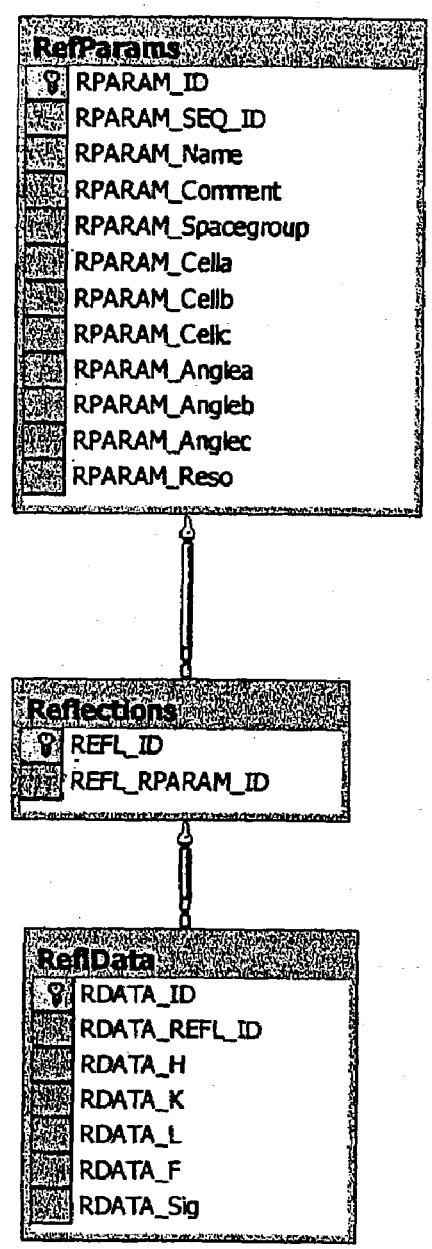
Figure 65:
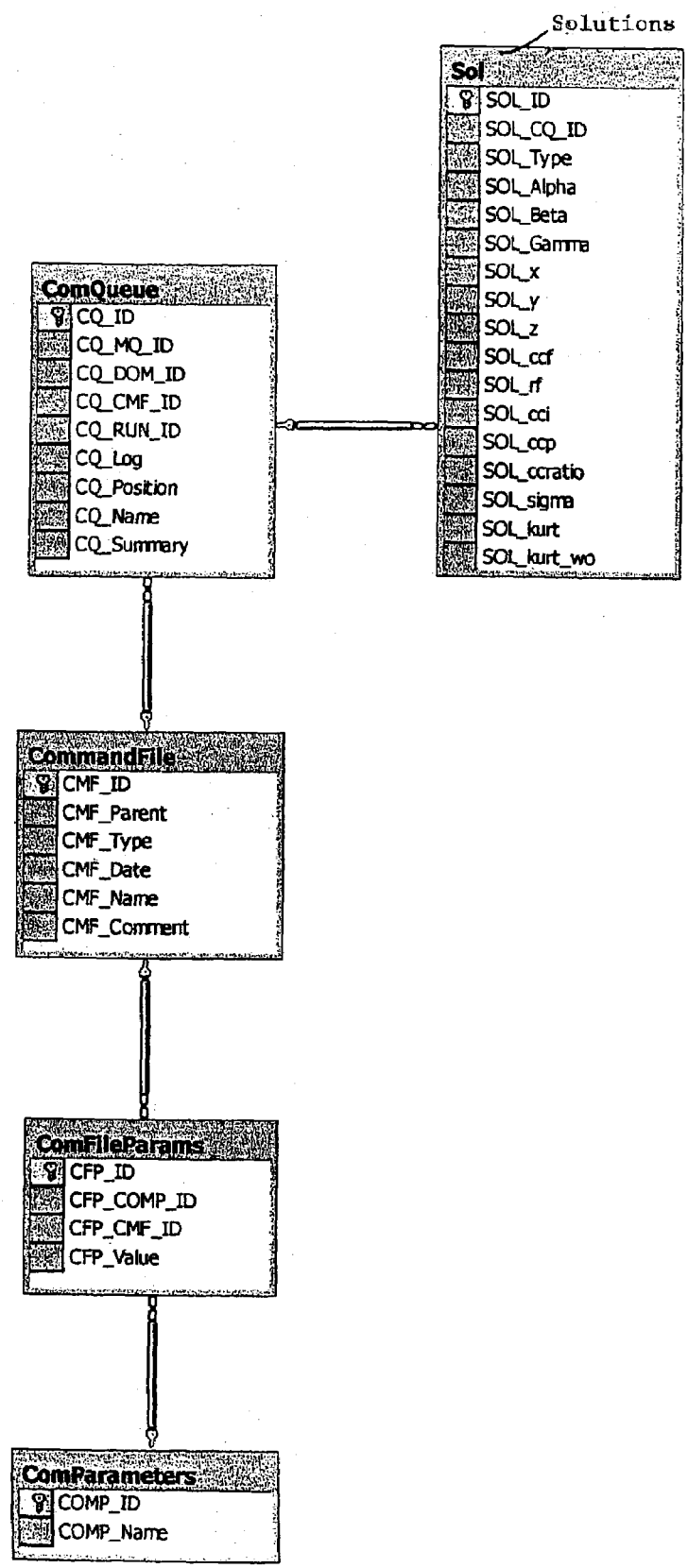

Shows the relationships for the Reflections, RefParams, and the ReflData tables. The Reflections table is described in FIG. 63. The primary key for the RefParams table is RPARAM_ID and the fields include RPARAM_SEQ_ID, RPARAM_Name, RPARAM_Comment, RPARAM_SpaceGroup, RPARAM_Cella, RPARAM_Cellb, RPARAM_Cellc, RPARAM_Anglea, RPARAM_Angleb, RPARAM_Anglec, and RPARAM_Reso. The primary key for the ReflData is RDATA_ID and the fields include RDATA_REFL_ID, RDATA_H, RDATA_K, RDATA_L, RDATA_F, and RDATA_Sig. RefParams may be accessed from the Reflections table through REFL_RPARAM_ID. The Reflections table may be accessed from ReflData through the RDATA_REFL_ID.

FIG. 65

Shows the relationships for the ComQueue, CommandFile, ComFileParams, ComParameters, and Solutions tables. The ComQueue table has been described in FIG. 63. The primary key for the Solutions table is SOL_ID and the fields include SOL_CQ_ID, SOL_Type, SOL_Alpha, SOL_Beta, SOL_Gamma, SOL_x, SOL_y, SOL_z, SOL_ccf, SOL_rf, SOL_cci, SOL_ccp, SOL_ccratio, SOL_sigma, and SOL_kurt, SOL_kurt_wo. The primary key for theCommandFile table is CMF_ID and the fields include CMF_Parent, CMF_Type, CMF_Data, CMF_Name, CMF_Comment. The primary key for the ComFileParams table is CFP_ID and the fields include CFP_COMP_ID, CFP_CMF_ID, CFP_Value. The primary key for the ComParameters table is COMP_ID and the fields include COMP_Name. The Solutions table may be accessed from the ComQueue table through the SOL_CQ_ID. The CommandFile table may be accessed from the ComQueue table through the CQ_CMF_ID while the ComFileParams table may be accessed from the CommandFile table through the CFP_CMF_ID. Finally, the ComParameters table is accessed from the ComFileParams table through the CFP_COMP_ID.

FIG. 66

Shows the relationships for the ComQueue, Domains, Models, and ModelQueues tables. The ComQueue table has been described previously in FIG. 63. The primary key of the Domains table is DOM_ID and the fields include DOM_MODEL_ID, DOM_Unique, DOM_SegID, DOM_Start, DOM_Stop. The primary key of the Models table is MODEL_ID and the fields include MODEL_Parent_ID and MODEL_PARAM_ID. The primary key of the ModelQueues table is MQ_ID and the fields include MQ_USER_ID, MQ_MODEL_ID, MQ_DATB_ID, MQ_Group, MQ_Position, MQ_Name. The Domains table may be accessed from the ComQueues table through the CQ_DOM_ID. The Models table may be accessed from the Domains table through the DOM_MODEL_ID and the Models table may be accessed from the ModelQueues table through the MQ_MODEL_ID.

FIG. 67

Figure 66:
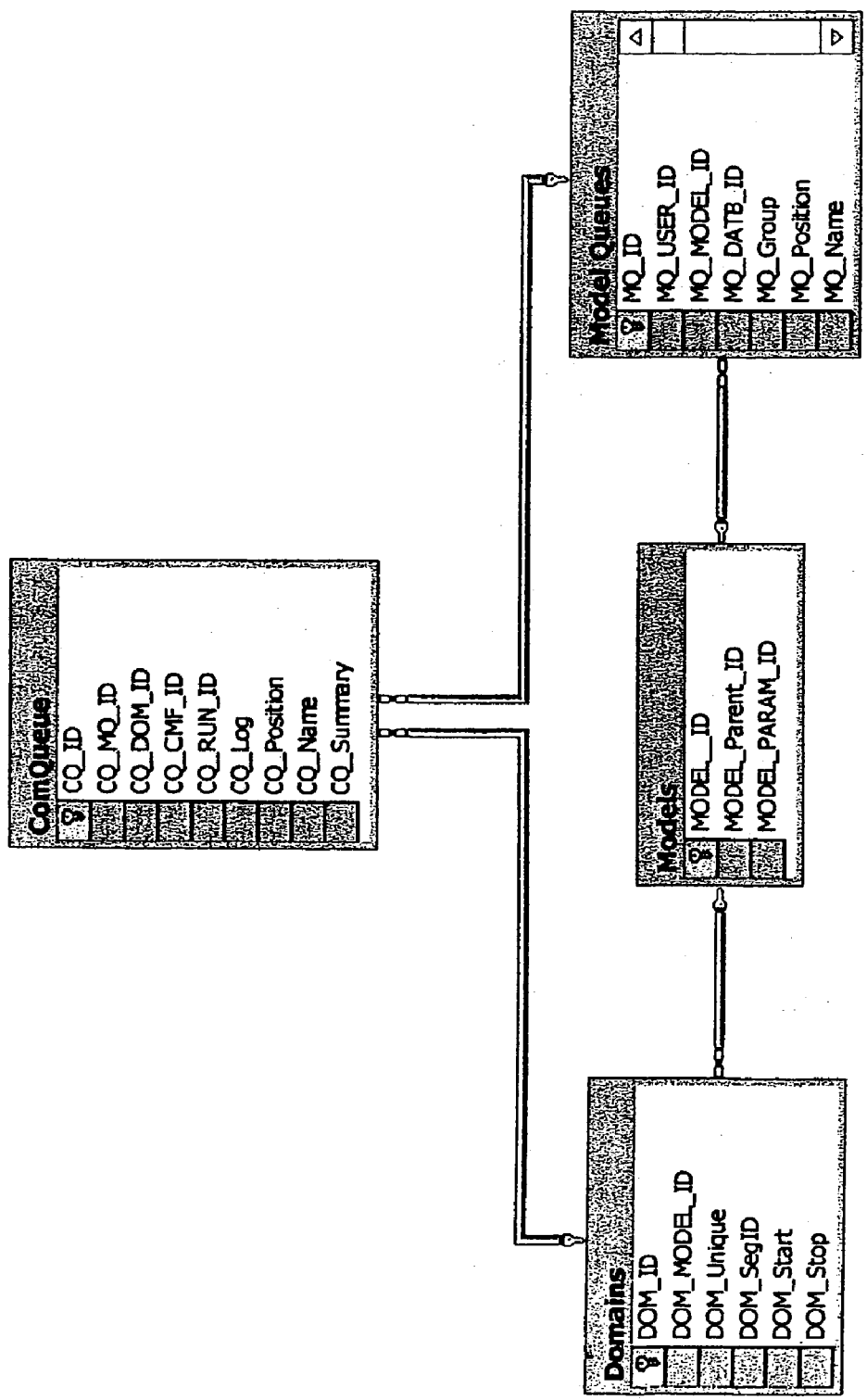
Figure 67:
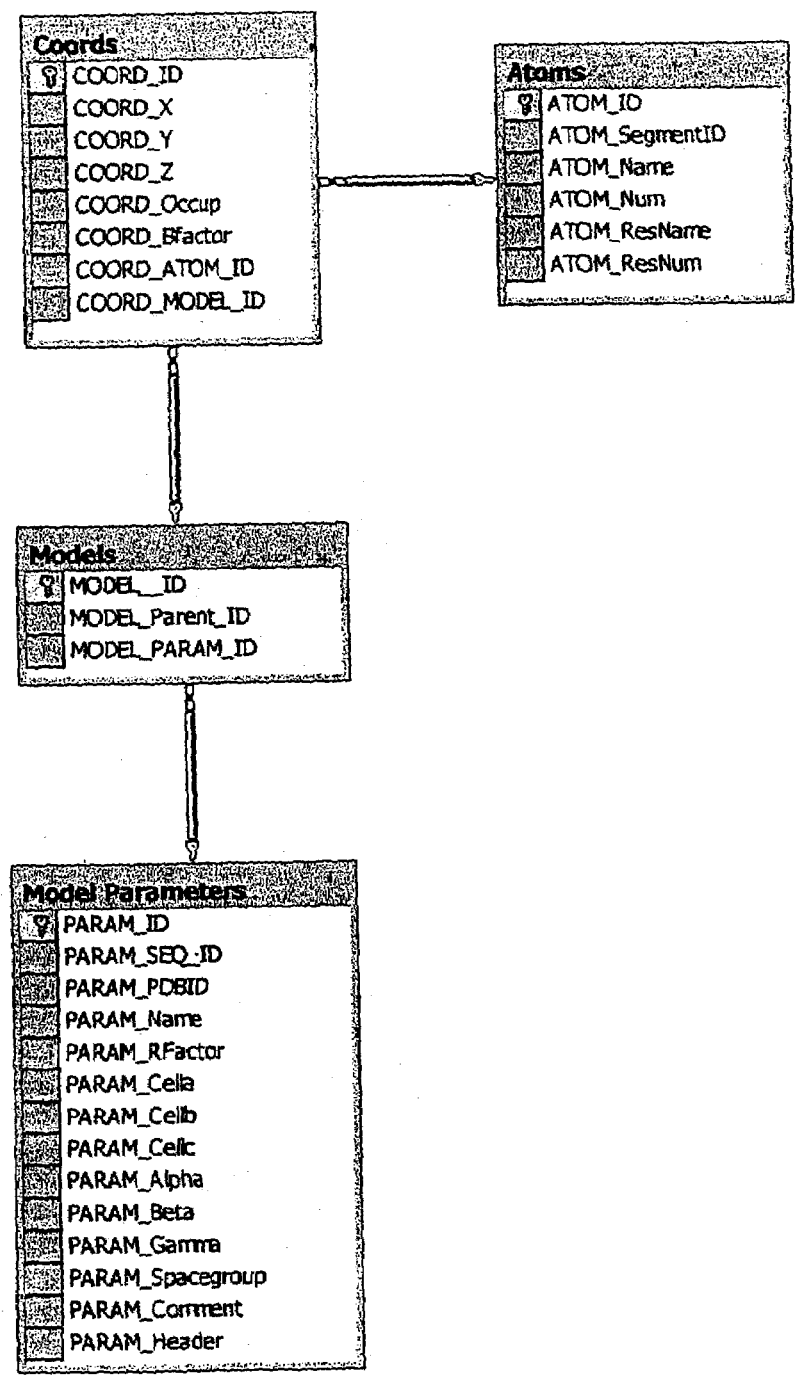
Figure 68:
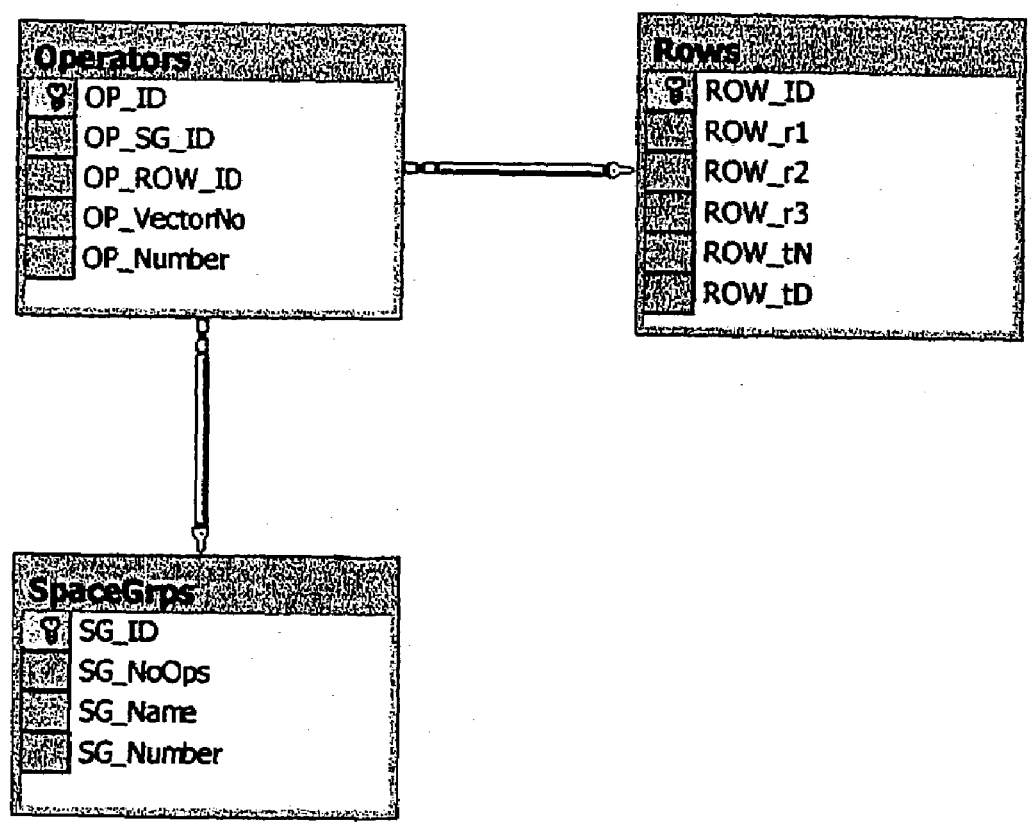

Shows the relationships for the Coords, Atoms, Models, and ModelParams tables. The Models table has been described previously in FIG. 66. The primary key of the Atoms table is ATOM_ID and the fields include ATOM_SegmentID, ATOM_Name, ATOM_Num, ATOM_ResName, and ATOM_ResNum. The primary key of the Coords table is COORD_ID and the fields include COORD_X, COORD_Y, COORD_Z, COORD_Occp, COORD_Bfactor, COORD_ATOM_ID, and COORD_MODEL_ID. The primary key for the ModelParameters table is PARAM_ID and the fields include PARAM_SEQ_ID, PARAM_PDBID, PARAM_Name, PARAM_Rfactor, PARAM_Cella, PARAM_Cellb, PARAM_Cellc, PARAM_Alpha, PARAM_Beta, PARAM_Gamma, PARAM_SpaceGroup, PARAM_Comment, and PARAM_Header. The Atoms table is accessed from the Coords table through the COORD_ATOM_ID. The Models table is accessed from the Coords table through the COORD_MODEL_ID and the ModelParams table is accessed via the MODEL_PARAM_ID from the Models table.

FIG. 68

Shows the relationships for the Rows, Operators, and SpaceGrps tables. The primary key for the Rows table is ROW_ID and the fields include ROW_r1, ROW_r2, ROW_r3, ROW_tN, ROW_TD. The primary key for the Operators table is OP_ID and the fields include OP_ID, OP_SG_ID, OP_ROW_ID, OP_VectorNo, OP Number. The primary key for the SpaceGrps table is SG_ID and the fields include SG_NoOps, SG_Name, SG_Number. The Rows table is accessed from the Operators table using the OP_ROW_ID. The SpaceGrp table is accessed from the Operators table via the OP_SG_ID.

BIBLIOGRAPHY

1. Goldman, B. B. and W. T. Wipke, Quadratic shape descriptors. 1. Rapid superposition of dissimilar molecules using geometrically invariant surface descriptors. J Chem Inf Comput Sci, 2000. 40(3): p. 644–58.
2. Robinson, D. D., P. D. Lyne, and W. G. Richards, Partial molecular alignment via local structure analysis. J Chem Inf Comput Sci, 2000. 40(2): p. 503–12.
3. Flower, D. R., DISSIM: a program for the analysis of chemical diversity. J Mol Graph Model, 1998. 16(4–6): p. 239–53, 264.

4. Cosgrove, D. A., D. M. Bayada, and A. P. Johnson, A novel method of aligning molecules by local surface shape similarity. J Comput Aided Mol Des, 2000. 14(6): p. 573–91.
5. Lemmen, C. and T. Lengauer, Computational methods for the structural alignment of molecules. J Comput Aided Mol Des, 2000. 14(3): p. 215–32.
6. Bemis, G. W. and M. A. Murcko, The properties of known drugs. 1. Molecular frameworks. J Med Chem, 1996. 39(15): p. 2887–93.
7. Good, A. C., The calculation of molecular similarity: alternative formulas, data manipulation and graphical display. J Mol Graph, 1992. 10(3): p. 144–51, 162.
8. Masek, B. B., A. Merchant, and J. B. Matthew, Molecular skins: a new concept for quantitative shape matching of a protein with its small molecule mimics. Proteins, 1993. 17(2): p. 193–202.
9. Holm, L. and C. Sander, Protein structure comparison by alignment of distance matrices. J Mol Biol, 1993. 233(1): p. 123–38.
10. Owen, D. J., et al., Two structures of the catalytic domain of phosphorylase kinase: an active protein kinase complexed with substrate analogue and product. Structure, 1995. 3(5): p. 467–82.
11. Berman, H. M., et al., The Protein Data Bank. Nucleic Acids Res, 2000. 28(1): p. 235–42.
12. Harada, Y., et al., A translation function combining packing and diffraction information: applicaton to lysozyme (high-temperature form). Acta Crystallogr A, 1981.37: p. 398–406.
13. Crowther, R. A. and D. M. Blow, A Method of Positioning a Known Molecule in an Unknown Crystal Structure. Acta Cryst., 1967. 23: p. 544–548.
14. Foadi, J., et al., A flexible and efficient procedure for the solution and phase refinement of protein structures. Acta Crystallogr D Biol Crystallogr, 2000. 56(Pt 9): p. 1137–47.
15. Navaza, J., AMoRe: an Automated Package for Molecular Replacement. Acta Cryst, 1994. A50: p. 157–163.
16. Murzin, A. G., et al., SCOP: a structural classification of proteins database for the investigation of sequences and structures. J Mol Biol, 1995. 247(4): p. 536–40.

What is claimed is:

1. A method for managing an execution of distributed molecular replacement searches over a heterogeneous network of computers, said method including:
  a. configuring a computer cluster such that there is one master computer and a plurality of remote slave computers;
  b. notifying an available remote computer host in the computer cluster of a reflection data, search model or search model fragment, command queue, and run parameters required for execution of a distributed molecular replacement search;
  c. executing the distributed molecular replacement search at a remote slave host;
  d. filtering distributed molecular replacement output files for solution;
  e. scoring solutions at the remote host for the presence of a distributed molecular replacement solution;
  f. loading the solutions into a database;
  g. listening for a response from the remote host indicating that the distributed molecular replacement search has been completed and that the host is available for another distributed molecular replacement search; and
  h. repeating steps c through h until a search model queue is completed.

2. The method claimed in claim 1, further comprising:
  a. initialization of a computer cluster.

3. The method claimed in claim 1, further comprising:
  a. loading reflection data information from the database into master computer memory.

4. The method claimed in claim 1, further comprising:
  a. generating and loading a search model queue information from the database into the master computer memory.

5. The method claimed in claim 1, further comprising:
  a. expanding a search model queue to include a queue of search model fragments if requested.

* * * * *

UNITED STATES PATENT AND TRADEMARK OFFICE
CERTIFICATE OF CORRECTION

PATENT NO. : 7,203,683 B2 Page 1 of 1
APPLICATION NO. : 10/269401
DATED : April 10, 2007
INVENTOR(S) : M.B Mixon et al.

It is certified that error appears in the above-identified patent and that said Letters Patent is hereby corrected as shown below:

On the Title Page, Item (54) Title "*AMORE*" should read --AMoRe--

On the Title Page, Item (75) Inventors "LaJolla," should read --San Diego,--

Col. 1 line 3 "*AMORE*" should read --AMoRe--

Signed and Sealed this

Thirty-first Day of July, 2007

JON W. DUDAS
*Director of the United States Patent and Trademark Office*